(12) United States Patent
Braman et al.

(10) Patent No.: US 7,235,362 B2
(45) Date of Patent: *Jun. 26, 2007

(54) COMPOSITIONS AND METHODS FOR PROTEIN ISOLATION

(75) Inventors: Jeffrey Carl Braman, Carlsbad, CA (US); Carsten-Peter Carstens, San Diego, CA (US); Natalia Novoradovskaya, San Diego, CA (US); Rajesh Bagga, San Diego, CA (US); Lee Scott Basehore, Lakeside, CA (US)

(73) Assignee: Stratagene California, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/987,388

(22) Filed: Nov. 12, 2004

(65) Prior Publication Data

US 2005/0158711 A1    Jul. 21, 2005

Related U.S. Application Data

(63) Continuation-in-part of application No. 10/712,137, filed on Nov. 13, 2003.

(51) Int. Cl.
*C12Q 1/68* (2006.01)
*G01N 33/53* (2006.01)
*C12P 21/02* (2006.01)
*C12N 15/63* (2006.01)
*C07K 1/22* (2006.01)

(52) U.S. Cl. .................... 435/6; 435/7.1; 435/69.1; 435/252.3; 435/254.11; 435/320.1; 435/325; 530/413

(58) Field of Classification Search ............ None
See application file for complete search history.

(56) References Cited

U.S. PATENT DOCUMENTS

| | | | | |
|---|---|---|---|---|
| 5,747,334 A | * | 5/1998 | Kay et al. ................ | 435/320.1 |
| 5,939,288 A | * | 8/1999 | Thornburg ................ | 435/69.8 |
| 2002/0061513 A1 | | 5/2002 | Seraphin et al. ............ | 435/4 |
| 2002/0102655 A1 | * | 8/2002 | Laible et al. .............. | 435/69.7 |
| 2005/0032173 A1 | * | 2/2005 | Rojas et al. ............... | 435/69.7 |
| 2005/0079201 A1 | | 4/2005 | Rathenow et al. .......... | 424/424 |
| 2005/0118646 A1 | * | 6/2005 | Boniface et al. ............ | 435/7.1 |

OTHER PUBLICATIONS

Zheng et al., "A new expression vector for high level protein production, one step purification and direct isotopic labeling of calmodulin-binding peptide fusion proteins," Gene, vol. 186, polypeptide. 55-60, 1997.*

Keefe et al., "One-Step Purification of Recombinant Proteins Using a Nanomolar-Affinity Streptavidin-Binding Peptide, the SBP-Tag," Prot. Exp. and Purif, vol. 23, pp. 440-446, 2001.*

Hinrichsen & Blackshear, (1993) *Regulation of Peptide-Calmodulin Complexes by Protein Kinase C in vivo.* PNAS, 90:1585-1589.

Noonan, et al., (2002) *A Calmodulin Binding Site . . .* Arch. Biochem & Biophys., 398(1):132-140.

Puig, et al., (2001) *The Tandem Affinity Purification (TAP) Method: A General Procedure of Protein Complex Purification.* Methods 24:218-229.

Riguat, et al., (1999) *A Generic Protein Purification Method for Protein Complex Characterization and Proteome Exploration.* Nature Biotechnology, 17:1030-1032.

Stofko-Hahn, et al., (1992) *A Single Step Purification for Recombinant Proteins.* FEBS 302(3);274-278.

Terpe, K., (2003) *Overview of tag Protein Fusions: from Molecular and Biochemical Fundamentals to Commercial Systems.* Appl. Microbiol. Biotechnol., 60:523-533.

Wilson, et al., (2001) *The Use of mRNA Display to Select High-Affinity Protein-Binding Peptides.* PNAS, 98(7):3750-3755.

Keefe, et al., "One-Step Purification of Recombinant Proteins Using a Nanomolar-Affinity Streptavidin-Binding Peptide, the SBP-Tag," Protein Expression and Purification (2001), vol. 23, pp. 440-446.

Stofko-Hahn, et al., "A single step purification for recombinant proteins. Characterization of a microtubule associated protein (MAP 2) fragment which associates with the type II cAMP-dependent protein kinase," FEBS (1992), vol. 302, No. 3, pp. 274-278.

Terpe, "Overview of tag protein fusions: from molecular and biochemical fundamentals to commercial systems," Appl. Microbiol. Biotechnol. (2003), vol. 60, pp. 523-533.

Zheng, et al., "A new expression vector for high level protein production, one step purification and direct isotopic labeling of calmodulin-binding peptide fusion proteins," Gene (1997), vol. 186, pp. 55-60.

PCT International Search Report, PCT/US04/37819, May 19, 2006.

* cited by examiner

*Primary Examiner*—Robert A. Wax
(74) *Attorney, Agent, or Firm*—Kathleen M. Williams; Edwards Angell Palmer & Dodge, LLP

(57) ABSTRACT

The invention provides for polynucleotides and vectors comprising at least two tag sequences. In particular, preferred vectors are viral vectors. The invention also provides for polynucleotides and vectors comprising a streptavidin binding peptide sequence and a calmodulin binding peptide sequence. The invention also provides for polynucleotides and vectors wherein a gene of interest is fused in frame to at least two tag sequences, for example, a streptavidin binding peptide sequence and a calmodulin binding peptide sequence. The invention also provides for methods of using the polynucleotides and vectors of the invention for detecting and/or isolating protein complexes or identifying a binding partner for a protein of interest.

21 Claims, 18 Drawing Sheets

FIG. 1

| Name | No. | Sequence |
|---|---|---|
| SB1 | 3 | MDEKTHCTISMNGAVPLVPHEPQGDPLRLLHRPQDPLVALVEHHEGVDRGLVALPELHAEELGEPVGDLVQGPVEQVQGVVDALVWRLPPS |
| SB2 | 2 | MDEKTHCFHPGDHLVRLVEELQALAEGLQRQGGRQPHRLPRRREHRLQLLLDEAHPQAGDPLRRRAHQVDGRLLLQHHPQGDRLLHRLVLEAHPQDRLGLAVHHH |
| SB3 | 4 | MTRRPTASSSCVRHLLAROGEHGHQALEDRDKARHVRLVEGDVEVLGGLDRLARARHREALEPQAGLVHLPLEGGDLGHLRLVLEAHPQAGLVHHH |
| SB4 | 1 | MDEKTHWGISTMRGEPLLHEPQAGRLPLDRRRARHRRILGAEPGGVDHGLRLRLLDDHRPLVPDHEPQRGPLQRGDLPQVVPLVRLRHAHVLGLAAATYK |
| SB5 | 3 | MDEKTHWNVYHPQGDLLVRGHGHDVEALHDQGLHEQLDLLVGPPPEVVRALRGEVLGGLRRLVPLADEPQGEALDQARQPQHLLELEHHRALPPALVWRLPPS |
| SB6 | 1 | MDEKTHWLNNPELLARLDGLREGEDHPLVLEHHPQGDLLDQPLGRHRALDGEVREGDRPLDQGGEEDLGALVDDDGEVLDGLVHVGVHVHDPAVCGCHHH |
| SB7 | 1 | MDEKTHWPGTLNSFPTHWMSAVGNGKIDCSPNMLSINHWLSSGHPDGALDDQLEPQGDALVGRDGVVQALRLEGQHQHRRLAQRRADRHRQLVWRLPPS |
| SB8 | 1 | MDEKTHCTIELNPSFTHWKLLHHHPQGDALLDDGVRLPHHPLADEGGLDQGLGHRRGVVAERLARRDPBVLEGLVERHRGLVPRLRHGGERHAEPLVWRLPPS |
| SB9 | 1 | MDEKTHCMTGLYDGAADCTNELNKDVAPLVEGRHDLVEGLLLEHHPQGDPLVAHRQLVHHPLLGEGERHRRALVPQQEHQPHRLQPVVDLGRRRLVWRLPPS |
| SB10 | 1 | MDEKTHWHERAQELVGGILLHEDHPQRLLLEPRGPRPLRGLVHERGHQPQPLAGRVEADGGLLRDGGGELEPLVREGEDHLEPLDDELDAGPRGLVWRLPHHH |
| SB11 | 1 | MDEKTHWHERVHHLADGLEQHPQGRREPLVERHRQVPRGLVRELQHEGLPLEHPAGVHVTRLHQGDDRDVDGLVDGHGRDVRGLERSVGDGPHRLVWRLPPS |
| SB12 | 4 | MDKDPLLRELELERLVHHPQGGLLPLRGQVGHDAERLGAEVDDLRGGLLREEGHEVPLRKVQHRLQPQLEHLEPQPLGLLGRLQARLQPLAGHHEGDAGLQRVPGHQGRRLVWRLPPS |
| SB13 | 2 | MEREDPLDEQLRELREALVDHPQGGAQALHRHDGGHHVPLRKVQHRLQPQLEHLEPQPLGLLGRLQARLQPLAGHHEGDAGLQRVPGHQGRRLVWRLPPS |
| SB14 | 1 | MDEKTHRTLSVELSPNDWLGQTKACWRLVEGLHGHEPQGLVREHEVDVLPLAERVQQVVVGGLLADGVBQPGGLLHRRADRVDHPLPDHAGQVLGRLVWRLPPS |
| SB15 | 1 | MDEKTHWLEDLKGVLKDCLKDLMDFTKDCRSPRVQPQPLLHHDRGEPVTLLREAGRDLGGLGPRAPRQARPLHHGRHDLHEPLVLQDHPQGGPLVCGCHHH |
| SB16 | 1 | MDEKTHWVLQLHPQGDRLGPREGGDDVRLVGQGEGVLAEHPQRDRLVDGVPHGRALARRPHRVVEGLHHLLQRGGERLPPDGPRQLGLLGGELDRADPALVWRLPPS |
| SB17 | 2 | MDEKTHWGDLQEPLGHGVGEVPGGLVLAHHPQGDHLRLEPLGHALVDPLVQGVEFVVRPLQLDVGVQRVALVEQVAEFVGEGLDHEAGQAHGALVWRLPPS |
| SB18 | 1 | MDEKTHCAVNVNVGLITHWCHRVAHLQPLDPHPQGQREPLVQEVEDVDBGLVQDLLHGVVAGLLDPVEKLLTDWFKKFKNVSKDCNMTFYLEAVDWSGGCHHH |
| SB19 | 1 | MDEKTIGWRGGHVVBGLAGELEQLRARLEHHPQGQLRRDGVVQRLVDGVQERVERLDRDPGLGDLRLRIAHHRDHRLRLGGEHLLRDHPLBPDDHLVVGGLVWRLPPS |
| SB20 | 1 | MNEKTHCCKLNFKVNLADWLAEFHGGGQGLLGRRDGVVQRLVDGVQERVERLDRDPGLGDLRLRIAHHRDHRLRLGGEHLLRDHPLBPDDHLVVGGLVWRLPPS |

The "No." indicates the number of times each sequence was observed. The HPQ sequence is in bold type. Defined sequences at the termini are underlined. The six C-terminal residues are not shown.

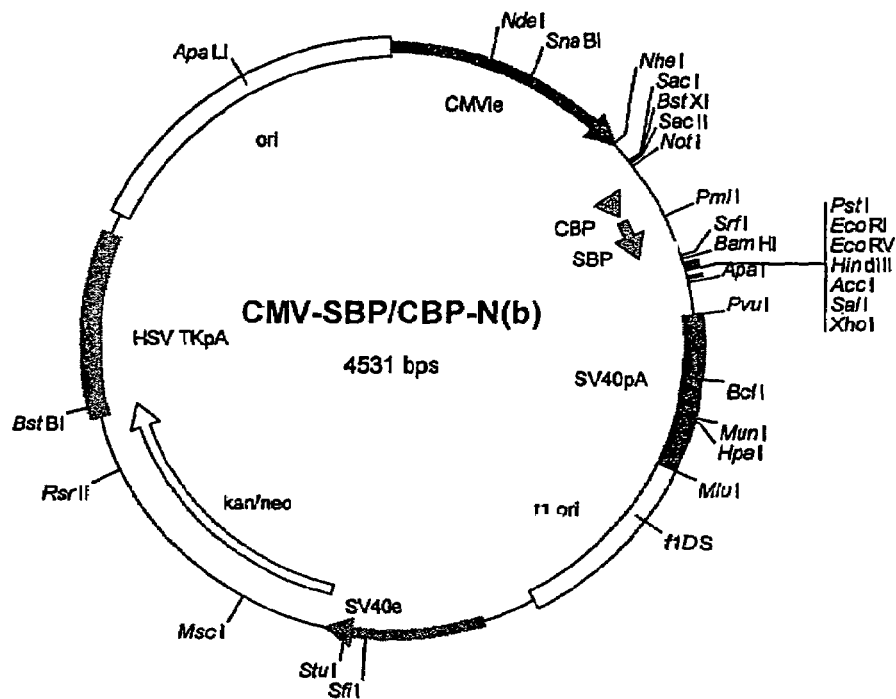

```
   1  atgcattagt tattaatagt aatcaattac ggggtcatta gttcatagcc catatatgga
  61  gttccgcgtt acataactta cggtaaatgg cccgcctggc tgaccgccca acgaccccg
 121  cccattgacg tcaataatga cgtatgttcc catagtaacg ccaataggga ctttccattg
 181  acgtcaatgg gtggagtatt tacggtaaac tgcccacttg gcagtacatc aagtgtatca
 241  tatgccaagt acgcccccta ttgacgtcaa tgacggtaaa tggcccgcct ggcattatgc
 301  ccagtacatg accttatggg actttcctac ttggcagtac atctacgtat tagtcatcgc
 361  tattaccatg gtgatgcggt tttggcagta catcaatggg cgtggatagc ggtttgactc
 421  acggggattt ccaagtctcc accccattga cgtcaatggg agtttgtttt ggcaccaaaa
 481  tcaacgggac tttccaaaat gtcgtaacaa ctccgcccca ttgacgcaaa tgggcggtag
 541  gcgtgtacgg tgggaggtct atataagcag agctggttta gtgaaccgtc agatccgcta
 601  gcgattacgc caagctcgaa attaccctc actaaaggga acaaaagctg gagctccacc
 661  gcggtggcgg ccgccaccat gaagcgacga tggaaaaaga atttcatagc cgtctcagca
 721  gccaaccgct taagaaaat ctcatcctcc ggggcacttg aagcggtag cggtaccatg
 781  gacgagaaga ccaccggctg gcggggcggc cacgtggtgg agggctggc cggcgagctg
 841  gagcagctgc gggccaggct ggagcaccac cctcagggcc agcgggagcc ctccggcggc
 901  tgcaagctgg gctgcccggg cggatccccc gggctgcagg aattcgatat caagcttatc
 961  gataccgtcg acctcgaggg ggggcccggt accttaatta attaaggtac caggtaagtg
1021  tacccaattc gccctatagt gagtcgtatt acaattcact cgatcgccct tcccaacagt
1081  tgcgcagcct gaatggcgaa tggagatcca ttttaagt gtataatgtg ttaaactact
1141  gattctaatt gtttgtgtat tttagattca cagtcccaag gctcatttca ggcccctcag
1201  tcctcacagt ctgttcatga tcataatcag ccataccaca tttgtagagg ttttacttgc
```

```
1261  tttaaaaaac ctcccacacc tccccctgaa cctgaaacat aaaatgaatg caattgttgt
1321  tgttaacttg tttattgcag cttataatgg ttacaaataa agcaatagca tcacaaattt
1381  cacaaataaa gcattttttt cactgcattc tagttgtggt ttgtccaaac tcatcaatgt
1441  atcttaacgc gtaaattgta agcgttaata ttttgttaaa attcgcgtta aatttttgtt
1501  aaatcagctc atttttaac caataggccg aaatcggcaa aatcccttat aaatcaaaag
1561  aatagaccga gatagggttg agtgttgttc cagtttggaa caagagtcca ctattaaaga
1621  acgtggactc caacgtcaaa gggcgaaaaa ccgtctatca gggcgatggc ccactacgtg
1681  aaccatcacc ctaatcaagt ttttggggt cgaggtgccg taaagcacta aatcggaacc
1741  ctaaagggag ccccgattt agagcttgac ggggaaagcc ggcgaacgtg gcgagaaagg
1801  aagggaagaa agcgaaagga gcgggcgcta gggcgctggc aagtgtagcg gtcacgctgc
1861  gcgtaaccac cacacccgcc gcgcttaatg cgccgctaca gggcgcgtca ggtggcactt
1921  ttcggggaaa tgtgcgcgga acccctattt gtttattttt ctaaatacat tcaaatatgt
1981  atccgctcat gagacaataa ccctgataaa tgcttcaata atattgaaaa aggaagaatc
2041  ctgaggcgga aagaaccagc tgtggaatgt gtgtcagtta gggtgtggaa agtccccagg
2101  ctccccagca ggcagaagta tgcaaagcat gcatctcaat tagtcagcaa ccaggtgtgg
2161  aaagtcccca ggctccccag caggcagaag tatgcaaagc atgcatctca attagtcagc
2221  aaccatagtc ccgccctaa ctccgcccat ccgcccta actccgccca gttccgccca
2281  ttctccgccc catggctgac taatttttt tatttatgca gaggccgagg ccgcctcggc
2341  ctctgagcta ttccagaagt agtgaggagg ctttttttgga ggcctaggct tttgcaaaga
2401  tcgatcaaga gacaggatga ggatcgtttc gcatgattga acaagatgga ttgcacgcag
2461  gttctccggc cgcttgggtg gagaggctat tcggctatga ctgggcacaa cagacaatcg
2521  gctgctctga tgccgccgtg ttccggctgt cagcgcaggg gcgcccggtt ctttttgtca
2581  agaccgacct gtccggtgcc ctgaatgaac tgcaagacga ggcagcgcgg ctatcgtggc
2641  tggccacgac gggcgttcct tgcgcagctg tgctcgacgt tgtcactgaa gcgggaaggg
2701  actggctgct attgggcgaa gtgccggggc aggatctcct gtcatctcac cttgctcctg
2761  ccgagaaagt atccatcatg gctgatgcaa tgcggcggct gcatacgctt gatccggcta
2821  cctgcccatt cgaccaccaa gcgaaacatc gcatcgagcg agcacgtact cggatggaag
2881  ccggtcttgt cgatcaggat gatctggacg aagaacatca ggggctcgcg ccagccgaac
2941  tgttcgccag gctcaaggcg agcatgcccg acggcgagga tctcgtcgtg acccatggcg
3001  atgcctgctt gccgaatatc atggtggaaa atggccgctt ttctggattc atcgactgtg
3061  gccgctgggg tgtggcggac cgctatcagg acatagcgtt ggctacccgt gatattgctg
3121  aagaacttgg cggcgaatgg gctgaccgct tcctcgtgct ttacggtatc gccgctcccg
3181  attcgcagcg catcgccttc tatcgccttc ttgacgagtt cttctgagcg ggactctggg
3241  gttcgaaatg accgaccaag cgacgcccaa cctgccatca cgagatttcg attccaccgc
3301  cgccttctat gaaaggttgg gcttcggaat cgttttccgg gacgccggct ggatgatcct
3361  ccagcgcggg gatctcatgc tggagttctt cgcccaccct aggggggaggc taactgaaac
3421  acggaaggag acaataccgg aaggaacccg cgctatgacg gcaataaaaa gacagaataa
3481  aacgcacggt gttgggtcgt tgttcataa acgcggggtt cggtccagg gctggcactc
3541  tgtcgatacc ccaccgagac cccattgggg ccaatacgcc cgcgtttctt ccttttcccc
3601  accccacccc caagttcgg gtgaaggccc agggctcgca gccaacgtcg gggcggcagg
3661  ccctgccata gcctcaggtt actcatatat actttagatt gatttaaaac ttcatttta
3721  atttaaaagg atctaggtga agatccttt tgataatctc atgaccaaaa tcccttaacg
3781  tgagttttcg ttccactgag cgtcagaccc cgtagaaaag atcaaaggat cttcttgaga
3841  tcctttttt ctgcgcgtaa tctgctgctt gcaaacaaaa aaccaccgc taccagcggt
3901  ggtttgtttg ccggatcaag agctaccaac tcttttccg aaggtaactg gcttcagcag
3961  agcgcagata ccaaatactg tccttctagt gtagccgtag ttaggccacc acttcaagaa
4021  ctctgtagca ccgcctacat acctcgctct gctaatcctg ttaccagtgg ctgctgccag
4081  tggcgataag tcgtgtctta ccgggttgga ctcaagacga tagttaccgg ataagcgca
4141  gcggtcgggc tgaacggggg gttcgtgcac acagcccagc ttggagcgaa cgacctacac
4201  cgaactgaga tacctacagc gtgagctatg agaaagcgcc acgcttcccg aagggagaaa
4261  ggcggacagg tatccggtaa gcggcagggt cggaacagga gagcgcacga gggagcttcc
4321  agggggaaac gcctggtatc tttatagtcc tgtcgggttt cgccacctct gacttgagcg
4381  tcgattttttg tgatgctcgt caggggggcg gagcctatgg aaaaacgcca gcaacgcggc
```

Fig. 3a-2

```
4441  cttttacgg  ttcctggcct  tttgctggcc  ttttgctcac  atgttctttc  ctgcgttatc
4501  ccctgattct  gtggataacc  gtattaccgc  c
```

Fig. 3a-3

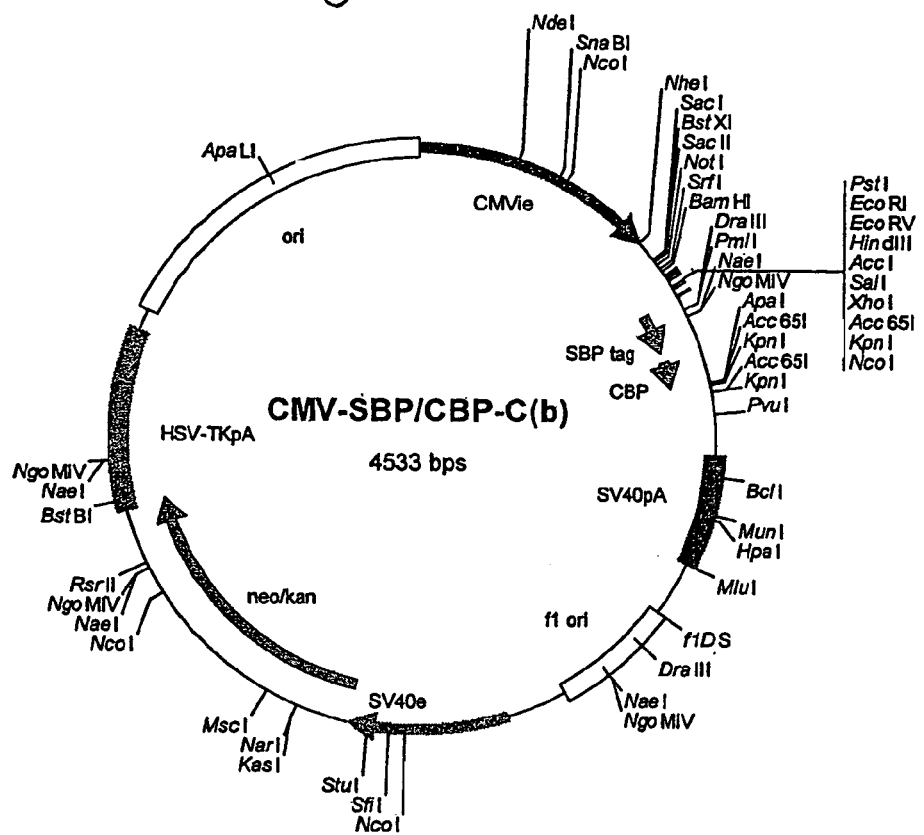

Fig. 3b-1

```
   1 atgcattagt tattaatagt aatcaattac ggggtcatta gttcatagcc catatatgga
  61 gttccgcgtt acataactta cggtaaatgg cccgcctggc tgaccgccca acgaccccg
 121 cccattgacg tcaataatga cgtatgttcc catagtaacg ccaatagggA ctttccattg
 181 acgtcaatgg gtggagtatt tacggtaaac tgcccacttg gcagtacatc aagtgtatca
 241 tatgccaagt acgccccta ttgacgtcaa tgacggtaaa tggcccgcct ggcattatgc
 301 ccagtacatg accttatggg actttcctac ttggcagtac atctacgtat tagtcatcgc
 361 tattaccatg gtgatgcggt tttggcagta catcaatggg cgtggatagc ggtttgactc
 421 acggggattt ccaagtctcc accccattga cgtcaatggg agtttgtttt ggcaccaaaa
 481 tcaacgggac tttccaaaat gtcgtaacaa ctccgcccca ttgacgcaaa tgggcggtag
 541 gcgtgtacgg tgggaggtct atataagcag agctggttta gtgaaccgtc agatccgcta
 601 gcgattacgc caagctcgaa attaaccctc actaaaggga acaaaagctg gagctccacc
 661 gcggtggcgg ccgctctagc ccgggcggat ccccgggct gcaggaattc gatatcaagc
 721 ttatcgatac cgtcgacact cgagggaagc ggtagcggta ccatggacga aagaccacc
 781 ggctggcggg gcggccacgt ggtggagggc ctggccggcg agctggagca gctgcgggcc
 841 aggctggagc accaccctca gggccagcgg gagccctccg gcggctgcaa gctgggctcc
 901 ggaaagcgac gatggaaaaa gaatttcata gccgtctcag cagccaaccg ctttaagaaa
 961 atctcatcct ccggggcact taggggcccg gtaccttaat taattaaggt accaggtaag
1021 tgtacccaat tcgccctata gtgagtcgta ttacaattca ctcgatcgcc cttcccaaca
1081 gttgcgcagc ctgaatggcg aatggagatc caatttttaa gtgtataatg tgttaaacta
1141 ctgattctaa ttgtttgtgt attttagatt cacagtccca aggctcattt caggcccctc
```

```
1201  agtcctcaca gtctgttcat gatcataatc agccatacca catttgtaga ggttttactt
1261  gctttaaaaa acctcccaca cctcccctg aacctgaaac ataaaatgaa tgcaattgtt
1321  gttgttaact tgtttattgc agcttataat ggttacaaat aaagcaatag catcacaaat
1381  ttcacaaata aagcattttt ttcactgcat tctagttgtg gtttgtccaa actcatcaat
1441  gtatcttaac gcgtaaattg taagcgttaa tattttgtta aaattcgcgt taaattttg
1501  ttaaatcagc tcattttta accaataggc cgaaatcggc aaaatccctt ataaatcaaa
1561  agaatagacc gagatagggt tgagtgttgt tccagtttgg aacaagagtc cactattaaa
1621  gaacgtggac tccaacgtca aagggcgaaa aaccgtctat cagggcgatg cccactacg
1681  tgaaccatca ccctaatcaa gttttttggg gtcgaggtgc cgtaaagcac taaatcggaa
1741  ccctaaaggg agccccgat ttagagcttg acggggaaag ccggcgaacg tggcgagaaa
1801  ggaagggaag aaagcgaaag gagcgggcgc tagggcgctg gcaagtgtag cggtcacgct
1861  gcgcgtaacc accacacccg ccgcgcttaa tgcgccgcta cagggcgcgt caggtggcac
1921  ttttcgggga aatgtgcgcg gaacccctat ttgtttattt ttctaaatac attcaaatat
1981  gtatccgctc atgagacaat aaccctgata aatgcttcaa taatattgaa aaaggaagaa
2041  tcctgaggcg gaaagaacca gctgtggaat gtgtgtcagt tagggtgtgg aaagtcccca
2101  ggctccccag caggcagaag tatgcaaagc atgcatctca attagtcagc aaccaggtgt
2161  ggaaagtccc caggctcccc agcaggcaga agtatgcaaa gcatgcatct caattagtca
2221  gcaaccatag tcccgcccct aactccgccc atcccgcccc taactccgcc cagttccgcc
2281  cattctccgc cccatggctg actaattttt tttatttatg cagaggccga ggccgcctcg
2341  gcctctgagc tattccagaa gtagtgagga ggctttttg gaggcctagg cttttgcaaa
2401  gatcgatcaa gagacaggat gaggatcgtt tgcatgatt gaacaagatg gattgcacgc
2461  aggttctccg gccgcttggg tggagaggct attcggctat gactgggcac aacagacaat
2521  cggctgctct gatgccgccg tgttccggct gtcagcgcag gggcgcccgg ttctttttgt
2581  caagaccgac ctgtccggtg ccctgaatga actgcaagac gaggcagcgc ggctatcgtg
2641  gctggccacg acgggcgttc cttgcgcagc tgtgctcgac gttgtcactg aagcgggaag
2701  ggactggctg ctattgggcg aagtgccggg gcaggatctc ctgtcatctc accttgctcc
2761  tgccgagaaa gtatccatca tggctgatgc aatgcggcgg ctgcatacgc ttgatccggc
2821  tacctgccca ttcgaccacc aagcgaaaca tcgcatcgag cgagcacgta ctcggatgga
2881  agccggtctt gtcgatcagg atgatctgga cgaagaacat caggggctcg cgccagccga
2941  actgttcgcc aggctcaagg cgagcatgcc cgacggcgag gatctcgtcg tgacccatgg
3001  cgatgcctgc ttgccgaata tcatggtgga aaatggccgc ttttctggat tcatcgactg
3061  tggccggctg ggtgtggcgg accgctatca ggacatagcg ttggctaccc gtgatattgc
3121  tgaagaactt ggcggcgaat gggctgaccg cttcctcgtg ctttacggta tcgccgctcc
3181  cgattcgcag cgcatcgcct tctatcgcct tcttgacgag ttcttctgag cgggactctg
3241  gggttcgaaa tgaccgacca agcgacgccc aacctgccat cacgagattt cgattccacc
3301  gccgccttct atgaaaggtt gggcttcgga atcgttttcc gggacgccgg ctggatgatc
3361  ctccagcgcg ggatctcat gctggagttc ttcgcccacc ctaggggag gctaactgaa
3421  acacggaagg agacaatacc ggaaggaacc cgcgctatga cggcaataaa aagacagaat
3481  aaaacgcacg gtgttgggtc gtttgttcat aaacgcgggg ttcggtccca gggctggcac
3541  tctgtcgata ccccaccgag acccattgg ggccaatacg cccgcgtttc ttccttttcc
3601  ccaccccacc cccaagttc gggtgaaggc ccagggctcg cagccaacgt cggggcggca
3661  ggccctgcca tagcctcagg ttactcatat atactttaga ttgatttaaa acttcatttt
3721  taatttaaaa ggatctaggt gaagatcctt tttgataatc tcatgaccaa aatcccttaa
3781  cgtgagtttt cgttccactg agcgtcagac cccgtagaaa agatcaaagg atcttcttga
3841  gatccttttt ttctgcgcgt aatctgctgc ttgcaaacaa aaaaaccacc gctaccagcg
3901  gtggtttgtt tgccggatca agagctacca actcttttc cgaaggtaac tggcttcagc
3961  agagcgcaga taccaaatac tgtccttcta gtgtagccgt agttaggcca ccttcaag
4021  aactctgtag caccgcctac atacctcgct ctgctaatcc tgttaccagt ggctgctgcc
4081  agtggcgata gtcgtgtct taccgggttg gactcaagac gatagttacc ggataaggcg
4141  cagcggtcgg gctgaacggg gggttcgtgc acacagccca gcttggagcg aacgacctac
4201  accgaactga gatacctaca gcgtgagcta tgagaaagcg ccacgcttcc gaagggaga
4261  aaggcggaca ggtatccggt aagcggcagg gtcggaacag gagagcgcac gagggagctt
4321  ccaggggaa acgcctggta tctttatagt cctgtcgggt ttcgccacct ctgacttgag
```

```
4381  cgtcgatttt tgtgatgctc gtcaggggggg cggagcctat ggaaaaacgc cagcaacgcg
4441  gccttttac ggttcctggc cttttgctgg ccttttgctc acatgttctt tcctgcgtta
4501  tcccctgatt ctgtggataa ccgtattacc gcc
```

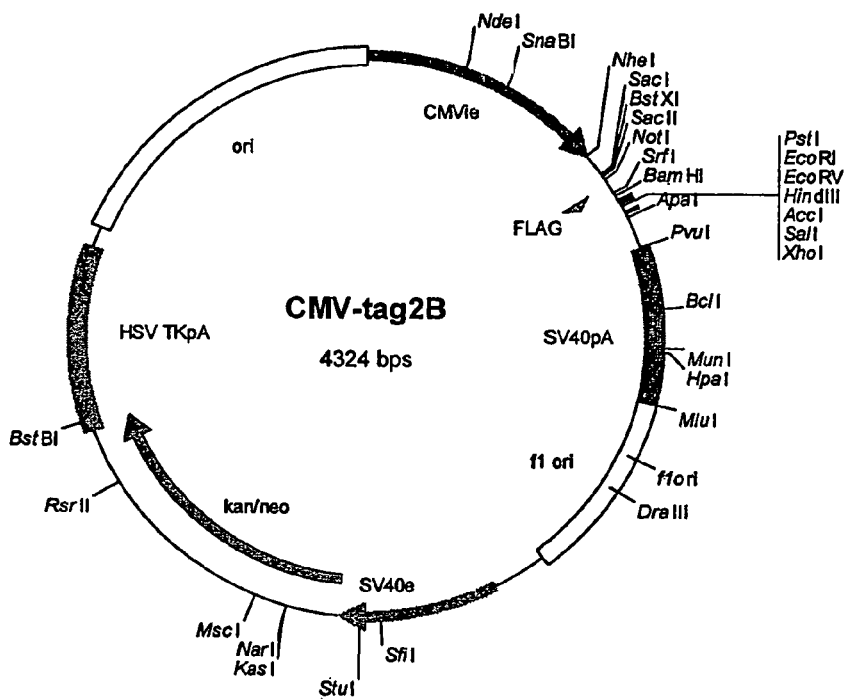

```
   1  atgcattagt tattaatagt aatcaattac ggggtcatta gttcatagcc catatatgga
  61  gttccgcgtt acataactta cggtaaatgg cccgcctggc tgaccgccca acgacccccg
 121  cccattgacg tcaataatga cgtatgttcc catagtaacg ccaatagggg ctttccattg
 181  acgtcaatgg gtggagtatt tacggtaaac tgcccacttg gcagtacatc aagtgtatca
 241  tatgccaagt acgcccccta ttgacgtcaa tgacggtaaa tggcccgcct ggcattatgc
 301  ccagtacatg accttatggg actttcctac ttggcagtac atctacgtat tagtcatcgc
 361  tattaccatg gtgatgcggt tttggcagta catcaatggg cgtggatagc ggtttgactc
 421  acggggattt ccaagtctcc accccattga cgtcaatggg agtttgtttt ggcaccaaaa
 481  tcaacgggac tttccaaaat gtcgtaacaa ctccgcccca ttgacgcaaa tgggcggtag
 541  gcgtgtacgg tgggaggtct atataagcag agctggttta gtgaaccgtc agatccgcta
 601  gcgattacgc caagctcgaa attaaccctc actaaaggga acaaaagctg gagctccacc
 661  gcggtggcgg ccgccaccat ggattacaag gatgacgacg ataagagccc gggcggatcc
 721  cccgggctgc aggaattcga tatcaagctt atcgataccg tcgacctcga ggggggggccc
 781  ggtaccttaa ttaattaagg taccaggtaa gtgtacccaa ttcgccctat agtgagtcgt
 841  attacaattc actcgatcgc ccttcccaac agttgcgcag cctgaatggc gaatggagat
 901  ccaattttta agtgtataat gtgttaaact actgattcta attgtttgtg tattttagat
 961  tcacagtccc aaggctcatt tcaggcccct cagtcctcac agtctgttca tgatcataat
1021  cagccatacc acatttgtag aggttttact tgctttaaaa aacctcccac acctcccct
1081  gaacctgaaa cataaaatga atgcaattgt tgttgttaac ttgtttattg cagcttataa
1141  tggttacaaa taaagcaata gcatcacaaa tttcacaaat aaagcatttt tttcactgca
1201  ttctagttgt ggtttgtcca aactcatcaa tgtatcttaa cgcgtaaatt gtaagcgtta
```

```
1261  atattttgtt aaaattcgcg ttaaattttt gttaaatcag ctcatttttt aaccaatagg
1321  ccgaaatcgg caaaatccct tataaatcaa aagaatagac cgagataggg ttgagtgttg
1381  ttccagtttg gaacaagagt ccactattaa agaacgtgga ctccaacgtc aaagggcgaa
1441  aaaccgtcta tcagggcgat ggcccactac gtgaaccatc accctaatca agttttttgg
1501  ggtcgaggtg ccgtaaagca ctaaatcgga accctaaagg gagccccga tttagagctt
1561  gacggggaaa gccggcgaac gtggcgagaa aggaagggaa gaaagcgaaa ggagcgggcg
1621  ctagggcgct ggcaagtgta gcggtcacgc tgcgcgtaac caccacacc gccgcgctta
1681  atgcgccgct acagggcgcg tcaggtggca cttttcgggg aaatgtgcgc ggaaccccta
1741  tttgtttatt tttctaaata cattcaaata tgtatccgct catgagacaa taaccctgat
1801  aaatgcttca ataatattga aaaggaaga atcctgaggc ggaaagaacc agctgtggaa
1861  tgtgtgtcag ttagggtgtg gaaagtcccc aggctcccca gcaggcagaa gtatgcaaag
1921  catgcatctc aattagtcag caaccaggtg tggaaagtcc caggctccc cagcaggcag
1981  aagtatgcaa agcatgcatc tcaattagtc agcaaccata gtccgcccc taactccgcc
2041  catcccgccc ctaactccgc ccagttccgc ccattctccg ccccatggct gactaatttt
2101  ttttatttat gcagaggccg aggccgcctc ggcctctgag ctattccaga agtagtgagg
2161  aggcttttt ggaggcctag gcttttgcaa agatcgatca agagacagga tgaggatcgt
2221  ttcgcatgat tgaacaagat ggattgcacg caggttctcc ggccgcttgg gtggagagc
2281  tattcggcta tgactgggca aacagacaa tcggctgctc tgatgccgcc gtgttccggc
2341  tgtcagcgca ggggcgcccg gttctttttg tcaagaccga cctgtccggt gccctgaatg
2401  aactgcaaga cgaggcagcg cggctatcgt ggctggccac gacgggcgtt ccttgcgcag
2461  ctgtgctcga cgttgtcact gaagcgggaa gggactggct gctattgggc gaagtgccgg
2521  ggcaggatct cctgtcatct caccttgctc ctgccgagaa agtatccatc atggctgatg
2581  caatgcggcg gctgcatacg cttgatccgg ctacctgccc attcgaccac caagcgaaac
2641  atcgcatcga gcgagcacgt actcggatgg aagccggtct tgtcgatcag gatgatctgg
2701  acgaagaaca tcaggggctc gcgccagccg aactgttcgc caggctcaag gcgagcatgc
2761  ccgacggcga ggatctcgtc gtgacccatg gcgatgcctg cttgccgaat atcatggtgg
2821  aaaatggccg cttttctgga ttcatcgact gtggccggct gggtgtggcg gaccgctatc
2881  aggacatagc gttggctacc cgtgatattg ctgaagaact tggcggcgaa tgggctgacc
2941  gcttcctcgt gctttacggt atcgccgctc ccgattcgca gcgcatcgcc ttctatcgcc
3001  ttcttgacga gttcttctga gcgggactct ggggttcgaa atgaccgacc aagcgacgcc
3061  caacctgcca tcacgagatt tcgattccac cgccgccttc tatgaaaggt tgggcttcgg
3121  aatcgttttc cgggacgccg gctggatgat cctccagcgc ggggatctca tgctggagtt
3181  cttcgcccac cctaggggga ggctaactga acacggaag gagacaatac cggaaggaac
3241  ccgcgctatg acggcaataa aagacagaa taaaacgcac ggtgttgggt cgtttgttca
3301  taaacgcggg gttcggtccc agggctggca ctctgtcgat accccaccga gaccccattg
3361  gggccaatac gcccgcgttt cttccttttc ccaccccac cccccaagtt cgggtgaagg
3421  cccagggctc gcagccaacg tcggggcggc aggccctgcc atagcctcag gttactcata
3481  tactttag attgatttaa aacttcattt ttaatttaaa aggatctagg tgaagatcct
3541  ttttgataat ctcatgacca aaatccctta acgtgagttt tcgttccact gagcgtcaga
3601  ccccgtagaa aagatcaaag gatcttcttg agatcctttt tttctgcgcg taatctgctg
3661  cttgcaaaca aaaaaaccac cgctaccagc ggtggtttgt ttgccggatc aagagctacc
3721  aactcttttt ccgaaggtaa ctggcttcag cagagcgcag ataccaaata ctgtccttct
3781  agtgtagccg tagttaggcc accacttcaa gaactctgta gcaccgccta catacctcgc
3841  tctgctaatc ctgttaccag tggctgctgc cagtggcgat aagtcgtgtc ttaccgggtt
3901  ggactcaaga cgatagttac cggataaggc gcagcggtcg ggctgaacgg ggggttcgtg
3961  cacacagccc agcttggagc gaacgaccta ccgaactg agatacctac agcgtgagct
4021  atgagaaagc gccacgcttc ccgaagggag aaaggcggac aggtatccgg taagcggcag
4081  ggtcggaaca ggagagcgca cgagggagct ccaggggga aacgcctggt atctttatag
4141  tcctgtcggg tttcgccacc tctgacttga gcgtcgattt tgtgatgct cgtcaggggg
4201  gcggagccta tggaaaaacg ccagcaacgc ggcctttta cggttcctgg ccttttgctg
4261  gccttttgct cacatgttct ttcctgcgtt atccctgat tctgtggata accgtattac
4321  cgcc
```

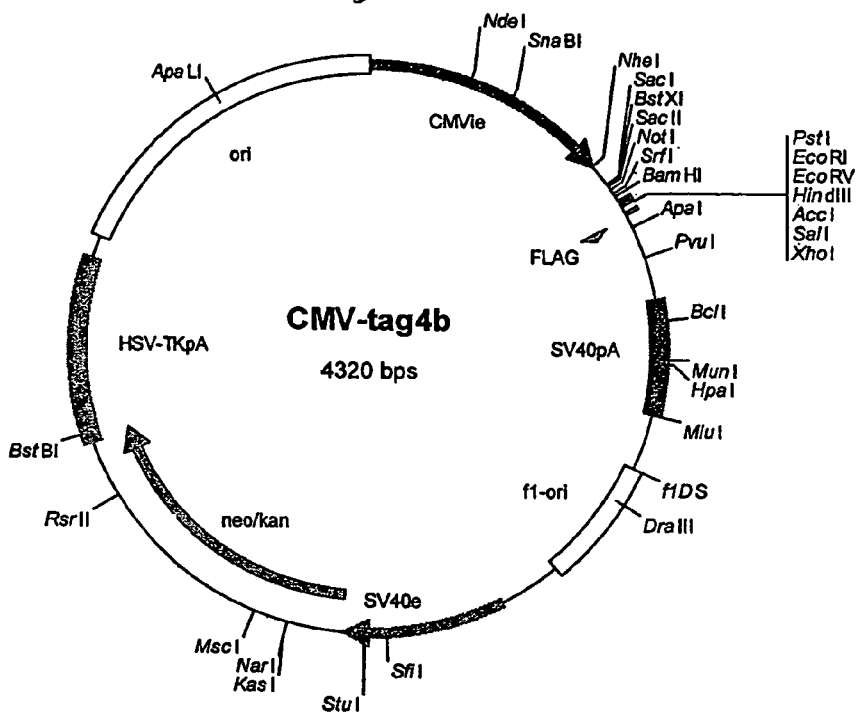

Fig. 4b-1

```
   1  atgcattagt tattaatagt aatcaattac ggggtcatta gttcatagcc catatatgga
  61  gttccgcgtt acataactta cggtaaatgg cccgcctggc tgaccgccca acgacccccg
 121  cccattgacg tcaataatga cgtatgttcc catagtaacg ccaataggga ctttccattg
 181  acgtcaatgg gtggagtatt tacggtaaac tgcccacttg gcagtacatc aagtgtatca
 241  tatgccaagt acgcccccta ttgacgtcaa tgacggtaaa tggcccgcct ggcattatgc
 301  ccagtacatg accttatggg actttcctac ttggcagtac atctacgtat tagtcatcgc
 361  tattaccatg gtgatgcggt tttggcagta catcaatggg cgtggatagc ggtttgactc
 421  acggggattt ccaagtctcc accccattga cgtcaatggg agtttgtttt ggcaccaaaa
 481  tcaacgggac tttccaaaat gtcgtaacaa ctccgcccca ttgacgcaaa tgggcggtag
 541  gcgtgtacgg tgggaggtct atataagcag agctggttta gtgaaccgtc agatccgcta
 601  gcgattacgc caagctcgaa attaaccctc actaaaggga acaaaagctg gagctccacc
 661  gcggtggcgg ccgctctagc ccgggcggat ccccgggct gcaggaattc gatatcaagc
 721  ttatcgatac cgtcgacact cgaggattac aaggatgacg acgataagta gggcccggta
 781  ccttaattaa ttaaggtacc aggtaagtgt acccaattcg ccctatagtg agtcgtatta
 841  caattcactc gatcgccctt cccaacagtt gcgcagcctg aatggcgaat ggagatccaa
 901  tttttaagtg tataatgtgt taaactactg attctaattg tttgtgtatt ttagattcac
 961  agtcccaagg ctcatttcag gcccctcagt cctcacagtc tgttcatgat cataatcagc
1021  cataccacat ttgtagaggt tttacttgct ttaaaaaacc tcccacacct ccccctgaac
1081  ctgaaacata aaatgaatgc aattgttgtt gttaacttgt ttattgcagc ttataatggt
1141  tacaaataaa gcaatagcat cacaaatttc acaaataaag cattttttc actgcattct
1201  agttgtggtt tgtccaaact catcaatgta tcttaacgcg taaattgtaa gcgttaatat
1261  tttgttaaaa ttcgcgttaa attttgtta aatcagctca ttttttaacc aataggccga
1321  aatcggcaaa atcccttata aatcaaaaga atagaccgag atagggttga gtgttgttcc
1381  agtttggaac aagagtccac tattaaagaa cgtggactcc aacgtcaaag ggcgaaaaac
1441  cgtctatcag ggcgatggcc cactacgtga accatcaccc taatcaagtt ttttggggtc
1501  gaggtgccgt aaagcactaa atcggaaccc taagggagc ccccgattta gagcttgacg
1561  gggaaagccg gcgaacgtgg cgagaaagga agggaagaaa gcgaaaggag cgggcgctag
```

```
1621  ggcgctggca  agtgtagcgg  tcacgctgcg  cgtaaccacc  acacccgccg  cgcttaatgc
1681  gccgctacag  ggcgcgtcag  gtggcacttt  tcggggaaat  gtgcgcggaa  cccctatttg
1741  tttatttttc  taaatacatt  caaatatgta  tccgctcatg  agacaataac  cctgataaat
1801  gcttcaataa  tattgaaaaa  ggaagaatcc  tgaggcggaa  agaaccagct  gtggaatgtg
1861  tgtcagttag  ggtgtggaaa  gtccccaggc  tccccagcag  gcagaagtat  gcaaagcatg
1921  catctcaatt  agtcagcaac  caggtgtgga  aagtccccag  gctccccagc  aggcagaagt
1981  atgcaaagca  tgcatctcaa  ttagtcagca  accatagtcc  cgcccctaac  tccgcccatc
2041  ccgcccctaa  ctccgcccag  ttccgcccat  tctccgcccc  atggctgact  aattttttt
2101  atttatgcag  aggccgaggc  cgcctcggcc  tctgagctat  tccagaagta  gtgaggaggc
2161  tttttggag  gcctaggctt  ttgcaaagat  cgatcaagag  acaggatgag  gatcgtttcg
2221  catgattgaa  caagatggat  tgcacgcagg  ttctccggcc  gcttgggtgg  agaggctatt
2281  cggctatgac  tgggcacaac  agacaatcgg  ctgctctgat  gccgccgtgt  tccggctgtc
2341  agcgcagggg  cgcccggttc  tttttgtcaa  gaccgacctg  tccggtgccc  tgaatgaact
2401  gcaagacgag  gcagcgcggc  tatcgtggct  ggccacgacg  ggcgttcctt  gcgcagctgt
2461  gctcgacgtt  gtcactgaag  cgggaaggga  ctggctgcta  ttgggcgaag  tgccggggca
2521  ggatctcctg  tcatctcacc  ttgctcctgc  cgagaaagta  tccatcatgg  ctgatgcaat
2581  gcggcggctg  catacgcttg  atccggctac  ctgcccattc  gaccaccaag  cgaaacatcg
2641  catcgagcga  gcacgtactc  ggatggaagc  cggtcttgtc  gatcaggatg  atctggacga
2701  agaacatcag  gggctcgcgc  cagccgaact  gttcgccagg  ctcaaggcga  gcatgcccga
2761  cggcgaggat  ctcgtcgtga  cccatggcga  tgcctgcttg  ccgaatatca  tggtggaaaa
2821  tggccgcttt  tctggattca  tcgactgtgg  ccggctgggt  gtggcggacc  gctatcagga
2881  catagcgttg  gctacccgtg  atattgctga  agaacttggc  ggcgaatggg  ctgaccgctt
2941  cctcgtgctt  tacggtatcg  ccgctcccga  ttcgcagcgc  atcgccttct  atcgccttct
3001  tgacgagttc  ttctgagcgg  gactctgggg  ttcgaaatga  ccgaccaagc  gacgcccaac
3061  ctgccatcac  gagatttcga  ttccaccgcc  gccttctatg  aaaggttggg  cttcggaatc
3121  gttttccggg  acgccggctg  gatgatcctc  cagcgcgggg  atctcatgct  ggagttcttc
3181  gcccaccct   ggggaggct   aactgaaaca  cggaaggaga  caataccgga  aggaacccgc
3241  gctatgacgg  caataaaaag  acagaataaa  acgcacggtg  ttgggtcgtt  tgttcataaa
3301  cgcggggttc  ggtcccaggg  ctggcactct  gtcgatacc   caccgagacc  ccattggggc
3361  caatacgccc  gcgtttcttc  cttttcccca  ccccaccccc  caagttcggg  tgaaggccca
3421  gggctcgcag  ccaacgtcgg  ggcggcaggc  cctgccatag  cctcaggtta  ctcatatata
3481  ctttagattg  atttaaaact  tcatttttaa  tttaaagga   tctaggtgaa  gatccttttt
3541  gataatctca  tgaccaaaat  cccttaacgt  gagttttcgt  tccactgagc  gtcagacccc
3601  gtagaaaaga  tcaaaggatc  ttcttgagat  cctttttttc  tgcgcgtaat  ctgctgcttg
3661  caaacaaaaa  aaccaccgct  accagcggtg  gtttgtttgc  cggatcaaga  gctaccaact
3721  cttttccga   aggtaactgg  cttcagcaga  gcgcagatac  caaatactgt  ccttctagtg
3781  tagccgtagt  taggccacca  cttcaagaac  tctgtagcac  cgcctacata  cctcgctctg
3841  ctaatcctgt  taccagtggc  tgctgccagt  ggcgataagt  cgtgtcttac  cgggttggac
3901  tcaagacgat  agttaccgga  taaggcgcag  cggtcgggct  gaacggggg   ttcgtgcaca
3961  cagcccagct  tggagcgaac  gacctacacc  gaactgagat  acctacagcg  tgagctatga
4021  gaaagcgcca  cgcttcccga  agggagaaag  gcggacaggt  atccggtaag  cggcagggtc
4081  ggaacaggag  agcgcacgag  ggagcttcca  gggggaaacg  cctggtatct  ttatagtcct
4141  gtcgggtttc  gccacctctg  acttgagcgt  cgatttttgt  gatgctcgtc  aggggggcgg
4201  agcctatgga  aaaacgccag  caacgcggcc  ttttacggt   tcctggcctt  tgctggcct
4261  tttgctcaca  tgttctttcc  tgcgttatcc  cctgattctg  tggataaccg  tattaccgcc
```

Fig. 4b-2

Figure 7. Menin Localization in C2C12 Myoblasts
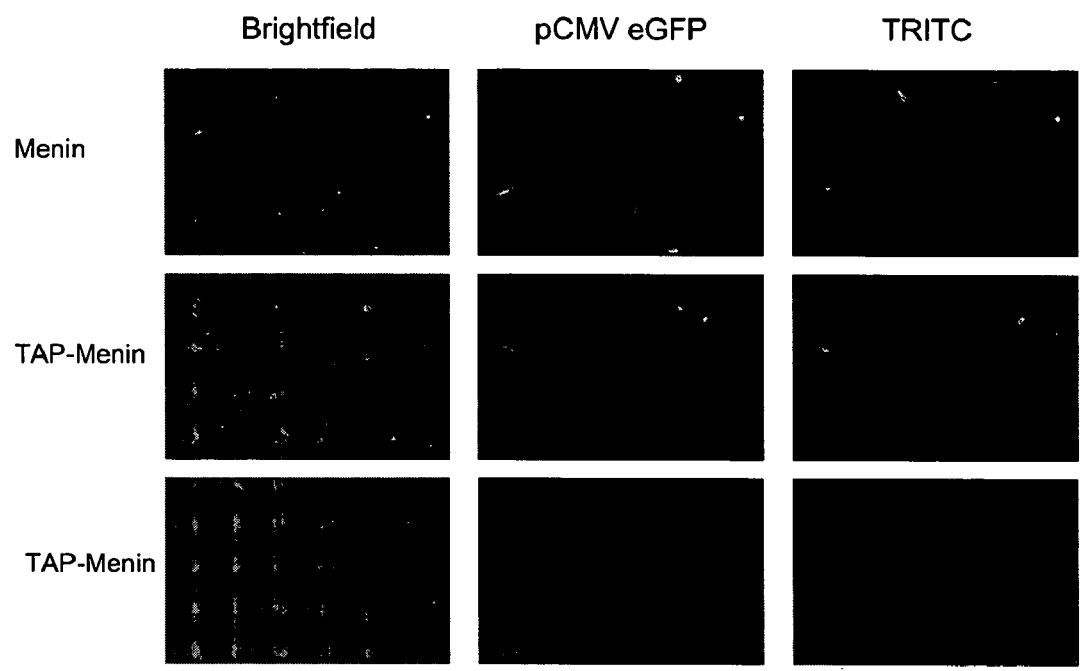
Figure 8. Tandem Affinity Purification of Mammalian Menin
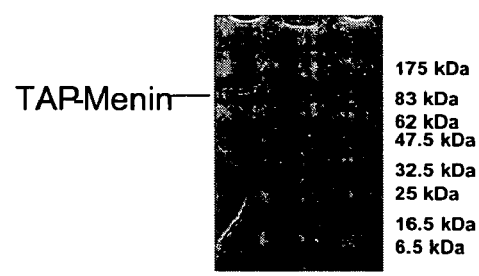

Figure 9 Identification of Menin by MALDI-TOF
Menin
Score: 82      Peptides matched: 12
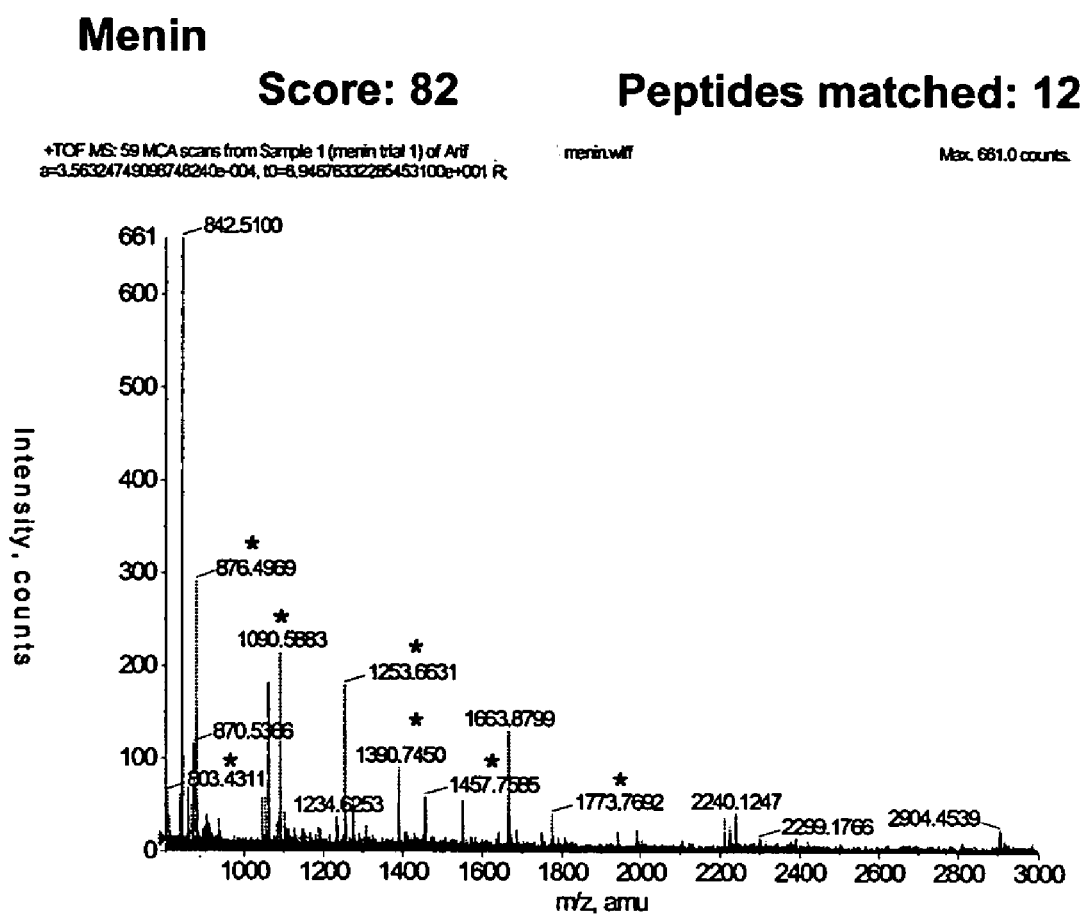
Protein scores greater than 53 are significant (p<.05)
**\* denotes peptides matching trypsin digested Menin**

SEQUENCE LISTING

<160> NUMBER OF SEQ ID NOS: 36

<210> SEQ ID NO 1
<211> LENGTH: 17
<212> TYPE: PRT
<213> ORGANISM: Bos taurus

<400> SEQUENCE: 1

Lys Ile Gln Ala Ser Phe Arg Gly His Ile Thr Arg Lys Lys Leu Lys
1               5                   10                  15

Gly

<210> SEQ ID NO 2
<211> LENGTH: 28
<212> TYPE: PRT
<213> ORGANISM: Artificial sequence
<220> FEATURE:
<223> OTHER INFORMATION: calmodulin-dependent protein kinase I (CMKI) AA
      294-318

<400> SEQUENCE: 2

Ser Glu Gln Ile Lys Lys Asn Phe Ala Lys Ser Lys Trp Lys Gln Ala
1               5                   10                  15

Phe Asn Ala Thr Ala Val Val Arg His Met Arg Lys
            20                  25

<210> SEQ ID NO 3
<211> LENGTH: 20
<212> TYPE: PRT
<213> ORGANISM: Artificial sequence
<220> FEATURE:
<223> OTHER INFORMATION: calmodulin-dependent protein kinase II (CMKII)
      AA 290-309

<400> SEQUENCE: 3

Leu Lys Lys Phe Asn Ala Arg Arg Lys Leu Lys Gly Ala Ile Leu Thr
1               5                   10                  15

Thr Met Leu Ala
            20

```
<210> SEQ ID NO 4
<211> LENGTH: 16
<212> TYPE: PRT
<213> ORGANISM: Homo sapiens

<400> SEQUENCE: 4

Trp Ile Ala Arg Leu Arg His Ile Lys Arg Leu Arg Gln Arg Ile Cys
1               5                   10                  15

<210> SEQ ID NO 5
<211> LENGTH: 260
<212> TYPE: DNA
<213> ORGANISM: Artificial sequence
<220> FEATURE:
<223> OTHER INFORMATION: DNA sequence coding CBP/SBP tandem affinity
      tags fused to the N-terminus of the bait protein

<400> SEQUENCE: 5
gcggccgcca ccatgaagcg acgatggaaa aagaatttca tagccgtctc agcagccaac    60
cgctttaaga aaatctcatc ctccggggca cttggaagcg gtagcggtac catggacgag   120
aagaccaccg gctggcgggg cggccacgtg gtggagggcc tggccggcga gctggagcag   180
ctgcgggcca ggctggagca ccaccctcag ggccagcggg agccctccgg cggctgcaag   240
ctgggcgccc gggcggatcc                                                260

<210> SEQ ID NO 6
<211> LENGTH: 78
<212> TYPE: PRT
<213> ORGANISM: Artificial sequence
<220> FEATURE:
<223> OTHER INFORMATION: CBP/SBP tandem affinity tags fused to the
      N-terminus of the bait protein

<400> SEQUENCE: 6

Met Lys Arg Arg Trp Lys Lys Asn Phe Ile Ala Val Ser Ala Ala Asn
1               5                   10                  15

Arg Phe Lys Lys Ile Ser Ser Ser Gly Ala Leu Gly Ser Gly Ser Gly
            20                  25                  30

Ser Met Asp Glu Lys Thr Thr Gly Trp Arg Gly Gly His Val Val Glu
        35                  40                  45

Gly Leu Ala Gly Glu Leu Glu Gln Leu Arg Ala Arg Leu Glu His His
    50                  55                  60

Pro Gln Gly Gln Arg Glu Pro Ser Gly Gly Cys Lys Leu Gly
65                  70                  75

<210> SEQ ID NO 7
<211> LENGTH: 254
<212> TYPE: DNA
<213> ORGANISM: Artificial sequence
<220> FEATURE:
<223> OTHER INFORMATION: DNA sequence coding CBP/SBP tandem affinity
      tags fused to the C-terminus of the bait protein

<400> SEQUENCE: 7
ctcgagggaa gcggtagcgg taccatggac gagaagacca ccggctggcg gggcggccac    60
gtggtggagg gcctggccgg cgagctggag cagctgcggg ccaggctgga gcaccaccct   120
cagggccagc gggagccctc cggcggctgc aagctgggct ccggaaagcg acgatggaaa   180
aagaatttca tagccgtctc agcagccaac cgctttaaga aaatctcatc ctccggggca   240
ctttagggcc cgac                                                     254
```

```
<210> SEQ ID NO 8
<211> LENGTH: 79
<212> TYPE: PRT
<213> ORGANISM: Artificial sequence
<220> FEATURE:
<223> OTHER INFORMATION: CBP/SBP tandem affinity tag fused to the
      C-terminus of the bait protein

<400> SEQUENCE: 8

Gly Ser Gly Ser Gly Ser Met Asp Glu Lys Thr Thr Gly Trp Arg Gly
1               5                   10                  15

Gly His Val Val Glu Gly Leu Ala Gly Glu Leu Glu Gln Leu Arg Ala
                20                  25                  30

Arg Leu Glu His His Pro Gln Gly Gln Arg Glu Pro Ser Gly Gly Cys
            35                  40                  45

Lys Leu Gly Ser Gly Lys Arg Arg Trp Lys Lys Asn Phe Ile Ala Val
        50                  55                  60

Ser Ala Ala Asn Arg Phe Lys Lys Ile Ser Ser Ser Gly Ala Leu
65                  70                  75

<210> SEQ ID NO 9
<211> LENGTH: 101
<212> TYPE: PRT
<213> ORGANISM: Artificial sequence
<220> FEATURE:
<223> OTHER INFORMATION: SBP sequence (SB1)

<400> SEQUENCE: 9

Met Asp Glu Lys Thr His Cys Thr Ile Ser Met Asn Gly Ala Val Pro
1               5                   10                  15

Leu Val Pro His His His Pro Gln Gly Asp Pro Leu Arg Leu Leu His
                20                  25                  30

Arg Pro Gln Pro Ala Leu Leu Val Arg His Pro Gln Gly Asp Leu Val
            35                  40                  45

Ala Leu Val Glu His His Glu Gly Val Asp Arg Gly Leu Val Ala Leu
        50                  55                  60

Pro Glu Leu His Ala Glu Leu Gly Glu Pro Val Gly Asp Leu Val
65                  70                  75                  80

Gln Gly Pro Val Glu Gln Val Gln Gly Val Val Asp Ala Leu Val Trp
                85                  90                  95

Arg Leu Pro Pro Ser
            100

<210> SEQ ID NO 10
<211> LENGTH: 101
<212> TYPE: PRT
<213> ORGANISM: Artificial sequence
<220> FEATURE:
<223> OTHER INFORMATION: SBP sequence (SB2)

<400> SEQUENCE: 10

Met Asp Glu Lys Thr His Cys Phe His Pro Gly Asp His Leu Val Arg
1               5                   10                  15

Leu Val Glu Glu Leu Gln Ala Leu Ala Glu Gly Leu Gln Arg Gln Gly
                20                  25                  30

Gly Arg Gln Pro His Arg Leu Pro Arg Arg Pro His Leu Gln
            35                  40                  45

Leu Leu Leu Asp Glu Ala His Pro Gln Ala Gly Pro Leu Arg Glu Arg
        50                  55                  60
```

```
Ala His Gln Val Asp Gly Arg Leu Leu Leu Gln His His Pro Gln Gly
 65                  70                  75                  80

Asp Arg Leu Leu Gln Gln Pro Gln Asp His Pro Leu Glu Leu Val Trp
                 85                  90                  95

Arg Leu Pro Pro Ser
            100

<210> SEQ ID NO 11
<211> LENGTH: 101
<212> TYPE: PRT
<213> ORGANISM: Artificial sequence
<220> FEATURE:
<223> OTHER INFORMATION: SBP sequence (SB3)

<400> SEQUENCE: 11

Met Thr Arg Arg Pro Thr Ala Ser Ser Ser Cys Val Arg His Leu
 1               5                  10                  15

Leu Leu Arg Gln Gly Glu His Gly His Gln Ala Leu Glu Asp Arg Asp
                 20                  25                  30

Lys Ala Arg His Val Arg Leu Val Glu Gly Asp Val Glu Val Leu Gly
             35                  40                  45

Gly Leu Asp Arg Leu Ala Arg Ala Arg His Glu Ala Leu His Pro Gln
         50                  55                  60

Ala Gly Leu Val His Leu Pro Leu His Gly Gly Asp Leu Gly Gly His
 65                  70                  75                  80

Leu Arg Leu Val Leu Glu Ala His Pro Gln Gly Asp Arg Leu Gly Leu
                 85                  90                  95

Ala Val His His His
            100

<210> SEQ ID NO 12
<211> LENGTH: 102
<212> TYPE: PRT
<213> ORGANISM: Artificial sequence
<220> FEATURE:
<223> OTHER INFORMATION: SBP sequence (SB4)

<400> SEQUENCE: 12

Met Asp Glu Lys Thr His Trp Gly Ile Ser Thr Trp Arg Gly Glu Pro
 1               5                  10                  15

Leu Leu His His Pro Gln Ala Gly Arg Leu Pro Leu Asp Arg Arg Arg
                 20                  25                  30

Ala Arg His Arg Arg Ile Leu Gly Ala Glu Pro Gly Gly Val Asp His
             35                  40                  45

Gly Leu Arg Leu Glu Leu Leu Asp Asp His Arg Pro Leu Val Pro Asp
         50                  55                  60

His His Pro Gln Arg Gly Pro Leu Gln Arg Gly Asp Leu Pro Gln Val
 65                  70                  75                  80

Val Pro Leu Val Arg Leu Arg His Ala His Val Leu Gly Leu Gly Leu
                 85                  90                  95

Ala Ala Ala Thr Ile Thr
            100

<210> SEQ ID NO 13
<211> LENGTH: 102
<212> TYPE: PRT
<213> ORGANISM: Artificial sequence
<220> FEATURE:
<223> OTHER INFORMATION: SBP sequence (SB5)
```

<400> SEQUENCE: 13

Met Asp Glu Lys Thr His Trp Val Asn Val Tyr His Pro Gln Gly Asp
1               5                   10                  15

Leu Leu Val Arg Gly His Gly His Asp Val Glu Ala Leu His Asp Gln
            20                  25                  30

Gly Leu His Gln Leu Asp Leu Leu Val Gly Pro Pro Glu Val Val
        35                  40                  45

Arg Ala Leu Arg Gly Glu Val Leu Gly Gly Leu Arg Arg Leu Val Pro
    50                  55                  60

Leu Asp His Pro Gln Gly Glu Ala Leu Asp Gln Ala Arg Gln Arg Pro
65                  70                  75                  80

Gln His Leu Leu Glu Leu His His Arg Ala Leu Pro Pro Ala Leu Val
                85                  90                  95

Trp Arg Leu Pro Pro Ser
            100

<210> SEQ ID NO 14
<211> LENGTH: 102
<212> TYPE: PRT
<213> ORGANISM: Artificial sequence
<220> FEATURE:
<223> OTHER INFORMATION: SBP sequence (SB6)

<400> SEQUENCE: 14

Met Asp Glu Lys Thr His Trp Leu Asn Asn Phe Glu Glu Leu Leu Ala
1               5                   10                  15

Arg Leu Asp Gly Leu Arg Glu Gly Asp His Pro Leu Val Leu Arg
            20                  25                  30

His His Pro Gln Gly Asp Gly Leu Leu Asp Gln Pro Leu Gly Arg His
        35                  40                  45

Arg Ala Leu Asp Gly Glu Val Arg Gly Asp Arg Pro Leu Asp Gln
    50                  55                  60

Gly Gly Glu Glu Asp Leu Gly Ala Leu Val Asp Asp Gly Glu Val
65                  70                  75                  80

Leu Asp Gly Leu Val His Val Gly Val His Val His Asp Pro Leu Val
                85                  90                  95

Cys Gly Cys His His His
            100

<210> SEQ ID NO 15
<211> LENGTH: 101
<212> TYPE: PRT
<213> ORGANISM: Artificial sequence
<220> FEATURE:
<223> OTHER INFORMATION: SBP sequence (SB7)

<400> SEQUENCE: 15

Met Asp Glu Lys Thr His Trp Phe Gly Thr Leu Asn Ser Phe Pro Thr
1               5                   10                  15

His Trp Met Ser Ala Val Gly Asn Gly Lys Ile Asp Cys Ser Phe Asn
            20                  25                  30

Met Asn Leu Ser Leu Asn His Trp Leu Ser Ser Gly His Pro Asp Gly
        35                  40                  45

Ala Leu Asp Asp Gln Leu His Pro Gln Gly Asp Ala Leu Val Gly Arg
    50                  55                  60

Asp Asp Gly Val Val Gln Ala Leu Arg Leu Glu Gly Gln His Gln His
65                  70                  75                  80

```
Arg Arg Leu Ala Gln Arg Arg Ala Asp Arg His Arg Gln Leu Val Trp
                85                  90                  95

Arg Leu Pro Pro Ser
            100

<210> SEQ ID NO 16
<211> LENGTH: 102
<212> TYPE: PRT
<213> ORGANISM: Artificial sequence
<220> FEATURE:
<223> OTHER INFORMATION: SBP sequence (SB8)

<400> SEQUENCE: 16

Met Asp Glu Lys Thr His Cys Thr Ile Glu Leu Asn Phe Ser Phe Thr
1               5                   10                  15

His Trp Lys Leu His His Pro Gln Gly Asp Ala Leu Leu Asp Asp
            20                  25                  30

Gly Val Arg Pro His His Pro Leu Ala Asp Glu Gly Gly Gly Leu Asp
        35                  40                  45

Gln Gly Leu Gly His Arg Arg Gly Val Val Ala Glu Arg Leu Ala Arg
    50                  55                  60

Arg Asp Pro Glu Val Leu Glu Gly Leu Val Glu Arg His Arg Gly Leu
65                  70                  75                  80

Val Pro Arg Leu Arg His Gly Gly Glu Arg His Ala Glu Pro Leu Val
                85                  90                  95

Trp Arg Leu Pro Pro Ser
            100

<210> SEQ ID NO 17
<211> LENGTH: 102
<212> TYPE: PRT
<213> ORGANISM: Artificial sequence
<220> FEATURE:
<223> OTHER INFORMATION: SBP sequence (SB9)

<400> SEQUENCE: 17

Met Asp Glu Lys Thr His Cys Asn Thr Gly Leu Tyr Asp Gly Ala Ala
1               5                   10                  15

Asp Cys Phe Asn Glu Leu Asn Lys Asp Val Ala Pro Leu Val Glu Gly
            20                  25                  30

Arg His Asp Leu Val Glu Gly Leu Leu Leu Glu Arg His Pro Gln Gly
        35                  40                  45

Asp Pro Leu Val Ala His Arg Gln Leu Val His Pro Leu Leu Gly
    50                  55                  60

Arg Gly Glu Arg His Arg Arg Ala Leu Val Pro Gln Gln Glu His Gln
65                  70                  75                  80

Pro His Arg Leu Gln Pro Val Val Asp Leu Gly Arg Arg Leu Val
                85                  90                  95

Trp Arg Leu Pro Pro Ser
            100

<210> SEQ ID NO 18
<211> LENGTH: 103
<212> TYPE: PRT
<213> ORGANISM: Artificial sequence
<220> FEATURE:
<223> OTHER INFORMATION: SBP sequence (SB10)

<400> SEQUENCE: 18

Met Asp Glu Lys Thr His Trp His Glu Arg Ala Gln Glu Leu Val Gly
```

```
                1               5                  10                 15
Gly Leu Leu Leu His Asp His Pro Gln Arg Leu Leu Glu Pro Arg
                20                 25                 30

Gly Pro Arg Pro Leu Arg Gly Leu Val His Glu Arg Gly His Gln Pro
                35                 40                 45

Gln Pro Leu Ala Gly Arg Val Glu Glu Ala Asp Gly Leu Leu Arg
        50                 55                 60

Asp Gly Gly Gly Glu Leu Glu Pro Leu Val Arg Gly Gly Asp His
65                  70                 75                 80

Leu Glu Pro Leu Asp Asp Glu Leu Asp Ala Gly Pro Arg Gly Leu Val
                85                 90                 95

Trp Arg Leu Pro His His His
                100

<210> SEQ ID NO 19
<211> LENGTH: 102
<212> TYPE: PRT
<213> ORGANISM: Artificial sequence
<220> FEATURE:
<223> OTHER INFORMATION: SBP sequence (SB11)

<400> SEQUENCE: 19

Met Asp Glu Lys Thr His Trp His Glu Arg Val His His Leu Ala Asp
1               5                  10                 15

Gly Leu Glu Gln His Pro Gln Gly Gln Arg Arg Pro Leu Val Glu Arg
                20                 25                 30

His Arg Gln Val Pro Arg Gly Leu Val Arg Glu Leu Gln His Glu Gly
                35                 40                 45

Leu Pro Leu Glu His Pro Ala Gly Val His Val Ile Arg Leu His Gln
        50                 55                 60

Gly Asp Asp Arg Asp Val Asp Gly Leu Val Asp Gly His Gly Arg Asp
65                  70                 75                 80

Val Arg Gly Leu Glu Arg Glu Val Gly Asp Gly Pro His Arg Leu Val
                85                 90                 95

Trp Arg Leu Pro Pro Ser
                100

<210> SEQ ID NO 20
<211> LENGTH: 101
<212> TYPE: PRT
<213> ORGANISM: Artificial sequence
<220> FEATURE:
<223> OTHER INFORMATION: SBP sequence (SB12)

<400> SEQUENCE: 20

Met Asp Lys Asp Pro Leu Leu Glu Glu Leu Glu Gly Leu Arg Glu Arg
1               5                  10                 15

Leu Val His His Pro Gln Gly Gly Leu Leu Pro Leu Arg Gly Gln Val
                20                 25                 30

Gly His Asp Ala Glu Arg Leu Gly Ala Glu Val Asp Asp Leu Arg Gly
                35                 40                 45

Gly Leu Leu Asp Glu Pro Gln Arg Ala Val Ala Gly Leu His His Val
        50                 55                 60

Pro His Arg Val Gly Gln Arg Leu Val His Glu Val Arg Glu Leu Asp
65                  70                 75                 80

Glu Gly Leu Leu Asp Gln Arg Asp Asp Leu Arg Gln Arg Leu Val Trp
                85                 90                 95
```

```
Arg Leu Pro Pro Ser
            100

<210> SEQ ID NO 21
<211> LENGTH: 102
<212> TYPE: PRT
<213> ORGANISM: Artificial sequence
<220> FEATURE:
<223> OTHER INFORMATION: SBP sequence (SB13)

<400> SEQUENCE: 21

Met Glu Arg Glu Asp Pro Leu Asp Glu Gln Leu Arg Glu Leu Arg Glu
1               5                   10                  15

Ala Leu Val Asp His Pro Gln Gly Gly Ala Gln Ala Leu His Arg His
            20                  25                  30

Asp Gly Gly Glu His Val Pro Leu Arg Arg Val Gln His Arg Leu Gln
        35                  40                  45

Pro Gly Leu Gln His His Leu Glu Pro Gln Pro Leu Gly Leu Leu Gly
    50                  55                  60

Glu Leu Gln Ala Arg Leu Gln Pro Leu Ala Gly Glu His Glu Gly Asp
65                  70                  75                  80

Gly Ala Gly Leu Gln Arg Val Pro Gly His Gln Gly Arg Arg Leu Val
                85                  90                  95

Trp Arg Leu Pro Pro Ser
            100

<210> SEQ ID NO 22
<211> LENGTH: 101
<212> TYPE: PRT
<213> ORGANISM: Artificial sequence
<220> FEATURE:
<223> OTHER INFORMATION: SBP sequence (SB14)

<400> SEQUENCE: 22

Met Asp Glu Lys Thr His Arg Thr Leu Ser Val Ser Leu Ser Phe Asn
1               5                   10                  15

Asp Trp Leu Gly Gln Thr Lys Ala Cys Trp Arg Leu Val Glu Gly Leu
            20                  25                  30

His Gly His Pro Gln Gly Leu Val Arg Glu His Glu Val Asp Val Leu
        35                  40                  45

Pro Leu Ala Glu Glu Val Gln Gln Val Val Gly Gly Leu Ala Asp Gly
    50                  55                  60

Val Glu Gln Pro Gly Gly Gly Leu Leu His Arg Ala Gln Arg Val Asp
65                  70                  75                  80

His Pro Leu Pro Asp His Ala Gly Gln Val Leu Gly Arg Leu Val Trp
                85                  90                  95

Arg Leu Pro Pro Ser
            100

<210> SEQ ID NO 23
<211> LENGTH: 101
<212> TYPE: PRT
<213> ORGANISM: Artificial sequence
<220> FEATURE:
<223> OTHER INFORMATION: SBP sequence (SB15)

<400> SEQUENCE: 23

Met Asp Glu Lys Thr His Trp Leu Glu Asp Leu Lys Gly Val Leu Lys
1               5                   10                  15

Asp Cys Leu Lys Asp Leu Met Asp Phe Thr Lys Asp Cys Arg Ser Pro
```

```
                20              25                  30
Arg Val Gln Pro Gln Pro Leu Leu His His Asp Arg Gly Glu Pro Val
            35                  40                  45
Pro Leu Leu Arg Glu Ala Gly Arg Asp Leu Gly Gly Leu Gly Pro Arg
        50                  55                  60
Ala Pro Arg Gln Ala Arg Pro Leu His His Gly Arg His Asp Leu His
65                  70                  75                  80
Glu Pro Leu Val Leu Gln Asp His Pro Gln Gly Gly Pro Leu Val Cys
                85                  90                  95
Gly Cys His His His
            100

<210> SEQ ID NO 24
<211> LENGTH: 102
<212> TYPE: PRT
<213> ORGANISM: Artificial sequence
<220> FEATURE:
<223> OTHER INFORMATION: SBP sequence (SB16)

<400> SEQUENCE: 24

Met Asp Glu Lys Thr His Trp Val Leu Gln Leu His Pro Gln Gly Asp
1               5                   10                  15
Arg Leu Gly Pro Arg His Gly Gly Asp Asp Val Arg Leu Val Gly Gln
            20                  25                  30
Gly Glu Gly Val Leu Glu Gly Leu Asp Gly Arg Pro Arg Arg Arg Arg
        35                  40                  45
His Arg Leu Pro Arg Glu Asp Glu His Arg Val Arg Ala Leu Val Asp
    50                  55                  60
Gln Val Arg Asp Leu Ala Glu Arg Leu Val Glu Glu Val Asp Gly Gly
65                  70                  75                  80
Val Glu Ala Leu Arg His Leu Gly Leu Pro Gln Asp Glu Pro Arg Ser
                85                  90                  95
Gly Gly Cys His His His
            100

<210> SEQ ID NO 25
<211> LENGTH: 102
<212> TYPE: PRT
<213> ORGANISM: Artificial sequence
<220> FEATURE:
<223> OTHER INFORMATION: SBP sequence (SB17)

<400> SEQUENCE: 25

Met Asp Glu Lys Thr His Trp Val Gly Asp Leu Gln Glu Pro Leu Gly
1               5                   10                  15
Pro Leu His Gly Gly Val Gly Glu Val Pro Gly Gly Leu Val Leu Arg
            20                  25                  30
His His Pro Gln Arg Asp Arg Leu Val Asp Gly Val Gly Pro His Gly
        35                  40                  45
Arg Ala Leu Ala Arg Arg Pro His Arg Val Val Glu Gly Leu His His
    50                  55                  60
Leu Leu Gln Arg Gly Gly Glu Arg Leu Pro Pro Asp Gly Pro Arg Gln
65                  70                  75                  80
Leu Gly Leu Leu Gly Gly Glu Leu Asp Arg Ala Asp Pro Ala Leu Val
                85                  90                  95
Trp Arg Leu Pro Pro Ser
            100
```

<210> SEQ ID NO 26
<211> LENGTH: 101
<212> TYPE: PRT
<213> ORGANISM: Artificial sequence
<220> FEATURE:
<223> OTHER INFORMATION: SBP sequence (SB18)

<400> SEQUENCE: 26

Met Asp Glu Lys Thr His Cys Ala Val Asn Val Asn Val Gly Leu Thr
1               5                   10                  15

His Trp Cys His Arg Val Ala His Leu Gln Pro Leu Asp Pro His Pro
            20                  25                  30

Gln Gly Asp His Leu Arg Leu Glu Pro Leu Gly His Ala Leu Val Asp
        35                  40                  45

Pro Leu Val Gln Gly Val Glu Val Val Arg Pro Leu Gln Leu Asp
    50                  55                  60

Val Gly Val Gln Arg Val Ala Leu Val Glu Gln Val Ala Glu Val Gly
65                  70                  75                  80

Glu Gly Leu Asp His Glu Ala Gly Gln Ala His Gly Ala Leu Val Trp
            85                  90                  95

Arg Leu Pro Pro Ser
            100

<210> SEQ ID NO 27
<211> LENGTH: 101
<212> TYPE: PRT
<213> ORGANISM: Artificial sequence
<220> FEATURE:
<223> OTHER INFORMATION: SBP sequence (SB19)

<400> SEQUENCE: 27

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro Leu Val Gln Glu Val Glu Asp Val Asp Glu
        35                  40                  45

Gly Leu Val Gln Asp Leu His Gly Val Val Ala Gly Leu Leu Asp Pro
    50                  55                  60

Val Glu Lys Leu Leu Thr Asp Trp Phe Lys Lys Phe Lys Asn Val Ser
65                  70                  75                  80

Lys Asp Cys Lys Met Thr Phe Tyr Leu Glu Met Tyr Asp Trp Ser Gly
            85                  90                  95

Gly Cys His His His
            100

<210> SEQ ID NO 28
<211> LENGTH: 102
<212> TYPE: PRT
<213> ORGANISM: Artificial sequence
<220> FEATURE:
<223> OTHER INFORMATION: SBP sequence (SB20)

<400> SEQUENCE: 28

Met Asn Glu Lys Thr His Cys Lys Leu Asn Phe Lys Val Asn Ile Ala
1               5                   10                  15

Asp Trp Leu Ala Glu Phe His Gly Gly Gln Gly Leu Leu Gly Arg
            20                  25                  30

Arg Asp Gly Val Val Gln Arg Leu Val Asp Gly Val Gln Glu Arg Val

```
                35                   40                  45
Glu Arg Leu Asp Arg Asp Pro Gly Leu Gly Asp Leu Arg Leu Glu Leu
 50                  55                  60

His His Arg Asp His Arg Leu Arg Leu Gly Gly Glu His Leu Leu Arg
 65                  70                  75                  80

Asp His Pro Leu Glu Pro Asp Asp His Leu Val Val Gly Gly Leu Val
                 85                  90                  95

Trp Arg Leu Pro Pro Ser
            100

<210> SEQ ID NO 29
<211> LENGTH: 4531
<212> TYPE: DNA
<213> ORGANISM: Artificial sequence
<220> FEATURE:
<223> OTHER INFORMATION: Expression vector comprising nucleic acids
      encoding CBP and SBP affinity tags

<400> SEQUENCE: 29
atgcattagt tattaatagt aatcaattac ggggtcatta gttcatagcc catatatgga    60
gttccgcgtt acataactta cggtaaatgg cccgcctggc tgaccgccca acgacccccg   120
cccattgacg tcaataatga cgtatgttcc catagtaacg ccaatagggg ctttccattg   180
acgtcaatgg gtggagtatt tacggtaaac tgcccacttg gcagtacatc aagtgtatca   240
tatgccaagt acgccccta ttgacgtcaa tgacggtaaa tggcccgcct ggcattatgc   300
ccagtacatg accttatggg actttcctac ttggcagtac atctacgtat tagtcatcgc   360
tattaccatg gtgatgcggt tttggcagta catcaatggg cgtggatagc ggtttgactc   420
acggggattt ccaagtctcc accccattga cgtcaatggg agtttgtttt ggcaccaaaa   480
tcaacgggac tttccaaaat gtcgtaacaa ctccgcccca ttgacgcaaa tgggcggtag   540
gcgtgtacgg tgggaggtct atataagcag agctggttta gtgaaccgtc agatccgcta   600
gcgattacgc caagctcgaa attaaccctc actaaaggga acaaaagctg gagctccacc   660
gcggtggcgg ccgccaccat gaagcgacga tggaaaaaga atttcatagc cgtctcagca   720
gccaaccgct ttaagaaaat ctcatcctcc gggcacttg aagcggtag cggtaccatg   780
gacgagaaga ccaccggctg gcggggcggc cacgtggtgg agggcctggc cggcgagctg   840
gagcagctgc gggccaggct ggagcaccac cctcagggcc agcgggagcc ctccggcggc   900
tgcaagctgg gctgcccggg cggatccccc gggctgcagg aattcgatat caagcttatc   960
gataccgtcg acctcgaggg ggggcccggt accttaatta attaaggtac aggtaagtg   1020
tacccaattc gccctatagt gagtcgtatt acaattcact cgatcgccct tcccaacagt  1080
tgcgcagcct gaatggcgaa tggagatcca atttttaagt gtataatgtg ttaaactact  1140
gattctaatt gtttgtgtat tttagattca cagtcccaag gctcatttca ggcccctcag  1200
tcctcacagt ctgttcatga tcataatcag ccataccaca tttgtagagg ttttacttgc  1260
tttaaaaaac ctcccacacc tcccctgaa cctgaaacat aaaatgaatg caattgttgt  1320
tgttaacttg tttattgcag cttataatgg ttacaaataa agcaatagca tcacaaattt  1380
cacaaataaa gcatttttt cactgcattc tagttgtggt ttgtccaaac tcatcaatgt  1440
atcttaacgc gtaaattgta agcgttaata tttttgttaaa attcgcgtta aattttgtt  1500
aaatcagctc attttttaac caataggccg aaatcggcaa aatcccttat aaatcaaaag  1560
aatagaccga gatagggttg agtgttgttc cagtttggaa caagagtcca ctattaaaga  1620
```

-continued

```
acgtggactc caacgtcaaa gggcgaaaaa ccgtctatca gggcgatggc ccactacgtg   1680
aaccatcacc ctaatcaagt tttttggggt cgaggtgccg taaagcacta aatcggaacc   1740
ctaaagggag cccccgattt agagcttgac ggggaaagcc ggcgaacgtg gcgagaaagg   1800
aagggaagaa agcgaaagga gcgggcgcta gggcgctggc aagtgtagcg gtcacgctgc   1860
gcgtaaccac cacacccgcc gcgcttaatg cgccgctaca gggcgcgtca ggtggcactt   1920
ttcggggaaa tgtgcgcgga accctatttt gtttattttt ctaaatacat tcaaatatgt   1980
atccgctcat gagacaataa ccctgataaa tgcttcaata atattgaaaa aggaagaatc   2040
ctgaggcgga agaaccagc tgtggaatgt gtgtcagtta gggtgtggaa agtccccagg   2100
ctccccagca ggcagaagta tgcaaagcat gcatctcaat tagtcagcaa ccaggtgtgg   2160
aaagtcccca ggctccccag caggcagaag tatgcaaagc atgcatctca attagtcagc   2220
aaccatagtc ccgcccctaa ctccgcccat cccgccccta actccgccca gttccgccca   2280
ttctccgccc catggctgac taattttttt tatttatgca gaggccgagg ccgcctcggc   2340
ctctgagcta ttccagaagt agtgaggagg ctttttttgga ggcctaggct tttgcaaaga   2400
tcgatcaaga gacaggatga ggatcgtttc gcatgattga acaagatgga ttgcacgcag   2460
gttctccggc cgcttgggtg gagaggctat tcggctatga ctgggcacaa cagacaatcg   2520
gctgctctga tgccgccgtg ttccggctgt cagcgcaggg gcgcccggtt cttttttgtca   2580 agaccgacct gtccggtgcc ctgaatgaac tgcaagacga ggcagcgcgg ctatcgtggc   2640
tggccacgac gggcgttcct tgcgcagctg tgctcgacgt tgtcactgaa gcgggaaggg   2700
actggctgct attgggcgaa gtgccggggc aggatctcct gtcatctcac cttgctcctg   2760
ccgagaaagt atccatcatg gctgatgcaa tgcggcggct gcatacgctt gatccggcta   2820
cctgcccatt cgaccaccaa gcgaaacatc gcatcgagcg agcacgtact cggatggaag   2880
ccggtcttgt cgatcaggat gatctggacg aagaacatca ggggctcgcg ccagccgaac   2940
tgttcgccag gctcaaggcg agcatgcccg acggcgagga tctcgtcgtg acccatggcg   3000
atgcctgctt gccgaatatc atggtggaaa atggccgctt ttctggattc atcgactgtg   3060
gccggctggg tgtggcggac cgctatcagg acatagcgtt ggctacccgt gatattgctg   3120
aagaacttgg cggcgaatgg gctgaccgct tcctcgtgct ttacggtatc gccgctcccg   3180
attcgcagcg catcgccttc tatcgccttc ttgacgagtt cttctgagcg ggactctggg   3240
gttcgaaatg accgaccaag cgacgcccaa cctgccatca cgagatttcg attccaccgc   3300
cgccttctat gaaaggttgg gcttcggaat cgttttccgg gacgccggct ggatgatcct   3360
ccagcgcggg gatctcatgc tggagttctt cgcccaccct aggggaggc taactgaaac   3420 acggaaggag acaataccgg aaggaacccg cgctatgacg gcaataaaaa gacagaataa   3480
aacgcacggt gttgggtcgt ttgttcataa acgcggggtt cggtcccagg gctggcactc   3540
tgtcgatacc ccaccgagac cccattgggg ccaatacgcc cgcgtttctt ccttttcccc   3600
accccacccc caagttcgg gtgaaggccc agggctcgca gccaacgtcg ggcggcagg    3660 ccctgccata gcctcaggtt actcatatat actttagatt gatttaaaac ttcattttta   3720
atttaaaagg atctaggtga agatcctttt tgataatctc atgaccaaaa tcccttaacg   3780
tgagttttcg ttccactgag cgtcagaccc cgtagaaaag atcaaggat cttcttgaga    3840 tcctttttt ctgcgcgtaa tctgctgctt gcaaacaaaa aaaccaccgc taccagcggt    3900
ggtttgtttg ccggatcaag agctaccaac tctttttccg aagtaactg gcttcagcag    3960 agcgcagata ccaaatactg tccttctagt gtagccgtag ttaggccacc acttcaagaa   4020
```

-continued

```
ctctgtagca ccgcctacat acctcgctct gctaatcctg ttaccagtgg ctgctgccag    4080
tggcgataag tcgtgtctta ccgggttgga ctcaagacga tagttaccgg ataaggcgca    4140
gcggtcgggc tgaacggggg gttcgtgcac acagcccagc ttggagcgaa cgacctacac    4200
cgaactgaga tacctacagc gtgagctatg agaaagcgcc acgcttcccg aagggagaaa    4260
ggcggacagg tatccggtaa gcggcagggt cggaacagga gagcgcacga gggagcttcc    4320
agggggaaac gcctggtatc tttatagtcc tgtcgggttt cgccacctct gacttgagcg    4380
tcgatttttg tgatgctcgt caggggggcg gagcctatgg aaaaacgcca gcaacgcggc    4440 cttttttacgg ttcctggcct tttgctggcc ttttgctcac atgttctttc ctgcgttatc    4500
ccctgattct gtggataacc gtattaccgc c                                   4531
```

<210> SEQ ID NO 30
<211> LENGTH: 4533
<212> TYPE: DNA
<213> ORGANISM: Artificial sequence
<220> FEATURE:
<223> OTHER INFORMATION: Expression vector comprising nucleic acids encoding CBP and SBP affinity tags

<400> SEQUENCE: 30

```
atgcattagt tattaatagt aatcaattac ggggtcatta gttcatagcc catatatgga     60
gttccgcgtt acataactta cggtaaatgg cccgcctggc tgaccgccca cgacccccg     120 cccattgacg tcaataatga cgtatgttcc catagtaacg ccaataggga ctttccattg    180
acgtcaatgg gtggagtatt tacggtaaac tgcccacttg gcagtacatc aagtgtatca    240
tatgccaagt acgccccta ttgacgtcaa tgacggtaaa tggcccgcct ggcattatgc    300
ccagtacatg accttatggg actttcctac ttggcagtac atctacgtat tagtcatcgc    360
tattaccatg gtgatgcggt tttggcagta catcaatggg cgtggatagc ggtttgactc    420
acggggattt ccaagtctcc accccattga cgtcaatggg agtttgtttt ggcaccaaaa    480
tcaacgggac tttccaaaat gtcgtaacaa ctccgcccca ttgacgcaaa tgggcggtag    540
gcgtgtacgg tgggaggtct atataagcag agctggttta gtgaaccgtc agatccgcta    600
gcgattacgc caagctcgaa attaaccctc actaaaggga acaaaagctg gagctccacc    660
gcggtggcgg ccgctctagc ccgggcggat ccccgggct gcaggaattc gatatcaagc    720
ttatcgatac cgtcgacact cgagggaagc ggtagcggta ccatggacga aagaccacc    780 ggctggcggg gcggccacgt ggtggagggc ctggccggcg agctggagca gctgcgggcc    840
aggctggagc accacctca gggccagcgg gagccctccg gcggctgcaa gctgggctcc    900
ggaaagcgac gatggaaaaa gaatttcata gccgtctcag cagccaaccg ctttaagaaa    960
atctcatcct ccggggcact ttagggcccg gtaccttaat taattaaggt accaggtaag   1020
tgtacccaat tcgccctata gtgagtcgta ttacaattca ctcgatcgcc cttcccaaca   1080
gttgcgcagc ctgaatggcg aatggagatc aattttttaa gtgtataatg tgttaaacta   1140
ctgattctaa ttgtttgtgt attttagatt cacagtccca aggctcattt caggcccctc   1200
agtcctcaca gtctgttcat gatcataatc agccatacca catttgtaga ggttttactt   1260
gctttaaaaa acctcccaca cctccccctg aacctgaaac ataaaatgaa tgcaattgtt   1320
gttgttaact tgtttattgc agcttataat ggttacaaat aaagcaatag catcacaaat   1380
ttcacaaata aagcatttt ttcactgcat tctagttgtg gtttgtccaa actcatcaat   1440
gtatcttaac gcgtaaattg taagcgttaa tattttgtta aaattcgcgt taaatttttg   1500
```

-continued

```
ttaaatcagc tcatttttta accaataggc cgaaatcggc aaaatccctt ataaatcaaa    1560
agaatagacc gagatagggt tgagtgttgt tccagtttgg aacaagagtc cactattaaa    1620
gaacgtggac tccaacgtca aagggcgaaa aaccgtctat cagggcgatg cccactacg     1680 tgaaccatca ccctaatcaa gttttttggg gtcgaggtgc cgtaaagcac taaatcggaa    1740
ccctaaaggg agcccccgat ttagagcttg acgggggaaag ccggcgaacg tggcgagaaa   1800
ggaagggaag aaagcgaaag gagcgggcgc tagggcgctg gcaagtgtag cggtcacgct    1860
gcgcgtaacc accacacccg ccgcgcttaa tgcgccgcta cagggcgcgt caggtggcac    1920
ttttcgggga aatgtgcgcg gaaccccctat ttgtttattt ttctaaatac attcaaatat   1980
gtatccgctc atgagacaat aaccctgata aatgcttcaa taatattgaa aaaggaagaa   2040
tcctgaggcg gaaagaacca gctgtggaat gtgtgtcagt tagggtgtgg aaagtcccca   2100
ggctccccag caggcagaag tatgcaaagc atgcatctca attagtcagc aaccaggtgt   2160
ggaaagtccc caggctcccc agcaggcaga agtatgcaaa gcatgcatct caattagtca   2220
gcaaccatag tcccgcccct aactccgccc atcccgcccc taactccgcc cagttccgcc   2280
cattctccgc cccatggctg actaattttt tttatttatg cagaggccga ggccgcctcg   2340
gcctctgagc tattccagaa gtagtgagga ggcttttttg gaggcctagg cttttgcaaa   2400
gatcgatcaa gagacaggat gaggatcgtt tcgcatgatt gaacaagatg gattgcacgc   2460
aggttctccg gccgcttggg tggagaggct attcggctat gactgggcac aacagacaat   2520
cggctgctct gatgccgccg tgttccggct gtcagcgcag gggcgcccgg ttcttttttgt  2580 caagaccgac ctgtccggtg ccctgaatga actgcaagac gaggcagcgc ggctatcgtg   2640
gctggccacg acgggcgttc cttgcgcagc tgtgctcgac gttgtcactg aagcgggaag   2700
ggactggctg ctattgggcg aagtgccggg gcaggatctc ctgtcatctc accttgctcc   2760
tgccgagaaa gtatccatca tggctgatgc aatgcggcgg ctgcatacgc ttgatccggc   2820
tacctgccca ttcgaccacc aagcgaaaca tcgcatcgag cgagcacgta ctcggatgga   2880
agccggtctt gtcgatcagg atgatctgga cgaagaacat caggggctcg cgccagccga   2940
actgttcgcc aggctcaagg cgagcatgcc cgacggcgag gatctcgtcg tgacccatgg   3000
cgatgcctgc ttgccgaata tcatggtgga aaatggccgc ttttctggat tcatcgactg   3060
tggccggctg ggtgtggcgg accgctatca ggacatagcg ttggctaccc gtgatattgc   3120
tgaagaactt ggcggcgaat gggctgaccg cttcctcgtg ctttacggta tcgccgctcc   3180
cgattcgcag cgcatcgcct tctatcgcct tcttgacgag ttcttctgag cgggactctg   3240
gggttcgaaa tgaccgacca agcgacgccc aacctgccat cacgagattt cgattccacc   3300
gccgccttct atgaaaggtt gggcttcgga atcgttttcc gggacgccgg ctggatgatc   3360
ctccagcgcg ggatctcat gctggagttc ttcgcccacc ctaggggag gctaactgaa     3420 acacggaagg agacaatacc ggaaggaacc cgcgctatga cggcaataaa aagacagaat   3480
aaaacgcacg gtgttgggtc gtttgttcat aaacgcgggg ttcggtccca gggctggcac   3540
tctgtcgata ccccaccgag accccattgg ggccaatacg cccgcgtttc ttccttttcc   3600
ccaccccacc ccccaagttc gggtgaaggc ccagggctcg cagccaacgt cggggcggca   3660
ggccctgcca tagcctcagg ttactcatat atactttaga ttgatttaaa acttcatttt   3720
taatttaaaa ggatctaggt gaagatcctt tttgataatc tcatgaccaa aatcccttaa   3780
cgtgagtttt cgttccactg agcgtcagac cccgtagaaa agatcaaagg atcttcttga   3840
```

```
gatcctttt  ttctgcgcgt  aatctgctgc  ttgcaaacaa  aaaaaccacc  gctaccagcg    3900
gtggtttgtt  tgccggatca  agagctacca  actcttttc   cgaaggtaac  tggcttcagc   3960
agagcgcaga  taccaaatac  tgtccttcta  gtgtagccgt  agttaggcca  ccacttcaag   4020
aactctgtag  caccgcctac  atacctcgct  ctgctaatcc  tgttaccagt  ggctgctgcc   4080
agtggcgata  agtcgtgtct  taccggggttg gactcaagac  gatagttacc  ggataaggcg   4140
cagcggtcgg  gctgaacggg  gggttcgtgc  acacagccca  gcttggagcg  aacgacctac   4200
accgaactga  gatacctaca  gcgtgagcta  tgagaaagcg  ccacgcttcc  cgaagggaga   4260
aaggcggaca  ggtatccggt  aagcggcagg  gtcggaacag  gagagcgcac  gagggagctt   4320
ccagggggaa  acgcctggta  tctttatagt  cctgtcgggt  ttcgccacct  ctgacttgag   4380
cgtcgatttt  tgtgatgctc  gtcagggggg  cggagcctat  ggaaaaacgc  cagcaacgcg   4440
gccttttttac ggttcctggc cttttgctgg  ccttttgctc  acatgttctt  tcctgcgtta   4500
tcccctgatt  ctgtggataa  ccgtattacc  gcc                                 4533
```

<210> SEQ ID NO 31
<211> LENGTH: 4324
<212> TYPE: DNA
<213> ORGANISM: Artificial sequence
<220> FEATURE:
<223> OTHER INFORMATION: Expression vector for expression of a "target" binding partner

<400> SEQUENCE: 31

```
atgcattagt  tattaatagt  aatcaattac  ggggtcatta  gttcatagcc  catatatgga     60
gttccgcgtt  acataactta  cggtaaatgg  cccgcctggc  tgaccgccca  acgacccccg    120
cccattgacg  tcaataatga  cgtatgttcc  catagtaacg  ccaatagga   ctttccattg    180
acgtcaatgg  gtggagtatt  tacggtaaac  tgcccacttg  gcagtacatc  aagtgtatca    240
tatgccaagt  acgcccccta  ttgacgtcaa  tgacggtaaa  tggcccgcct  ggcattatgc    300
ccagtacatg  accttatggg  actttcctac  ttggcagtac  atctacgtat  agtcatcgc     360
tattaccatg  gtgatgcggt  tttggcagta  catcaatggg  cgtggatagc  ggtttgactc    420
acggggattt  ccaagtctcc  accccattga  cgtcaatggg  agtttgtttt  ggcaccaaaa    480
tcaacgggac  tttccaaaat  gtcgtaacaa  ctccgcccca  ttgacgcaaa  tgggcggtag    540
gcgtgtacgg  tgggaggtct  atataagcag  agctggttta  gtgaaccgtc  agatccgcta    600
gcgattacgc  caagctcgaa  attaaccctc  actaaaggga  acaaaagctg  gagctccacc    660
gcggtggcgg  ccgccaccat  ggattacaag  gatgacgacg  ataagagccc  gggcggatcc    720
cccgggctgc  aggaattcga  tatcaagctt  atcgataccg  tcgacctcga  ggggggccc    780
ggtaccttaa  ttaattaagg  taccaggtaa  gtgtacccaa  ttcgccctat  agtgagtcgt    840
attacaattc  actcgatcgc  ccttcccaac  agttgcgcag  cctgaatggc  gaatggagat    900
ccaattttta  agtgtataat  gtgttaaact  actgattcta  attgtttgtg  tattttagat    960
tcacagtccc  aaggctcatt  tcaggcccct  cagtcctcac  agtctgttca  tgatcataat   1020
cagccatacc  acatttgtag  aggttttact  tgctttaaaa  aacctcccac  acctcccct    1080
gaacctgaaa  cataaaatga  atgcaattgt  tgttgttaac  ttgtttattg  cagcttataa   1140
tggttacaaa  taaagcaata  gcatcacaaa  tttcacaaat  aaagcatttt  ttcactgca    1200
ttctagttgt  ggtttgtcca  aactcatcaa  tgtatcttaa  cgcgtaaatt  gtaagcgtta   1260
atattttgtt  aaaattcgcg  ttaaattttt  gttaaatcag  ctcatttttt  aaccaatagg   1320
```

```
ccgaaatcgg caaaatccct tataaatcaa agaatagac cgagataggg ttgagtgttg   1380
ttccagtttg gaacaagagt ccactattaa agaacgtgga ctccaacgtc aaagggcgaa   1440
aaaccgtcta tcagggcgat ggcccactac gtgaaccatc accctaatca agttttttgg   1500
ggtcgaggtg ccgtaaagca ctaaatcgga accctaaagg gagccccga tttagagctt    1560 gacgggaaa gccggcgaac gtggcgagaa aggaagggaa gaaagcgaaa ggagcgggcg    1620
ctagggcgct ggcaagtgta gcggtcacgc tgcgcgtaac caccacaccc gccgcgctta   1680
atgcgccgct acaggcgcg tcaggtggca cttttcgggg aaatgtgcgc ggaacccta    1740 tttgtttatt tttctaaata cattcaaata tgtatccgct catgagacaa taaccctgat   1800
aaatgcttca ataatattga aaaggaaga atcctgaggc ggaaagaacc agctgtggaa   1860
tgtgtgtcag ttagggtgtg gaaagtcccc aggctcccca gcaggcagaa gtatgcaaag   1920
catgcatctc aattagtcag caaccaggtg tggaaagtcc ccaggctccc cagcaggcag   1980
aagtatgcaa agcatgcatc tcaattagtc agcaaccata gtcccgcccc taactccgcc   2040
catcccgccc ctaactccgc ccagttccgc ccattctccg ccccatggct gactaatttt   2100
ttttatttat gcagaggccg aggccgcctc ggcctctgag ctattccaga agtagtgagg   2160
aggctttttt ggaggcctag gcttttgcaa agatcgatca agagacagga tgaggatcgt   2220
ttcgcatgat tgaacaagat ggattgcacg caggttctcc ggccgcttgg gtggagaggc   2280
tattcggcta tgactgggca acagacaa tcggctgctc tgatgccgcc gtgttccggc    2340
tgtcagcgca gggcgcccg gttcttttg tcaagaccga cctgtccggt gccctgaatg    2400
aactgcaaga cgaggcagcg cggctatcgt ggctggccac gacgggcgtt ccttgcgcag   2460
ctgtgctcga cgttgtcact gaagcgggaa gggactggct gctattgggc gaagtgccgg   2520
ggcaggatct cctgtcatct caccttgctc ctgccgagaa agtatccatc atggctgatg   2580
caatgcggcg gctgcatacg cttgatccgg ctacctgccc attcgaccac caagcgaaac   2640
atcgcatcga gcgagcacgt actcggatgg aagccggtct tgtcgatcag gatgatctgg   2700
acgaagaaca tcaggggctc gcgccagccg aactgttcgc caggctcaag gcgagcatgc   2760
ccgacggcga ggatctcgtc gtgacccatg gcgatgcctg cttgccgaat atcatggtgg   2820 aaaatgccg cttttctgga ttcatcgact gtggccggct gggtgtggcg gaccgctatc    2880
aggacatagc gttggctacc cgtgatattg ctgaagaact tggcggcgaa tgggctgacc   2940
gcttcctcgt gctttacggt atcgccgctc ccgattcgca gcgcatcgcc ttctatcgcc   3000
ttcttgacga gttcttctga gcgggactct ggggttcgaa atgaccgacc aagcgacgcc   3060
caacctgcca tcacgagatt tcgattccac cgccgccttc tatgaaaggt tgggcttcgg   3120
aatcgttttc cgggacgccg gctggatgat cctccagcgc ggggatctca tgctggagtt   3180
cttcgcccac cctagggga ggctaactga aacacggaag gagacaatac cggaaggaac     3240
ccgcgctatg acgcaataa aaagacagaa taaaacgcac ggtgttgggt cgtttgttca    3300
taaacgcggg gttcggtccc agggctggca ctctgtcgat accccaccga acccccattg    3360
gggccaatac gcccgcgttt cttccttttc cccaccccac cccccaagtt cgggtgaagg   3420
cccagggctc gcagccaacg tcgggcggc aggccctgcc atagcctcag gttactcata    3480
tatactttag attgatttaa aacttcattt ttaatttaaa aggatctagg tgaagatcct   3540
ttttgataat ctcatgacca aaatccctta acgtgagttt tcgttccact gagcgtcaga   3600
ccccgtagaa aagatcaaag gatcttcttg agatcctttt tttctgcgcg taatctgctg   3660
cttgcaaaca aaaaaaccac cgctaccagc ggtggtttgt ttgccggatc aagagctacc   3720
```

-continued

| | |
|---|---|
| aactcttttt ccgaaggtaa ctggcttcag cagagcgcag ataccaaata ctgtccttct | 3780 |
| agtgtagccg tagttaggcc accacttcaa gaactctgta gcaccgccta catacctcgc | 3840 |
| tctgctaatc ctgttaccag tggctgctgc cagtggcgat aagtcgtgtc ttaccgggtt | 3900 |
| ggactcaaga cgatagttac cggataaggc gcagcggtcg ggctgaacgg ggggttcgtg | 3960 |
| cacacagccc agcttggagc gaacgaccta caccgaactg agatacctac agcgtgagct | 4020 |
| atgagaaagc gccacgcttc ccgaagggag aaaggcggac aggtatccgg taagcggcag | 4080 |
| ggtcggaaca ggagagcgca cgagggagct tccaggggga aacgcctggt atctttatag | 4140 |
| tcctgtcggg tttcgccacc tctgacttga gcgtcgattt ttgtgatgct cgtcaggggg | 4200 |
| gcggagccta tggaaaaacg ccagcaacgc ggcctttttta cggttcctgg ccttttgctg | 4260 |
| gccttttgct cacatgttct ttcctgcgtt atcccctgat tctgtggata accgtattac | 4320 |
| cgcc | 4324 |

<210> SEQ ID NO 32
<211> LENGTH: 4320
<212> TYPE: DNA
<213> ORGANISM: Artificial sequence
<220> FEATURE:
<223> OTHER INFORMATION: Expression vector for expression of a "target" binding partner

<400> SEQUENCE: 32

| | |
|---|---|
| atgcattagt tattaatagt aatcaattac ggggtcatta gttcatagcc catatatgga | 60 |
| gttccgcgtt acataactta cggtaaatgg cccgcctggc tgaccgccca acgacccccg | 120 |
| cccattgacg tcaataatga cgtatgttcc catagtaacg ccaataggga ctttccattg | 180 |
| acgtcaatgg gtggagtatt tacggtaaac tgcccacttg gcagtacatc aagtgtatca | 240 |
| tatgccaagt acgcccccta ttgacgtcaa tgacggtaaa tggcccgcct ggcattatgc | 300 |
| ccagtacatg accttatggg actttcctac ttggcagtac atctacgtat tagtcatcgc | 360 |
| tattaccatg gtgatgcggt tttggcagta catcaatggg cgtggatagc ggtttgactc | 420 |
| acggggattt ccaagtctcc accccattga cgtcaatggg agtttgtttt ggcaccaaaa | 480 |
| tcaacgggac tttccaaaat gtcgtaacaa ctccgcccca ttgacgcaaa tgggcggtag | 540 |
| gcgtgtacgg tgggaggtct atataagcag agctggttta gtgaaccgtc agatccgcta | 600 |
| gcgattacgc caagctcgaa attaaccctc actaaaggga acaaaagctg gagctccacc | 660 |
| gcggtggcgg ccgctctagc ccgggcggat ccccgggct gcaggaattc gatatcaagc | 720 |
| ttatcgatac cgtcgacact cgaggattac aaggatgacg acgataagta gggcccggta | 780 |
| ccttaattaa ttaaggtacc aggtaagtgt acccaattcg ccctatagtg agtcgtatta | 840 |
| caattcactc gatcgccctt cccaacagtt gcgcagcctg aatggcgaat ggagatccaa | 900 |
| ttttttaagtg tataatgtgt taaactactg attctaattg tttgtgtatt ttagattcac | 960 |
| agtcccaagg ctcatttcag gcccctcagt cctcacagtc tgttcatgat cataatcagc | 1020 |
| cataccacat ttgtagaggt tttacttgct ttaaaaaacc tcccacacct ccccctgaac | 1080 |
| ctgaaacata aaatgaatgc aattgttgtt gttaacttgt ttattgcagc ttataatggt | 1140 |
| tacaaataaa gcaatagcat cacaaatttc acaaataaag catttttttc actgcattct | 1200 |
| agttgtggtt tgtccaaact catcaatgta tcttaacgcg taaattgtaa gcgttaatat | 1260 |
| tttgttaaaa ttcgcgttaa attttttgtta aatcagctca ttttttaacc aataggccga | 1320 |
| aatcggcaaa atcccttata aatcaaaaga ataggcgag atagggttga gtgttgttcc | 1380 |

```
agtttggaac aagagtccac tattaaagaa cgtggactcc aacgtcaaag ggcgaaaaac    1440
cgtctatcag ggcgatggcc cactacgtga accatcaccc taatcaagtt ttttggggtc    1500
gaggtgccgt aaagcactaa atcggaaccc taaagggagc ccccgattta gagcttgacg    1560
gggaaagccg gcgaacgtgg cgagaaagga agggaagaaa gcgaaggag cgggcgctag     1620 ggcgctggca agtgtagcgg tcacgctgcg cgtaaccacc acaccgccg cgcttaatgc     1680 gccgctacag ggcgcgtcag gtggcacttt tcggggaaat gtgcgcggaa ccctatttg     1740 tttatttttc taaatacatt caaatatgta tccgctcatg agacaataac cctgataaat    1800
gcttcaataa tattgaaaaa ggaagaatcc tgaggcggaa agaaccagct gtggaatgtg    1860
tgtcagttag ggtgtggaaa gtccccaggc tccccagcag gcagaagtat gcaaagcatg    1920
catctcaatt agtcagcaac caggtgtgga aagtccccag gctccccagc aggcagaagt    1980
atgcaaagca tgcatctcaa ttagtcagca accatagtcc cgcccctaac tccgcccatc    2040
ccgcccctaa ctccgcccag ttccgcccat tctccgcccc atggctgact aattttttt    2100 atttatgcag aggccgaggc cgcctcggcc tctgagctat tccagaagta gtgaggaggc    2160
ttttttggag gcctaggctt ttgcaaagat cgatcaagag acaggatgag gatcgtttcg    2220
catgattgaa caagatggat tgcacgcagg ttctccggcc gcttgggtgg agaggctatt    2280
cggctatgac tgggcacaac agacaatcgg ctgctctgat gccgccgtgt tccggctgtc    2340
agcgcagggg cgcccggttc ttttgtcaa gaccgacctg tccggtgccc tgaatgaact     2400
gcaagacgag gcagcgcggc tatcgtggct ggccacgacg ggcgttcctt gcgcagctgt    2460
gctcgacgtt gtcactgaag cgggaaggga ctggctgcta ttgggcgaag tgccggggca    2520
ggatctcctg tcatctcacc ttgctcctgc cgagaaagta tccatcatgg ctgatgcaat    2580
gcggcggctg catacgcttg atccggctac ctgcccattc gaccaccaag cgaaacatcg    2640
catcgagcga gcacgtactc ggatggaagc cggtcttgtc gatcaggatg atctggacga    2700
agaacatcag gggctcgcgc cagccgaact gttcgccagg ctcaaggcga gcatgcccga    2760
cggcgaggat ctcgtcgtga cccatggcga tgcctgcttg ccgaatatca tggtggaaaa    2820
tggccgcttt tctggattca tcgactgtgg ccggctgggt gtggcggacc gctatcagga    2880
catagcgttg gctacccgtg atattgctga agaacttggc ggcgaatggg ctgaccgctt    2940
cctcgtgctt tacggtatcg ccgctcccga ttcgcagcgc atcgccttct atcgccttct    3000
tgacgagttc ttctgagcgg gactctgggg ttcgaaatga ccgaccaagc gacgcccaac    3060
ctgccatcac gagatttcga ttccaccgcc gccttctatg aaaggttggg cttcggaatc    3120
gttttccggg acgccggctg gatgatcctc cagcgcgggg atctcatgct ggagttcttc    3180
gcccacccta gggggaggct aactgaaaca cggaaggaga caataccgga aggaacccgc    3240
gctatgacgc aataaaaag acagaataaa acgcacggtg ttgggtcgtt tgttcataaa     3300
cgcggggttc ggtcccaggg ctggcactct gtcgataccc caccgagacc ccattgggc     3360 caatacgccc gcgtttcttc cttttcccca ccccaccccc caagttcggg tgaaggccca    3420
gggctcgcag ccaacgtcgg ggcggcaggc cctgccatag cctcaggtta ctcatatata    3480
ctttagattg atttaaaact tcattttta tttaaaagga tctaggtgaa gatccttttt     3540
gataatctca tgaccaaaat cccttaacgt gagttttcgt tccactgagc gtcagacccc    3600
gtagaaaaga tcaaaggatc ttcttgagat cctttttttc tgcgcgtaat ctgctgcttg    3660
caaacaaaaa aaccaccgct accagcggtg gtttgtttgc cggatcaaga gctaccaact    3720
```

```
cttttttccga aggtaactgg cttcagcaga gcgcagatac caaatactgt ccttctagtg   3780
tagccgtagt taggccacca cttcaagaac tctgtagcac cgcctacata cctcgctctg   3840
ctaatcctgt taccagtggc tgctgccagt ggcgataagt cgtgtcttac cgggttggac   3900
tcaagacgat agttaccgga taaggcgcag cggtcgggct gaacggggggg ttcgtgcaca   3960 cagcccagct tggagcgaac gacctacacc gaactgagat acctacagcg tgagctatga   4020
gaaagcgcca cgcttcccga agggagaaag gcggacaggt atccggtaag cggcagggtc   4080
ggaacaggag agcgcacgag ggagcttcca gggggaaacg cctggtatct ttatagtcct   4140
gtcgggtttc gccacctctg acttgagcgt cgatttttgt gatgctcgtc aggggggcgg   4200
agcctatgga aaaacgccag caacgcggcc ttttacggt  tcctggcctt tgctggcct    4260 tttgctcaca tgttctttcc tgcgttatcc cctgattctg tggataaccg tattaccgcc   4320
```

<210> SEQ ID NO 33
<211> LENGTH: 7692
<212> TYPE: DNA
<213> ORGANISM: Artificial sequence
<220> FEATURE:
<223> OTHER INFORMATION: Shuttle vector CMV-Shuttle-cTAP
<220> FEATURE:
<221> NAME/KEY: misc_feature
<222> LOCATION: (341)..(344)
<223> OTHER INFORMATION: "n" is either G, A, T or C.
<220> FEATURE:
<221> NAME/KEY: misc_feature
<222> LOCATION: (1481)..(1484)
<223> OTHER INFORMATION: "n" is either G, A, T or C.

<400> SEQUENCE: 33

```
catcatcaat aatataccttt atttttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa nnnntaatag taatcaatta    360
cggggtcatt agttcatagc ccatatatgg agttccgcgt tacataactt acggtaaatg    420
gcccgcctgg ctgaccgccc aacgacccc  gcccattgac gtcaataatg acgtatgttc    480
ccatagtaac gccaataggg actttccatt gacgtcaatg ggtggagtat ttacggtaaa    540
ctgcccactt ggcagtacat caagtgtatc atatgccaag tacgcccct  attgacgtca    600 atgacggtaa atggcccgcc tggcattatg cccagtacat gaccttatgg actttccta    660 cttggcagta catctacgta ttagtcatcg ctattaccat ggtgatgcgg ttttggcagt    720
acatcaatgg gcgtggatag cggtttgact cacggggatt ccaagtctc  caccccattg    780 acgtcaatgg gagtttgttt tggcaccaaa atcaacggga ctttccaaaa tgtcgtaaca    840
actccgcccc attgacgcaa atgggcggta ggcgtgtacg gtgggaggtc tatataagca    900
gagctggttt agtgaaccgt cagatccgct agagatctgg taccgtcgac gcggccgctc    960
gagcctaagc ttatcgatac gcgtccgatc ggcagcaatg gacgagaaga ccaccggctg   1020
gcggggcggc cacgtggtgg agggcctggc cggcagctg  gagcagctgc gggccaggct   1080
ggagcaccac cctcagggcc agcgggagcc ctccggcggc tgcaagctgg gctccggaaa   1140
gcgacgatga aaaagaatt  tcatagccgt ctcagcagcc aaccgcttta agaaaatctc   1200
atcctccggg gcactttagg atatccgatc caccggatct agataactga tcataatcag   1260
```

-continued

| | |
|---|---|
| ccataccaca tttgtagagg ttttacttgc tttaaaaaac ctcccacacc tccccctgaa | 1320 |
| cctgaaacat aaaatgaatg caattgttgt tgttaacttg tttattgcag cttataatgg | 1380 |
| ttacaaataa agcaatagca tcacaaattt cacaaataaa gcattttttt cactgcattc | 1440 |
| tagttgtggt ttgtccaaac tcatcaatgt atcttaacgc nnnntaaggg tgggaaagaa | 1500 |
| tatataaggt gggggtctta tgtagttttg tatctgtttt gcagcagccg ccgccgccat | 1560 |
| gagcaccaac tcgtttgatg gaagcattgt gagctcatat ttgacaacgc gcatgccccc | 1620 |
| atgggccggg gtgcgtcaga atgtgatggg ctccagcatt gatggtcgcc ccgtcctgcc | 1680 |
| cgcaaactct actaccttga cctacgagac cgtgtctgga acgccgttgg agactgcagc | 1740 |
| ctccgccgcc gcttcagccg ctgcagccac cgcccgcggg attgtgactg actttgcttt | 1800 |
| cctgagcccg cttgcaagca gtgcagcttc ccgttcatcc gcccgcgatg acaagttgac | 1860 |
| ggctcttttg gcacaattgg attctttgac ccgggaactt aatgtcgttt ctcagcagct | 1920 |
| gttggatctg cgccagcagg tttctgccct gaaggcttcc tcccctccca atgcggttta | 1980 |
| aaacataaat aaaaaaccag actctgtttg gatttggatc aagcaagtgt cttgctgtct | 2040 |
| ttatttaggg gttttgcgcg cgcggtaggc ccgggaccag cggtctcggt cgttgagggt | 2100 |
| cctgtgtatt ttttccagga cgtggtaaag gtgactctgg atgttcagat acatgggcat | 2160 |
| aagcccgtct ctggggtgga ggtagcacca ctgcagagct tcatgctgcg gggtggtgtt | 2220 |
| gtagatgatc cagtcgtagc aggagcgctg ggcgtggtgc ctaaaaatgt ctttcagtag | 2280 |
| caagctgatt gccaggggca ggcccttggt gtaagtgttt acaaagcggt taagctggga | 2340 |
| tgggtgcata cgtggggata tgagatgcat cttggactgt atttttaggt tggctatgtt | 2400 |
| cccagccata tccctccggg gattcatgtt gtgcagaacc accagcacag tgtatccggt | 2460 |
| gcacttggga aatttgtcat gtagcttaga aggaaatgcg tggaagaact tggagacgcc | 2520 |
| cttgtgacct ccaagatttt ccatgcattc gtccataatg atggcaatgg gcccacgggc | 2580 |
| ggcggcctgg gcgaagatat ttctgggatc actaacgtca tagttgtgtt ccaggatgag | 2640 |
| atcgtcatag gccattttta caaagcgcgg gcggagggtg ccagactgcg gtataatggt | 2700 |
| tccatccggc ccaggggcgt agttaccctc acagatttgc atttcccacg ctttgagttc | 2760 |
| agatgggggg atcatgtcta cctgcggggc gatgaagaaa acggtttccg gggtagggga | 2820 |
| gatcagctgg gaagaaagca ggttcctgag cagctgcgac ttaccgcagc cggtgggccc | 2880 |
| gtaaatcaca cctattaccg ggtgcaactg gtagttaaga gagctgcagc tgccgtcatc | 2940 |
| cctgagcagg ggggccactt cgttaagcat gtccctgact cgcatgtttt ccctgaccaa | 3000 |
| atccgccaga aggcgctcgc cgcccagcga tagcagttct tgcaaggaag caaagttttt | 3060 |
| caacggtttg agaccgtccg ccgtaggcat gcttttgagc gtttgaccaa gcagttccag | 3120 |
| gcggtcccac agctcggtca cctgctctac ggcatctcga tccagcatat ctcctcgttt | 3180 |
| cgcgggttgg ggcggctttc gctgtacggc agtagtcggt gctcgtccag acgggccagg | 3240 |
| gtcatgtctt tccacgggcg cagggtcctc gtcagcgtag tctgggtcac ggtgaagggg | 3300 |
| tgcgctccgg gctgcgcgct ggccagggtg cgcttgaggc tggtcctgct ggtgctgaag | 3360 |
| cgctgccggt cttcgccctg cgcgtcggcc aggtagcatt tgaccatggt gtcatagtcc | 3420 |
| agcccctccg cggcgtggcc cttggcgcgc agcttgccct tggaggaggc gccgcacgag | 3480 |
| gggcagtgca gacttttgag ggcgtagagc ttgggcgcga gaaataccga ttccggggag | 3540 |
| taggcatccg cgccgcaggc cccgcagacg gtctcgcatt ccacgagcca ggtgagctct | 3600 |

```
ggccgttcgg ggtcaaaaac caggtttccc ccatgctttt tgatgcgttt cttacctctg    3660
gtttccatga gccggtgtcc acgctcggtg acgaaaaggc tgtccgtgtc cccgtataca    3720
gacttgagag ggagtttaaa cgaattcaat agcttgttgc atgggcggcg atataaaatg    3780
caaggtgctg ctcaaaaaat caggcaaagc ctcgcgcaaa aagaaagca catcgtagtc     3840 atgctcatgc agataaaggc aggtaagctc cggaaccacc acagaaaaag acaccatttt    3900
tctctcaaac atgtctgcgg gtttctgcat aaacacaaaa taaataaca aaaaaacatt     3960 taaacattag aagcctgtct tacaacagga aaaacaaccc ttataagcat aagacggact    4020
acggccatgc cggcgtgacc gtaaaaaaac tggtcaccgt gattaaaaag caccaccgac    4080
agctcctcgg tcatgtccgg agtcataatg taagactcgg taaacacatc aggttgattc    4140
atcggtcagt gctaaaaagc gaccgaaata gcccggggga atacataccc gcaggcgtag    4200
agacaacatt acagccccca taggaggtat aacaaaatta ataggagaga aaaacacata    4260
aacacctgaa aaaccctcct gcctaggcaa aatagcaccc tcccgctcca gaacaacata    4320
cagcgcttca cagcggcagc ctaacagtca gccttaccag taaaaaagaa aacctattaa    4380
aaaaacacca ctcgacacgg caccagctca atcagtcaca gtgtaaaaaa gggccaagtg    4440
cagagcgagt atatatagga ctaaaaaatg acgtaacggt taaagtccac aaaaaacacc    4500
cagaaaaccg cacgcgaacc tacgcccaga acgaaagcc aaaaaaccca caacttcctc     4560
aaatcgtcac ttccgttttc ccacgttacg taacttccca tttaagaaa actacaattc     4620 ccaacacata caagttactc cgccctaaaa cctacgtcac ccgccccgtt cccacgcccc    4680
gcgccacgtc acaaactcca cccctcatt atcatattgg cttaatcca aataaggta      4740 tattattgat gatgttaatt aacatgcatg gatccatatg cggtgtgaaa taccgcacag    4800
atgcgtaagg agaaaatacc gcatcaggcg ctcttccgct tcctcgctca ctgactcgct    4860
gcgctcggtc gttcggctgc ggcgagcggt atcagctcac tcaaaggcgg taatacggtt    4920
atccacagaa tcaggggata acgcaggaaa gaacatgtga gcaaaaggcc agcaaaaggc    4980
caggaaccgt aaaaaggccg cgttgctggc gtttttccat aggctccgcc ccctgacga    5040 gcatcacaaa aatcgacgct caagtcagag gtggcgaaac ccgacaggac tataaagata    5100
ccaggcgttt ccccctggaa gctccctcgt gcgctctcct gttccgaccc tgccgcttac    5160
cggatacctg tccgcctttc tcccttcggg aagcgtggcg ctttctcata gctcacgctg    5220
taggtatctc agttcggtgt aggtcgttcg ctccaagctg ggctgtgtgc acgaaccccc    5280
cgttcagccc gaccgctgcg ccttatccgg taactatcgt cttgagtcca acccggtaag    5340
acacgactta tcgccactgg cagcagccac tggtaacagg attagcagag cgaggtatgt    5400
aggcggtgct acagagttct tgaagtggtg gcctaactac ggctacacta aggacagt     5460 atttggtatc tgcgctctgc tgaagccagt taccttcgga aaaagagttg gtagctcttg    5520
atccggcaaa caaccaccg ctggtagcgg tggtttttt gtttgcaagc agcagattac      5580
gcgcagaaaa aaaggatctc aagaagatcc tttgatcttt tctacggggt ctgacgctca    5640
gtggaacgaa aactcacgtt aagggatttt ggtcatgaga ttatcaaaaa ggatcttcac    5700
ctagatcctt ttaaattaaa aatgaagttt taaatcaatc taagtatat atgagtaaac     5760 ttggtctgac agttaccaat gcttaatcag tgaggcacct atctcagcga tctgtctatt    5820
tcgttcatcc atagttgcct gactccccgt cgtgtagata actacgatac gggagggctt    5880
accatctggc cccagtgctg caatgatacc gcgagaccca cgctcaccgg ctccagattt    5940
atcagcaata aaccagccag ccggaagggc cgagcgcaga agtggtcctg caactttatc    6000
```

```
cgcctccatc cagtctatta attgttgccg ggaagctaga gtaagtagtt cgccagttaa    6060
tagtttgcgc aacgttgttg ccattgctgc agccatgaga ttatcaaaaa ggatcttcac    6120
ctagatcctt ttcacgtaga aagccagtcc gcagaaacgg tgctgacccc ggatgaatgt    6180
cagctactgg gctatctgga caagggaaaa cgcaagcgca agagaaagc aggtagcttg     6240 cagtgggctt acatggcgat agctagactg gcggttttta tggacagcaa gcgaaccgga    6300
attgccagct ggggcgccct ctggtaaggt tgggaagccc tgcaaagtaa actggatggc    6360
tttcttgccg ccaaggatct gatggcgcag gggatcaagc tctgatcaag agacaggatg    6420
aggatcgttt cgcatgattg aacaagatgg attgcacgca ggttctccgg ccgcttgggt    6480
ggagaggcta ttcggctatg actgggcaca acagacaatc ggctgctctg atgccgccgt    6540
gttccggctg tcagcgcagg ggcgcccggt tctttttgtc aagaccgacc tgtccggtgc    6600
cctgaatgaa ctgcaagacg aggcagcgcg gctatcgtgg ctggccacga cgggcgttcc    6660
ttgcgcagct gtgctcgacg ttgtcactga agcgggaagg gactggctgc tattgggcga    6720
agtgccgggg caggatctcc tgtcatctca ccttgctcct gccgagaaag tatccatcat    6780
ggctgatgca atgcggcggc tgcatacgct tgatccggct acctgcccat tcgaccacca    6840
agcgaaacat cgcatcgagc gagcacgtac tcggatggaa gccggtcttg tcgatcagga    6900
tgatctggac gaagagcatc aggggctcgc gccagccgaa ctgttcgcca ggctcaaggc    6960
gagcatgccc gacggcgagg atctcgtcgt gacccatggc gatgcctgct tgccgaatat    7020
catggtggaa aatggccgct tttctggatt catcgactgt ggccggctgg gtgtggcgga    7080
ccgctatcag gacatagcgt tggctacccg tgatattgct gaagagcttg gcggcgaatg    7140
ggctgaccgc ttcctcgtgc tttacggtat cgccgctccc gattcgcagc gcatcgcctt    7200
ctatcgcctt cttgacgagt tcttctgaat tttgttaaaa ttttgttaa atcagctcat    7260 tttttaacca ataggccgaa atcggcaaca tcccttataa atcaaaagaa tagaccgcga    7320
tagggttgag tgttgttcca gtttggaaca agagtccact attaaagaac gtggactcca    7380
acgtcaaagg gcgaaaaacc gtctatcagg gcgatggccc actacgtgaa ccatcaccca    7440
aatcaagttt tttgcggtcg aggtgccgta agctctaaa tcggaaccct aaagggagcc    7500
cccgatttag agcttgacgg ggaaagccgg cgaacgtggc gagaaaggaa gggaagaaag    7560
cgaaaggagc gggcgctagg gcgctggcaa gtgtagcggt cacgctgcgc gtaaccacca    7620
cacccgcgcg cttaatgcgc cgctacaggg cgcgtccatt cgccattcag gatcgaatta    7680
attcttaatt aa                                                        7692
```

<210> SEQ ID NO 34
<211> LENGTH: 7719
<212> TYPE: DNA
<213> ORGANISM: Artificial sequence
<220> FEATURE:
<223> OTHER INFORMATION: Artificial shuttle vector sequence for
      pCMV-Shuttle-nTAP
<220> FEATURE:
<221> NAME/KEY: misc_feature
<222> LOCATION: (341)..(344)
<223> OTHER INFORMATION: "n" is either G, A,T or C.
<220> FEATURE:
<221> NAME/KEY: misc_feature
<222> LOCATION: (1508)..(1511)
<223> OTHER INFORMATION: "n" is either G, A, T or C.

<400> SEQUENCE: 34

```
catcatcaat aatataccct attttggatt gaagccaata tgataatgag ggggtggagt      60
```

```
ttgtgacgtg gcgcggggcg tgggaacggg gcgggtgacg tagtagtgtg gcggaagtgt      120
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag      240
taaatttggg cgtaaccgag taagatttgg ccattttcgc gggaaaactg aataagagga      300
agtgaaatct gaataatttt gtgttactca tagcgcgtaa nnnntaatag taatcaatta      360
cggggtcatt agttcatagc ccatatatgg agttccgcgt tacataactt acggtaaatg      420
gcccgcctgg ctgaccgccc aacgaccccc gcccattgac gtcaataatg acgtatgttc      480
ccatagtaac gccaataggg actttccatt gacgtcaatg ggtggagtat ttacggtaaa      540
ctgcccactt ggcagtacat caagtgtatc atatgccaag tacgcccct attgacgtca       600 atgacggtaa atggcccgcc tggcattatg cccagtacat gaccttatgg actttccta      660 cttggcagta catctacgta ttagtcatcg ctattaccat ggtgatgcgg ttttggcagt      720
acatcaatgg gcgtggatag cggtttgact cacggggatt tccaagtctc cacccccattg     780 acgtcaatgg gagtttgttt tggcaccaaa atcaacggga ctttccaaaa tgtcgtaaca      840
actccgcccc attgacgcaa atgggcggta ggcgtgtacg gtgggaggtc tatataagca      900
gagctggttt agtgaaccgt cagatccgct agagatctgc tagcatgaag cgacgatgga      960
aaaagaattt catagccgtc tcagcagcca accgctttaa gaaaatctca tcctccgggg     1020
cacttggaag cggtagcggt accatggacg agaagaccac cggctggcgg ggcggccacg     1080
tggtggaggg cctggccggc gagctggagc agctgcgggc caggctggag caccaccctc     1140
agggccagcg ggagccctcc ggcggctgca agctgggcgc ccgggcggat ccccgggcg      1200 tcgacgcggc cgctcgagcc gaagcttatc gatacgcgtc cgatcggata tccgatccac     1260
cggatctaga taactgatca taatcagcca taccacattt gtagaggttt tacttgcttt     1320
aaaaaacctc ccacacctcc ccctgaacct gaaacataaa atgaatgcaa ttgttgttgt     1380
taacttgttt attgcagctt ataatggtta caaataaagc aatagcatca caaatttcac      1440
aaataaagca ttttttttcac tgcattctag ttgtggtttg tccaaactca tcaatgtatc     1500
ttaacgcnnn ntaagggtgg gaaagaatat ataaggtggg ggtcttatgt agttttgtat     1560
ctgttttgca gcagccgccg ccgccatgag caccaactcg tttgatggaa gcattgtgag     1620
ctcatatttg acaacgcgca tgccccccatg ggccggggtg cgtcagaatg tgatgggctc     1680
cagcattgat ggtcgccccg tcctgcccgc aaactctact accttgacct acgagaccgt     1740
gtctggaacg ccgttggaga ctgcagcctc cgccgccgct tcagccgctg cagccaccgc     1800
ccgcgggatt gtgactgact tgctttcct gagcccgctt gcaagcagtg cagcttcccg      1860
ttcatccgcc cgcgatgaca agttgacggc tcttttggca caattggatt ctttgacccg     1920
ggaacttaat gtcgtttctc agcagctgtt ggatctgcgc cagcaggttt ctgccctgaa     1980
ggcttcctcc cctcccaatg cggtttaaaa cataaataaa aaccagact ctgtttggat     2040 ttggatcaag caagtgtctt gctgtcttta tttaggggtt ttgcgcgcgc ggtaggcccg     2100
ggaccagcgg tctcggtcgt tgagggtcct gtgtattttt tccaggacgt ggtaaaggtg     2160
actctggatg ttcagataca tgggcataag cccgtctctg gggtggaggt agcaccactg     2220
cagagcttca tgctgcgggg tggtgttgta gatgatccag tcgtagcagg agcgctgggc     2280
gtggtgccta aaaatgtctt tcagtagcaa gctgattgcc aggggcaggc ccttggtgta     2340
agtgtttaca aagcggttaa gctgggatgg gtgcatacgt ggggatatga gatgcatctt     2400
```

-continued

```
ggactgtatt tttaggttgg ctatgttccc agccatatcc ctccggggat tcatgttgtg    2460
cagaaccacc agcacagtgt atccggtgca cttgggaaat tgtcatgta gcttagaagg    2520 aaatgcgtgg aagaacttgg agacgccctt gtgacctcca agattttcca tgcattcgtc    2580
cataatgatg gcaatgggcc cacgggcggc ggcctgggcg aagatatttc tgggatcact    2640
aacgtcatag ttgtgttcca ggatgagatc gtcataggcc atttttacaa agcgcgggcg    2700
gagggtgcca gactgcggta taatggttcc atccggccca ggggcgtagt taccctcaca    2760
gatttgcatt tcccacgctt tgagttcaga tggggggatc atgtctacct gcgggcgat    2820 gaagaaaacg gtttccgggg tagggagat cagctgggaa gaaagcaggt tcctgagcag    2880
ctgcgactta ccgcagccgg tgggcccgta atcacacct attaccgggt gcaactggta    2940
gttaagagag ctgcagctgc cgtcatccct gagcaggggg gccacttcgt taagcatgtc    3000
cctgactcgc atgttttccc tgaccaaatc cgccagaagg cgctcgccgc ccagcgatag    3060
cagttcttgc aaggaagcaa agttttcaa cggtttgaga ccgtccgccg taggcatgct    3120
tttgagcgtt tgaccaagca gttccaggcg gtcccacagc tcggtcacct gctctacggc    3180
atctcgatcc agcatatctc ctcgtttcgc gggttgggc ggctttcgct gtacggcagt    3240
agtcggtgct cgtccagacg ggccagggtc atgtctttcc acgggcgcag gtcctcgtc    3300 agcgtagtct gggtcacggt gaaggggtgc gctccgggct gcgcgctggc cagggtgcgc    3360
ttgaggctgg tcctgctggt gctgaagcgc tgccggtctt cgccctgcgc gtcggccagg    3420
tagcatttga ccatggtgtc atagtccagc ccctccgcgg cgtggccctt ggcgcgcagc    3480
ttgcccttgg aggaggcgcc gcacgagggg cagtgcagac ttttgagggc gtagagcttg    3540
ggcgcgagaa ataccgattc cggggagtag gcatccgcgc cgcaggcccc gcagacggtc    3600
tcgcattcca cgagccaggt gagctctggc cgttcggggt caaaaaccag gtttccccca    3660 tgcttttttga tgcgtttctt acctctggtt tccatgagcc ggtgtccacg ctcggtgacg    3720
aaaaggctgt ccgtgtcccc gtatacagac ttgagaggga gtttaaacga attcaatagc    3780
ttgttgcatg ggcggcgata taaaatgcaa ggtgctgctc aaaaaatcag gcaaagcctc    3840
gcgcaaaaaa gaaagcacat cgtagtcatg ctcatgcaga taaaggcagg taagctccgg    3900
aaccaccaca gaaaaagaca ccatttttct ctcaaacatg tctgcgggtt tctgcataaa    3960
cacaaaataa aataacaaaa aaacatttaa acattagaag cctgtcttac aacaggaaaa    4020
acaaccctta taagcataag acggactacg gccatgccgg cgtgaccgta aaaaaactgg    4080
tcaccgtgat taaaaagcac caccgacagc tcctcggtca tgtccggagt cataatgtaa    4140
gactcggtaa acacatcagg ttgattcatc ggtcagtgct aaaaagcgac cgaaatagcc    4200
cgggggaata catacccgca ggcgtagaga caacattaca gccccatag gaggtataac    4260 aaaattaata ggagagaaaa acacataaac acctgaaaaa ccctcctgcc taggcaaaat    4320
agcaccctcc cgctccagaa caacatacag cgcttcacag cggcagccta acagtcagcc    4380
ttaccagtaa aaaagaaaac ctattaaaaa aacaccactc gacacggcac cagctcaatc    4440
agtcacagtg taaaaaggg ccaagtgcag agcgagtata tataggacta aaaaatgacg    4500
taacggttaa agtccacaaa aaacacccag aaaaccgcac gcgaacctac gcccagaaac    4560
gaaagccaaa aaacccacaa cttcctcaaa tcgtcacttc cgttttccca cgttacgtaa    4620
cttcccattt taagaaaact acaattccca acacatacaa gttactccgc cctaaaacct    4680
acgtcacccg ccccgttccc acgccccgcg ccacgtcaca aactccaccc cctcattatc    4740
atattggctt caatccaaaa taaggtatat tattgatgat gttaattaac atgcatggat    4800
```

-continued

```
ccatatgcgg tgtgaaatac cgcacagatg cgtaaggaga aaataccgca tcaggcgctc   4860
ttccgcttcc tcgctcactg actcgctgcg ctcggtcgtt cggctgcggc gagcggtatc   4920
agctcactca aaggcggtaa tacgttatc cacagaatca ggggataacg caggaaagaa    4980
catgtgagca aaaggccagc aaaaggccag gaaccgtaaa aaggccgcgt tgctggcgtt   5040
tttccatagg ctccgccccc ctgacgagca tcacaaaaat cgacgctcaa gtcagaggtg   5100
gcgaaacccg acaggactat aaagatacca ggcgtttccc cctggaagct ccctcgtgcg   5160
ctctcctgtt ccgaccctgc cgcttaccgg atacctgtcc gcctttctcc cttcgggaag   5220
cgtggcgctt tctcatagct cacgctgtag gtatctcagt tcggtgtagg tcgttcgctc   5280
caagctgggc tgtgtgcacg aaccccccgt tcagcccgac cgctgcgcct tatccggtaa   5340
ctatcgtctt gagtccaacc cggtaagaca cgacttatcg ccactggcag cagccactgg   5400
taacaggatt agcagagcga ggtatgtagg cggtgctaca gagttcttga agtggtggcc   5460
taactacggc tacactagaa ggacagtatt tggtatctgc gctctgctga agccagttac   5520
cttcggaaaa agagttggta gctcttgatc cggcaaacaa accaccgctg gtagcggtgg   5580
tttttttgtt tgcaagcagc agattacgcg cagaaaaaaa ggatctcaag aagatccttt   5640
gatcttttct acgggtctg acgctcagtg gaacgaaaac tcacgttaag ggattttggt    5700
catgagatta tcaaaaagga tcttcaccta gatccttta aattaaaaat gaagttttaa    5760
atcaatctaa agtatatatg agtaaacttg gtctgacagt taccaatgct taatcagtga   5820
ggcacctatc tcagcgatct gtctatttcg ttcatccata gttgcctgac tccccgtcgt   5880
gtagataact acgatacggg agggcttacc atctggcccc agtgctgcaa tgataccgcg   5940
agacccacgc tcaccggctc cagatttatc agcaataaac cagccagccg aagggccga    6000
gcgcagaagt ggtcctgcaa ctttatccgc ctccatccag tctattaatt gttgccggga   6060
agctagagta agtagttcgc cagttaatag tttgcgcaac gttgttgcca ttgctgcagc   6120
catgagatta tcaaaaagga tcttcaccta gatccttttc acgtagaaag ccagtccgca   6180
gaaacggtgc tgacccggga tgaatgtcag ctactgggct atctggacaa gggaaaacgc   6240
aagcgcaaag agaaagcagg tagcttgcag tgggcttaca tggcgatagc tagactgggc   6300
ggttttatgg acagcaagcg aaccggaatt gccagctggg gcgccctctg gtaaggttgg   6360
gaagccctgc aaagtaaact ggatggcttt cttgccgcca aggatctgat ggcgcagggg   6420
atcaagctct gatcaagaga caggatgagg atcgtttcgc atgattgaac aagatggatt   6480
gcacgcaggt tctccggccg cttgggtgga gaggctattc ggctatgact gggcacaaca   6540
gacaatcggc tgctctgatg ccgccgtgtt ccggctgtca gcgcagggc gcccggttct    6600
ttttgtcaag accgacctgt ccggtgccct gaatgaactg caagacgagg cagcgcggct   6660
atcgtggctg gccacgacgg gcgttccttg cgcagctgtg ctcgacgttg tcactgaagc   6720
gggaagggac tggctgctat tgggcgaagt gccggggcag gatctcctgt catctcacct   6780
tgctcctgcc gagaaagtat ccatcatggc tgatgcaatg cggcggctgc atacgcttga   6840
tccggctacc tgcccattcg accaccaagc gaaacatcgc atcgagcgag cacgtactcg   6900
gatggaagcc ggtcttgtcg atcaggatga tctggacgaa gagcatcagg ggctcgcgcc   6960
agccgaactg ttcgccaggc tcaaggcgag catgcccgac ggcgaggatc tcgtcgtgac   7020
ccatggcgat gcctgcttgc cgaatatcat ggtggaaaat ggccgctttt ctggattcat   7080
cgactgtggc cggctgggtg tggcggaccg ctatcaggac atagcgttgg ctacccgtga   7140
```

-continued

```
tattgctgaa gagcttggcg gcgaatgggc tgaccgcttc ctcgtgcttt acggtatcgc      7200
cgctcccgat tcgcagcgca tcgccttcta tcgccttctt gacgagttct tctgaatttt      7260
gttaaaattt ttgttaaatc agctcatttt ttaaccaata ggccgaaatc ggcaacatcc      7320
cttataaatc aaaagaatag accgcgatag ggttgagtgt tgttccagtt tggaacaaga      7380
gtccactatt aaagaacgtg gactccaacg tcaaagggcg aaaaaccgtc tatcagggcg      7440
atggcccact acgtgaacca tcacccaaat caagttttt gcggtcgagg tgccgtaaag      7500
ctctaaatcg gaaccctaaa gggagccccc gatttagagc ttgacgggga agccggcga       7560
acgtggcgag aaaggaaggg aagaaagcga aggagcggg cgctagggcg ctggcaagtg       7620
tagcggtcac gctgcgcgta accaccacac ccgcgcgctt aatgcgccgc tacagggcgc      7680
gtccattcgc cattcaggat cgaattaatt cttaattaa                             7719

<210> SEQ ID NO 35
<211> LENGTH: 6851
<212> TYPE: DNA
<213> ORGANISM: Artificial sequence
<220> FEATURE:
<223> OTHER INFORMATION: Retroviral vector pFB-nTAP-neo

<400> SEQUENCE: 35
gaattgctag caattgctag caattgctag caattcatac cagatcaccg aaaactgtcc        60
tccaaatgtg tcccctcac actcccaaat tcgcgggctt ctgcctctta gaccactcta       120
ccctattccc cacactcacc ggagccaaag ccgcgggaca tatacatgtg aaagacccca       180
cctgtaggtt tggcaagcta gcttaagtaa cgccattttg caaggcatgg aaaatacat       240
aactgagaat agaaaagttc agatcaaggt caggaacaga tggaacagct gaatatgggc       300
caaagcggat atctgtggta agcagttcct gccccggctc agggccaaga acagatggaa       360
cagctgaata tgggccaaac aggatatctg tggtaagcag ttcctgcccc ggctcagggc       420
caagaacaga tggtccccag atgcggtcca gccctcagca gtttctagag aaccatcaga      480
tgtttccagg gtgccccaag gacctgaaat gaccctgtgc cttatttgaa ctaaccaatc      540
agttcgcttc tcgcttctgt tcgcgcgctt ctgctccccg agtcaataa aagagcccac       600
aacccctcac tcggggcgcc agtcctccga ttgactgagt cgcccggta cccgtgtatc        660
caataaaccc tcttgcagtt gcatccgact tgtggtctcg ctgttccttg ggagggtctc       720
ctctgagtga ttgactaccc gtcagcgggg gtctttcatt tgggggctcg tccgggatcg       780
ggagaccccct gcccagggac caccgaccca ccaccggag taagctggc cagcaactta       840
tctgtgtctg tccgattgtc tagtgtctat gactgatttt atgcgcctgc gtcggtacta       900
gttagctaac tagctctgta tctggcggac ccgtggtgga actgacgagt tcggaacacc       960
cggccgcaac cctgggagac gtcccaggga cttcggggc gttttgtg gcccgacctg        1020
agtccaaaaa tcccgatcgt tttggactct ttggtgcacc cccctagag gaggatatg        1080
tggttctggt aggagacgag aacctaaaac agttcccgcc tccgtctgaa tttttgcttt      1140
cggtttggga ccgaagccgc gccgcgcgtc ttgtctgctg cagcatcgtt ctgtgttgtc      1200
tctgtctgac tgtgtttctg tatttgtctg aaaatatggg cccgggccag actgttacca      1260
ctcccttaag tttgacctta ggtcactgga agatgtcga gcggatcgct cacaaccagt       1320
cggtagatgt caagaagaga cgttgggtta ccttctgctc tgcagaatgg ccaacccttta     1380
acgtcggatg gccgcgagac ggcacccttta acgagacct catcacccag gttaagatca      1440
aggtcttttc acctggcccg catggacacc cagaccaggt cccctacatc gtgacctggg      1500
```

```
aagccttggc ttttgacccc cctccctggg tcaagccctt tgtacaccct aagcctccgc   1560
ctcctcttcc tccatccgcc ccgtctctcc cccttgaacc tcctcgttcg accccgcctc   1620
gatcctccct ttatccagcc ctcactcctt ctctaggcgc ccccatatgg ccatatgaga   1680
tcttatatgg ggcaccccg cccttgtaa acttccctga ccctgacatg acaagagtta   1740
ctaacagccc ctctctccaa gctcacttac aggctctcta cttagtccag cacgaagtct   1800
ggagacctct ggcggcacgt accaagaaca actggaccga ccggtggtac ctcaccctta   1860
ccgagtcggc gacacagtgt gggtccgccg acaccagact aagaacctag aacctcgctg   1920
gaaaggacct tacacagtcc tgctgaccac ccccaccgcc ctcaaagtag acggcatcgc   1980
agcttggata cacgccgccc acgtgaaggc tgccgacccc gggggtggac catcctctag   2040
actgccggat cgaattgtcg actgctagca tgaagcgacg atggaaaaag aatttcatag   2100
ccgtctcagc agccaaccgc tttaagaaaa tctcatcctc cggggcactt ggaagcggta   2160
gcggtaccat ggacgagaag accaccggct ggcggggcgg ccacgtggtg gagggcctgg   2220
ccggcgagct ggagcagctg cgggccaggc tggagcacca ccctcagggc cagcgggagc   2280
cctccggcgg ctgcaagctg ggcgcccggg catcgatacg cgtccagcac agtgggaatt   2340
caggcctgga tcctcgagcg gccgcgatcc ggttattttc caccatattg ccgtcttttg   2400
gcaatgtgag ggcccggaaa cctggccctg tcttcttgac gagcattcct aggggtcttt   2460 ccctctcgc caaaggaatg caaggtctgt tgaatgtcgt gaaggaagca gttcctctgg   2520
aagcttcttg aagacaaaca acgtctgtag cgacccttg caggcagcgg aaccccccac   2580
ctggcgacag gtgcctctgc ggccaaaagc cacgtgtata agatacacct gcaaaggcgg   2640 cacaaccca gtgccacgtt gtgagttgga tagttgtgga aagagtcaaa tggctctcct   2700
caagcgtatt caacaagggg ctgaaggatg cccagaaggt accccattgt atgggatctg   2760
atctggggcc tcggtgcaca tgctttacat gtgtttagtc gaggttaaaa aacgtctagg   2820 cccccgaac cacggggacg tggtttatcc tttgaaaaac acgatgcata atatggaaca   2880
aaaacttatt tctgaagaag acttggacac caaactttcc tgccgctcga tttctccacc   2940
cccaggtgaa ctcctcccte acctccccga cggggcgagg ctccatggct gccccctcgc   3000
tgcacccgtc tggtgccacg cggttccatg ggatcgtttc gcatgattga acaagatgga   3060
ttgcacgcag gttctccggc cgcttgggtg gagaggctat tcggctatga ctgggcacaa   3120
cagacaatcg gctgctctga tgccgccgtg ttccggctgt cagcgcaggg gcgcccggtt   3180 cttttgtca agaccgacct gtccggtgcc ctgaatgaac tgcaggacga ggcagcgcgg   3240
ctatcgtggc tggccacgac gggcgttcct tgcgcagctg tgctcgacgt tgtcactgaa   3300
gcgggaaggg actggctgct attgggcgaa gtgccggggc aggatctcct gtcatctcac   3360
cttgctcctg ccgagaaagt atccatcatg gctgatgcaa tgcggcggct gcatacgctt   3420
gatccggcta cctgcccatt cgaccaccaa gcgaaacatc gcatcgagcg agcacgtact   3480
cggatggaag ccggtcttgt cgatcaggat gatctggacg aagagcatca ggggctcgcg   3540
ccagccgaac tgttcgccag gctcaaggcg cgcatgcccg acggcgagga tctcgtcgtg   3600
acccatggcg atgcctgctt gccgaatatc atggtggaaa atggccgctt tctggattc   3660 atcgactgtg gccggctggg tgtggcggac cgctatcagg acatagcgtt ggctacccgt   3720
gatattgctg aagagcttgg cggcgaatgg gctgaccgct tcctcgtgct ttacggtatc   3780
gccgctcccg attcgcagcg catcgccttc tatcgccttc ttgacgagtt cttctgagcg   3840
```

-continued

```
ggactctggg gttcgataaa ataaaagatt ttatttagtc tccagaaaaa gggggaatg    3900
aaagacccca cctgtaggtt tggcaagcta gcttaagtaa cgccattttg caaggcatgg    3960
aaaaatacat aactgagaat agagaagttc agatcaaggt caggaacaga tggaacagct    4020
gaatatgggc caaacaggat atctgtggta agcagttcct gccccggctc agggccaaga    4080
acagatggaa cagctgaata tgggccaaac aggatatctg tggtaagcag ttcctgcccc    4140
ggctcagggc caagaacaga tggtcccag atgcggtcca gccctcagca gtttctagag    4200
aaccatcaga tgtttccagg gtgccccaag acctgaaat gaccctgtgc cttatttgaa     4260
ctaaccaatc agttcgcttc tcgcttctgt tcgcgcgctt ctgctcccg agctcaataa     4320
aagagcccac aacccctcac tcgggcgcc agtcctccga ttgactgagt cgcccgggta     4380
cccgtgtatc aataaaccc tcttgcagtt gcatccgact tgtggtctcg ctgttccttg     4440
ggagggtctc ctctgagtga ttgactaccc gtcagcgggg gtctttcatt tgggggctcg    4500
tccgggatcg ggagacccct gcccagggac caccgaccca ccaccgggag gtaagctggc    4560
tgcctcgcgc gtttcggtga tgacggtgaa acctctgac acatgcagct cccggagacg     4620
gtcacagctt gtctgtaagc ggatgccggg agcagacaag cccgtcaggg cgcgtcagcg    4680
ggtgttggcg ggtgtcgggg cgcagccatg acccagtcac gtagcgatag cggagtgtat    4740
actggcttaa ctatgcggca tcagagcaga ttgtactgag agtgcaccat atgcggtgtg    4800
aaataccgca cagatgcgta aggagaaaat accgcatcag gcgctcttcc gcttcctcgc    4860
tcactgactc gctgcgctcg tcgttcggc tgcggcgagc ggtatcagct cactcaaagg     4920
cggtaatacg gttatccaca gaatcagggg ataacgcagg aaagaacatg tgagcaaaag    4980
gccagcaaaa ggccaggaac cgtaaaaagg ccgcgttgct ggcgtttttc cataggctcc    5040
gcccccctga cgagcatcac aaaaatcgac gctcaagtca gaggtggcga aacccgacag    5100
gactataaag ataccaggcg tttccccctg gaagctccct cgtgcgctct cctgttccga    5160
ccctgccgct taccggatac ctgtccgcct ttctcccttc gggaagcgtg gcgctttctc    5220
atagctcacg ctgtaggtat ctcagttcgg tgtaggtcgt tcgctccaag ctgggctgtg    5280
tgcacgaacc ccccgttcag cccgaccgct gcgccttatc cggtaactat cgtcttgagt    5340
ccaacccggt aagacacgac ttatcgccac tggcagcagc cactggtaac aggattagca    5400
gagcgaggta tgtaggcggt gctacagagt tcttgaagtg gtggcctaac tacggctaca    5460
ctagaaggac agtatttggt atctgcgctc tgctgaagcc agttaccttc ggaaaaagag    5520
ttggtagctc ttgatccggc aaacaaacca ccgctggtag cggtggtttt tttgtttgca    5580
agcagcagat tacgcgcaga aaaaaggat ctcaagaaga tcctttgatc ttttctacgg     5640
ggtctgacgc tcagtggaac gaaaactcac gttaaggat tttggtcatg agattatcaa     5700
aaaggatctt cacctagatc cttttaaatt aaaaatgaag ttttaaatca atctaaagta    5760
tatatgagta aacttggtct gacagttacc aatgcttaat cagtgaggca cctatctcag    5820
cgatctgtct atttcgttca tccatagttg cctgactccc cgtcgtgtag ataactacga    5880
tacgggaggg cttaccatct ggccccagtg ctgcaatgat accgcgagac ccacgctcac    5940
cggctccaga tttatcagca ataaaccagc cagccggaag ggccgagcgc agaagtggtc    6000
ctgcaacttt atccgcctcc atccagtcta ttaattgttg ccgggaagct agagtaagta    6060
gttcgccagt taatagtttg cgcaacgttg ttgccattgc tgcaggcatc gtggtgtcac    6120
gctcgtcgtt tggtatggct tcattcagct ccggttccca acgatcaagg cgagttacat    6180
gatcccccat gttgtgcaaa aaagcggtta gctccttcgg tcctccgatc gttgtcagaa    6240
```

-continued

| | |
|---|---|
| gtaagttggc cgcagtgtta tcactcatgg ttatggcagc actgcataat tctcttactg | 6300 |
| tcatgccatc cgtaagatgc ttttctgtga ctggtgagta ctcaaccaag tcattctgag | 6360 |
| aatagtgtat gcggcgaccg agttgctctt gcccggcgtc aacacgggat aataccgcgc | 6420 |
| cacatagcag aactttaaaa gtgctcatca ttggaaaacg ttcttcgggg cgaaaactct | 6480 |
| caaggatctt accgctgttg agatccagtt cgatgtaacc cactcgtgca cccaactgat | 6540 |
| cttcagcatc ttttactttc accagcgttt ctgggtgagc aaaaacagga aggcaaaatg | 6600 |
| ccgcaaaaaa gggaataagg gcgacacgga aatgttgaat actcatactc ttcctttttc | 6660 |
| aatattattg aagcatttat cagggttatt gtctcatgag cggatacata tttgaatgta | 6720 |
| tttagaaaaa taaacaaata ggggttccgc gcacatttcc ccgaaaagtg ccacctgacg | 6780 |
| tctaagaaac cattattatc atgacattaa cctataaaaa taggcgtatc acgaggccct | 6840 |
| ttcgtcttca a | 6851 |

<210> SEQ ID NO 36
<211> LENGTH: 6825
<212> TYPE: DNA
<213> ORGANISM: Artificial sequence
<220> FEATURE:
<223> OTHER INFORMATION: Retroviral vector pFB-cTAP-neo

<400> SEQUENCE: 36

| | |
|---|---|
| gaattgctag caattgctag caattgctag caattcatac cagatcaccg aaaactgtcc | 60 |
| tccaaatgtg tcccctcac actcccaaat tcgcgggctt ctgcctctta gaccactcta | 120 |
| ccctattccc cacactcacc ggagccaaag ccgcgggaca tatacatgtg aaagacccca | 180 |
| cctgtaggtt tggcaagcta gcttaagtaa cgccattttg caaggcatgg aaaatacat | 240 |
| aactgagaat agaaaagttc agatcaaggt caggaacaga tggaacagct gaatatgggc | 300 |
| caaagcggat atctgtggta agcagttcct gccccggctc agggccaaga acagatggaa | 360 |
| cagctgaata tgggccaaac aggatatctg tggtaagcag ttcctgcccc ggctcagggc | 420 |
| caagaacaga tggtccccag atgcggtcca gccctcagca gtttctagag aaccatcaga | 480 |
| tgtttccagg gtgccccaag gacctgaaat gaccctgtgc cttatttgaa ctaaccaatc | 540 |
| agttcgcttc tcgcttctgt tcgcgcgctt ctgctccccg agctcaataa aagagcccac | 600 |
| aaccccctcac tcggggcgcc agtcctccga ttgactgagt cgcccgggta cccgtgtatc | 660 |
| caataaaccc tcttgcagtt gcatccgact tgtggtctcg ctgttccttg ggagggtctc | 720 |
| ctctgagtga ttgactaccc gtcagcgggg gtctttcatt tgggggctcg tccgggatcg | 780 |
| ggagacccct gcccagggac caccgaccca ccacgggag gtaagctggc cagcaactta | 840 |
| tctgtgtctg tccgattgtc tagtgtctat gactgatttt atgcgcctgc gtcggtacta | 900 |
| gttagctaac tagctctgta tctggcggac ccgtggtgga actgacgagt tcggaacacc | 960 |
| cggccgcaac cctgggagac gtcccaggga cttcggggc cgttttttgtg gcccgacctg | 1020 |
| agtccaaaaa tcccgatcgt tttggactct tggtgcacc cccttagag gagggatatg | 1080 |
| tggttctggt aggagacgag aacctaaaac agttcccgcc tccgtctgaa tttttgcttt | 1140 |
| cggtttggga ccgaagccgc gccgcgcgtc ttgtctgctg cagcatcgtt ctgtgttgtc | 1200 |
| tctgtctgac tgtgtttctg tatttgtctg aaaatatggg cccgggccag actgttacca | 1260 |
| ctcccttaag tttgacctta ggtcactgga aagatgtcga gcggatcgct cacaaccagt | 1320 |
| cggtagatgt caagaagaga cgttgggtta ccttctgctc tgcagaatgg ccaaccttta | 1380 |

-continued

```
acgtcggatg gccgcgagac ggcacccttta accgagacct catcacccag gttaagatca    1440 aggtctttc  acctggcccg catggacacc cagaccaggt cccctacatc gtgacctggg     1500
aagccttggc ttttgacccc cctccctggg tcaagccctt tgtacaccct aagcctccgc     1560
ctcctcttcc tccatccgcc ccgtctctcc cccttgaacc tcctcgttcg accccgcctc     1620
gatcctccct ttatccagcc ctcactcctt ctctaggcgc ccccatatgg ccatatgaga     1680
tcttatatgg ggcaccccg  cccccttgtaa acttccctga ccctgacatg acaagagtta    1740
ctaacagccc ctctctccaa gctcacttac aggctctcta cttagtccag cacgaagtct     1800
ggagacctct ggcggcacgt accaagaaca actggaccga ccggtggtac ctcaccctta     1860
ccgagtcggc gacacagtgt gggtccgccg acaccagact aagaacctag aacctcgctg     1920
gaaaggacct tacacagtcc tgctgaccac ccccaccgcc ctcaaagtag acggcatcgc     1980
agcttggata cacgccgccc acgtgaaggc tgccgacccc ggggtggac  catcctctag     2040 actgccggat cgaattgtcg acatcgatac gcgtccagca cagtgggaat tcaggcctgg    2100
atcctcgaga tggacgagaa gaccaccggc tggcggggcg gccacgtggt ggagggcctg    2160
gccggcgagc tggagcagct gcgggccagg ctggagcacc accctcaggg ccagcgggag    2220
ccctccggcg gctgcaagct gggctccgga aagcgacgat ggaaaaagaa tttcatagcc    2280
gtctcagcag ccaaccgctt taagaaaatc tcatcctccg gggcacttta ggcggccgcg    2340
atccggttat tttccaccat attgccgtct tttggcaatg tgagggcccg gaaacctggc    2400
cctgtcttct tgacgagcat tcctaggggt cttttcccctc tcgccaaagg aatgcaaggt    2460
ctgttgaatg tcgtgaagga agcagttcct ctggaagctt cttgaagaca aacaacgtct    2520
gtagcgaccc tttgcaggca gcggaacccc ccacctggcg acaggtgcct ctgcggccaa    2580
aagccacgtg tataagatac acctgcaaag gcggcacaac cccagtgcca cgttgtgagt    2640
tggatagttg tggaaagagt caaatggctc tcctcaagcg tattcaacaa ggggctgaag    2700
gatgcccaga aggtaccca  ttgtatggga tctgatctgg ggcctcggtg cacatgctttt   2760 acatgtgttt agtcgaggtt aaaaaacgtc taggcccccc gaaccacggg gacgtggttt    2820
atcctttgaa aaacacgatg cataatatgg aacaaaaact tatttctgaa gaagacttgg    2880
acaccaaact ttcctgccgc tcgattctc  caccccagg  tgaactcctc cctcacctcc    2940 ccgacgggc  gaggctccat ggctgccccc tcgctgcacc cgtctggtgc cacgcggttc    3000
catgggatcg tttcgcatga ttgaacaaga tggattgcac gcaggttctc cggccgcttg    3060
ggtggagagg ctattcggct atgactgggc acaacagaca atcggctgct ctgatgccgc    3120
cgtgttccgg ctgtcagcgc agggggcgccc ggttctttttt gtcaagaccg acctgtccgg    3180
tgccctgaat gaactgcagg acgaggcagc gcggctatcg tggctggcca cgacgggcgt    3240
tccttgcgca gctgtgctcg acgttgtcac tgaagcggga agggactggc tgctattggg    3300
cgaagtgccg gggcaggatc tcctgtcatc tcaccttgct cctgccgaga agtatccat    3360 catggctgat gcaatgcggc ggctgcatac gcttgatccg gctacctgcc cattcgacca    3420
ccaagcgaaa catcgcatcg agcgagcacg tactcggatg gaagccggtc ttgtcgatca    3480
ggatgatctg gacgaagagc atcaggggct cgcgccagcc gaactgttcg ccaggctcaa    3540
ggcgcgcatg cccgacggcg aggatctcgt cgtgacccat ggcgatgcct gcttgccgaa    3600
tatcatggtg gaaaatggcc gcttttctgg attcatcgac tgtggccggc tgggtgtggc    3660
ggaccgctat caggacatag cgttggctac ccgtgatatt gctgaagagc ttggcggcga    3720
atgggctgac cgcttcctcg tgctttacgg tatcgccgct cccgattcgc agcgcatcgc    3780
```

```
cttctatcgc cttcttgacg agttcttctg agcgggactc tggggttcga taaaataaaa    3840
gattttattt agtctccaga aaagggggg aatgaaagac cccacctgta ggtttggcaa     3900
gctagcttaa gtaacgccat tttgcaaggc atggaaaaat acataactga aatagagaa     3960
gttcagatca aggtcaggaa cagatggaac agctgaatat gggccaaaca ggatatctgt    4020
ggtaagcagt tcctgccccg gctcagggcc aagaacagat ggacagctg aatatgggcc     4080
aaacaggata tctgtggtaa gcagttcctg ccccggctca gggccaagaa cagatggtcc    4140
ccagatgcgg tccagccctc agcagtttct agagaaccat cagatgtttc cagggtgccc    4200
caaggacctg aaatgaccct gtgccttatt tgaactaacc aatcagttcg cttctcgctt    4260
ctgttcgcgc gcttctgctc cccgagctca ataaaagagc ccacaacccc tcactcgggg    4320
cgccagtcct ccgattgact gagtcgcccg ggtacccgtg tatccaataa accctcttgc    4380
agttgcatcc gacttgtggt ctcgctgttc cttgggaggg tctcctctga gtgattgact    4440
acccgtcagc gggggtcttt catttggggg ctcgtccggg atcgggagac ccctgcccag    4500
ggaccaccga cccaccaccg ggaggtaagc tggctgcctc gcgcgtttcg gtgatgacgg    4560
tgaaaacctc tgacacatgc agctcccgga gacggtcaca gcttgtctgt aagcggatgc    4620
cgggagcaga caagcccgtc agggcgcgtc agcgggtgtt ggcgggtgtc ggggcgcagc    4680
catgacccag tcacgtagcg atagcggagt gtatactggc ttaactatgc ggcatcagag    4740
cagattgtac tgagagtgca ccatatgcgg tgtgaaatac cgcacagatg cgtaaggaga    4800
aaataccgca tcaggcgctc ttccgcttcc tcgctcactg actcgctgcg ctcggtcgtt    4860
cggctgcggc gagcggtatc agctcactca aaggcggtaa tacggttatc cacagaatca    4920
ggggataacg caggaaagaa catgtgagca aaaggccagc aaaaggccag gaaccgtaaa    4980
aaggccgcgt tgctggcgtt tttccatagg ctccgccccc ctgacgagca tcacaaaaat    5040
cgacgctcaa gtcagaggtg gcgaaacccg acaggactat aaagatacca ggcgtttccc    5100
cctggaagct ccctcgtgcg ctctcctgtt ccgaccctgc cgcttaccgg atacctgtcc    5160
gcctttctcc cttcgggaag cgtggcgctt tctcatagct cacgctgtag gtatctcagt    5220
tcggtgtagg tcgttcgctc caagctgggc tgtgtgcacg aaccccccgt tcagcccgac    5280
cgctgcgcct tatccggtaa ctatcgtctt gagtccaacc cggtaagaca cgacttatcg    5340
ccactggcag cagccactgg taacaggatt agcagagcga ggtatgtagg cggtgctaca    5400
gagttcttga agtggtggcc taactacggc tacactagaa ggacagtatt tggtatctgc    5460
gctctgctga agccagttac cttcggaaaa agagttggta gctcttgatc cggcaaacaa    5520
accaccgctg gtagcggtgg tttttttgtt tgcaagcagc agattacgcg cagaaaaaaa    5580
ggatctcaag aagatccttt gatcttttct acggggtctg acgctcagtg gaacgaaaac    5640
tcacgttaag ggattttggt catgagatta tcaaaaagga tcttcaccta gatccttttta    5700
aattaaaaat gaagttttaa atcaatctaa agtatatatg agtaaacttg gtctgacagt    5760
taccaatgct taatcagtga ggcacctatc tcagcgatct gtctatttcg ttcatccata    5820
gttgcctgac tccccgtcgt gtagataact acgatacggg agggcttacc atctggcccc    5880
agtgctgcaa tgataccgcg agacccacgc tcaccggctc cagatttatc agcaataaac    5940
cagccagccg gaagggccga gcgcagaagt ggtcctgcaa ctttatccgc ctccatccag    6000
tctattaatt gttgccggga agctagagta agtagttcgc cagttaatag tttgcgcaac    6060
gttgttgcca ttgctgcagg catcgtggtg tcacgctcgt cgtttggtat ggcttcattc    6120
```

-continued

```
agctccggtt cccaacgatc aaggcgagtt acatgatccc ccatgttgtg caaaaaagcg     6180
gttagctcct tcggtcctcc gatcgttgtc agaagtaagt tggccgcagt gttatcactc     6240
atggttatgg cagcactgca taattctctt actgtcatgc catccgtaag atgcttttct     6300
gtgactggtg agtactcaac caagtcattc tgagaatagt gtatgcggcg accgagttgc     6360
tcttgcccgg cgtcaacacg ggataatacc gcgccacata gcagaacttt aaaagtgctc     6420
atcattggaa aacgttcttc ggggcgaaaa ctctcaagga tcttaccgct gttgagatcc     6480
agttcgatgt aacccactcg tgcacccaac tgatcttcag catcttttac tttcaccagc     6540
gtttctgggt gagcaaaaac aggaaggcaa aatgccgcaa aaaagggaat aagggcgaca     6600
cggaaatgtt gaatactcat actcttcctt tttcaatatt attgaagcat ttatcagggt     6660
tattgtctca tgagcggata catatttgaa tgtatttaga aaaataaaca aataggggtt     6720
ccgcgcacat ttccccgaaa agtgccacct gacgtctaag aaaccattat tatcatgaca     6780
ttaacctata aaataggcg tatcacgagg ccctttcgtc ttcaa                      6825
```

COMPOSITIONS AND METHODS FOR PROTEIN ISOLATION

RELATED APPLICATIONS

This application is a Continuation-In-Part of U.S. patent application Ser. No. 10/712,137, filed Nov. 13, 2003, the entirety of which is incorporated herein by reference.

FIELD OF THE INVENTION

The invention relates in general to improved methods of protein isolation and identification of protein binding partners for a protein of interest.

BACKGROUND OF THE INVENTION

Identification of protein/protein interactions is at the core of understanding the biological processes occurring in living cells. Traditionally, the potential interacting proteins have been identified by genetic methods (two hybrid screens) with subsequent verification of the interaction by co-immunoprecipitation. While this method has been very successful for detection of two interacting proteins, it is of limited utility when more complex protein aggregates such as ribosomes, splice complexes or transcription complexes are investigated.

To identify and isolate yeast complex protein aggregates, an alternative method has been developed by Seraphin et al. (Rigaut et al., 1999, Nature Biotech., 17: 1030–1032; Puig et al., 2001, Methods, 24: 218–219; U.S. 2002/0061513, reviewed in Terpe et al., 2003, App. Microbiol. Biotechnol., 60: 523–533). This method combines purification of the protein complex of interest using two different affinity purification tags fused to at least one known protein component of a complex of interest by genetic methods, with subsequent mass spectroscopy to identify the unknown components of the isolated complex. The use of two consecutive purification steps allows for isolation of the complex, in a purified form, without disruption of the targeted complex. Only certain combinations of purification tags are suitable for this method.

The calmodulin-binding domain of the calmodulin binding peptide (CBP-tag) and the IgG binding domain(s) of *Staphylococcus aureus* protein A represent an efficient combination of purification tags, according to this method (Rigaut et al., supra; Puig et al., supra; U.S. 2002/0061513). The interaction between the CBP-tag and the purification matrix (immobilized calmodulin) can be controlled by the presence of $Ca^{2+}$. In the presence of $Ca^{2+}$, the CBP tag binds to the purification matrix whereas removal of $Ca^{2+}$ with a chelating agent such as EGTA, allows recovery of the tagged protein from the purification resin under mild conditions (Stofko-Hahn et al., 1992, FEBS Lett., 302: 274–278). The IgG-binding domain of protein A provides specific, high affinity binding with little non-specific interaction. However, it is very difficult to elute protein A tagged proteins from IgG-columns. Consequently, elution can only be achieved by removing protein A fusion proteins by digestion with a site-specific protease. Utilization of the IgG-binding domain of protein A therefore requires additional processing steps and leads to contamination of the purified protein with the protease.

SUMMARY OF THE INVENTION

The invention provides reagents for detecting and isolating proteins in a complex. In particular, the invention provides for a vector comprising at least two affinity tags. The invention provides for a protein comprising at least two affinity tags. Alternatively, the invention provides for a protein of interest comprising at least one affinity tag, and a binding partner, or candidate binding partner for the protein of interest comprising at least a second affinity tag. The invention also provides methods for identifying and detecting a protein in a complex, without disruption of the complex. The method of the invention can be used to find one or more "target" binding partners for a "bait" protein of interest. According to the method of the invention, the protein of interest is fused in frame, either N-terminally, C-terminally or a combination thereof, to at least two affinity tags.

In one embodiment, the invention provides for a polynucleotide comprising at least two affinity tag sequences. In one embodiment, one of the tag sequences encodes streptavidin-binding peptide having a nucleotide sequence presented in FIG. 1. The at least two tag sequences are either directly adjacent to each other or are separated by a spacer, for example, of 1–60 nucleotides. Either of the first or second tags can be located 5' of the other tag.

In one embodiment the invention provides for a polynucleotide comprising a gene of interest and at least two tag sequences. The gene of interest is fused in frame with each of the tag sequences. In one embodiment, one of the tag sequences encodes streptavidin-binding peptide having a nucleotide sequence presented in FIG. 1.

As used herein, the terms "nucleic acid", "polynucleotide" and "oligonucleotide" refer to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

As used herein, "protein of interest" means any protein for which the nucleic acid sequence is known or available, or that becomes available, such that it can be cloned into a nucleic acid vector which is suitable for expression in the appropriate host cells or cell-free expression systems. For purification of a protein complex, the nucleic acid sequence of at least one of the subunits of the protein complex must be known or available.

The invention also provides for identification and/or purification of a protein complex, or identification and/or purification of a complex of one or more proteins and one or more biomolecules. As used herein, a "biomolecule" includes a protein, peptide, nucleic acid, antibody, or other biomolecule. A biomolecule complex is a complex of at least two biomolecules, preferably at least one protein in association with either other proteins or with other biomolecules, for example, nucleic acid or antibody. The biomolecule complexes can be naturally occurring, such as nuclear snRNPs or antigen-antibody complexes, or they can be non-naturally occurring, for example, mutant DNA binding protein in association with mutant target DNA. Any complex molecule comprising as one or more subunits a polypeptide or subunit expressed according to the invention and/or further comprising other components which associate in a manner stable enough to remain associated during the affinity purification steps is a biomolecule complex that can be detected/purified by the method of the invention.

The terms "tag" or "affinity tag" are used interchangeably herein. As used herein, "tag" or "affinity tag" means a moiety that is fused in frame to the 5' or 3' end of, or internally to, the protein product of a gene of interest, a biomolecule of the invention, or another tag. A "tag" specifically binds to a ligand as a result of attractive forces that exist between the tag and a ligand. "Specifically binds" as it refers to a "tag" and a ligand means via covalent or hydrogen bonding or electrostatic attraction or via an interaction between for example a tag and a ligand, an antibody and an antigen, protein subunits, or a nucleic acid binding protein and a nucleic acid binding site. Preferably, a "tag" of the invention, binds a ligand with a dissociation constant ($K_D$) of at least about $1 \times 10^3$ $M^{-1}$, usually at least $1 \times 10^4$ $M^{-1}$, typically at least $1 \times 10^5$ $M^{-1}$, preferably at least $1 \times 10^6$ $M^{-1}$ to $1 \times 10^9$ $M^{-1}$ or more, for example $1 \times 10^{14}$ $M^{-1}$ for streptavidin-avidin binding, $1 \times 10^{15}$ $M^{-1}$, $1 \times 10^{16}$ $M^{-1}$, $1 \times 10^{20}$ $M^{-1}$, or more. A tag does not interfere with expression, folding or processing of the tagged protein or with the ability of a protein to bind to its binding partner. Tags include but are not limited to calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, maltose-binding protein, TrxA, DsbA, hemagglutinin epitope, InaD, NorpA, and GFP (see Honey et al., supra; Hu et al., supra; Puig et al., supra; Rigaut et al., supra; Terpe, supra; U.S. 2002/0061513, Kimple et al., Biotechniques. 2002, 33: 578) incorporated by reference herein in their entirety.

As used herein, "fused in frame" means fused such that the correct translational reading frame is maintained thereby allowing for expression of all of the components of the chimeric or fusion protein.

As used herein, the term "fused to the amino-terminal end" refers to the linkage of a polypeptide sequence to the amino terminus of another polypeptide. The linkage may be direct or may be mediated by a short (e.g., about 2–20 amino acids) linker peptide. Examples of useful linker peptides include, but are not limited to, glycine polymers $((G)_n)$ including glycine-serine and glycine-alanine polymers. It should be understood that the amino-terminal end as used herein refers to the existing amino-terminal amino acid of a polypeptide, whether or not that amino acid is the amino terminal amino acid of the wild type or a variant form (e.g., an amino-terminal truncated form) of a given polypeptide.

As used herein, the term "fused to the carboxy-terminal end" refers to the linkage of a polypeptide sequence to the carboxyl terminus of another polypeptide. The linkage may be direct or may be mediated by a linker peptide. As with fusion to the amino-terminal end, fusion to the carboxy-terminal end refers to linkage to the existing carboxy-terminal amino acid of a polypeptide.

As used herein, steptavidin binding peptide (SBP)" or steptavidin binding protein means a synthetic streptavidin-binding domain that binds streptavidin with a dissociation constant from $1 \times 10^5$ $M^{-1}$–$5 \times 10^{10}$ $M^{-1}$ (for example, $1 \times 10^5$ $M^{-1}$, $1 \times 10^6$ $M^{-1}$, $1 \times 10^7$ $M^{-1}$, $1 \times 10^8$ $M^{-1}$, $1 \times 10^9$ $M^{-1}$, $1 \times 10^{10}$ $M^{-1}$ in the absence but not in the presence of biotin. In one embodiment, SBP has the amino acid sequence presented in FIG. 1. Additional SBP sequences useful according to the invention include SB1, SB2, SB5, SB9, SB11 and SB12 (Wilson et al., 2001, Proc. Natl. Acad. Sci USA, 98:3750), presented in FIG. 2.

The invention also provides for an isolated polynucleotide comprising at least two tag sequences, wherein one of the tag sequences encodes streptavidin binding peptide and the other encodes calmodulin binding peptide. The at least two tag sequences are either directly adjacent to each other or are separated by a spacer, for example, of 1–60 nucleotides. Either of the streptavidin binding peptide tag or the calmodulin binding peptide tag can be located 5' of the other tag.

The invention also provides for an isolated polynucleotide comprising a gene sequence of interest and at least two tag sequences fused in frame with each other. One of the two tag sequences encodes streptavidin binding peptide and one of the tag sequences encodes calmodulin binding peptide.

As used herein, "calmodulin binding peptide (CBP)" or calmodulin binding peptide means a peptide that binds calmodulin, preferably with a dissociation constant from $1 \times 10^3$ $M^{-1}$ to $1 \times 10^{14}$ $M^{-1}$ and preferably $1 \times 10^6$ $M^{-1}$ to $1 \times 10^{10}$ $M^{-1}$ and more preferably, $1 \times 10^7$ $M^{-1}$ to $1 \times 10^9$ $M^{-1}$, in a Ca2+ dependent manner. Binding occurs in the presence of $Ca^{2+}$, in the range of 0.1 µM to 10 mM. CBP is derived from the C-terminus of skeletal-muscle myosin light chain kinase. In the presence of $Ca^{2+}$, the CBP tag binds to calmodulin and, upon removal of $Ca^{2+}$, for example, in the presence of a chelating agent such as EGTA (preferably in the range of 0.1 µM to 10 mM), CBP does not bind calmodulin. In one embodiment, CBP has the amino acid sequence presented in FIG. 1. Additional CBP sequences useful according to the invention include: bovine neuromodulin AA 37–53 KIQASFRGHITRKKLKG (SEQ ID NO: 1; Hinfichsen et al., 1993, Proc. Natl. Acad Sci USA, 90:1585); calmodulin-dependent protein kinase I (CMKI) AA 294–318 SEQIKKNFAKSKWKQAFNATAV-VRHMRK (SEQ ID NO: 2; calmodulin-dependent protein kinase II (CMKII) AA 290–309 LKKFNARRKLKGAIL-TTMLA (SEQ ID NO: 3); and tuberous sclerosis 2 (TSC) WIARLRHIKRLRQRIL (SEQ ID NO: 4; Noonan et al., 2002, Arch, Biochem. Biophys. 389:32).

In one embodiment, each of the tags of the isolated polynucleotide are adjacent to the 5'end of the target gene sequence.

In another embodiment, each of the tags of the isolated polynucleotide are adjacent to the 3' end of the target gene sequence.

Since mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5'end" if its 5' phosphate is not linked to the 3' oxygen of a mononucleotide pentose rings, and as the "3'end" if its 3' oxygen is not linked to a 5' phosphate of a subsequent mononucleotide pentose ring.

As used herein, "adjacent" or "tandem" means immediately preceding or following. "Adjacent" also means preceding or following and separated by a linker, for example a nucleic acid linker of 6–60 nucleic acids or an amino acid linker of 2–20 amino acids.

The invention also provides for a vector comprising the isolated polynucleotides of the invention.

As used herein, "vector" means a cloning vector that contains the necessary regulatory sequences to allow transcription and translation of a cloned gene or genes.

As used herein, the term "viral vector" refers to a vector that comprises sequence that permits nucleic acid encoding a cloned nucleic acid sequence comprised by the vector to be incorporated into viral particles that are capable of delivering that sequence to a host cell by infection. It is understood in the art that some viral vector systems involve the use of helper virus or packaging cells that provide one or more functions not present on the viral vector comprising the cloned sequence to be delivered. Thus, a viral vector may encode all sequences necessary for viral particle assembly, or it can encode fewer than all such sequences, yet be part of a vector or cell system that directs the packaging of cloned sequence into infective viral particles.

In one embodiment, the vector comprises a plasmid vector, a bacteriophage vector, or a viral vector. In another embodiment, the viral vector comprises an adenoviral vector. In another embodiment, the viral vector comprises a retroviral vector. In another embodiment, the retroviral vector comprises MMLV retroviral sequence. In another embodiment, the viral vector comprises a sequence of one of SEQ ID Nos 33–36.

The invention also provides for a cell comprising the vector of the invention.

The invention also provides for a composition comprising the isolated polynucleotides of the invention.

The invention also provides for a cell infected with a viral vector as described herein.

The invention further encompasses a viral particle comprising a polynucleotide sequence comprising at least two tag sequences, wherein one of the two tag sequences encodes streptavidin-binding peptide having a nucleotide sequence presented in FIG. 1.

The invention further encompasses a viral particle comprising a polynucleotide sequence comprising a gene sequence of interest and at least two tag sequences, wherein the gene sequence of interest is fused in frame with each of the tag sequences, and wherein one of the two tag sequences encodes streptavidin-binding peptide having a nucleotide sequence presented in FIG. 1.

The invention further encompasses a viral particle comprising a polynucleotide sequence comprising at least two tag sequences, wherein one of the two tag sequences encodes streptavidin binding peptide, and wherein one of the two tag sequences encodes calmodulin binding peptide.

The invention further encompasses a viral particle comprising a polynucleotide comprising a gene sequence of interest and at least two tag sequences, wherein the gene sequence of interest is fused in frame with each of the tag sequences, and wherein one of the two tag sequences encodes streptavidin binding peptide, and wherein one of the two tag sequences encodes calmodulin binding peptide.

In one embodiment of the viral particle, both of the tags are adjacent to the N-terminus of the protein of interest.

In another embodiment of the viral particle, both of the tags are adjacent to the C-terminus of the protein of interest.

In another embodiment, the viral particle comprises an adenoviral particle. In another embodiment, the viral particle comprises a retroviral particle. In another embodiment, the retroviral particle comprises nucleic acid encoding a MMLV retroviral sequence. In another embodiment, the viral particle comprises nucleic acid encoding a sequence of one of SEQ ID Nos 33–36.

The invention further encompasses a composition comprising a viral particle as described herein.

The invention also provides for a chimeric protein comprising at least two affinity tags, wherein one of the tags is streptavidin binding peptide having the sequence presented in FIG. 1. The at least two tags are either directly adjacent to each other or are separated by a spacer, as defined herein. Either of the first or second tags can be located N-terminal to the other tag.

The invention also provides for a chimeric protein comprising a protein of interest fused in frame to at least two different affinity tags, one of which is streptavidin binding peptide having the sequence presented in FIG. 1.

The invention also provides for a chimeric protein comprising a streptavidin binding peptide and a calmodulin binding peptide. The tags are either directly adjacent to each other or are separated by a spacer, as defined herein. Either of the first or second tags can be located N-terminal to the other tag.

The invention also provides for a chimeric protein comprising a protein of interest fused in frame to at least two different affinity tags, one of which is streptavidin binding peptide, and wherein one of the affinity tags is calmodulin binding peptide.

In one embodiment, each of the tags are adjacent to the N-terminus of the protein of interest.

In another embodiment, each of the tags are adjacent to the C-terminus of the protein of interest.

As used herein, a "chimera" or "fusion" means a fusion of a first amino acid sequence (protein) comprising a protein product of a gene of interest, joined to a second amino acid sequence encoding a first tag, and joined to at least a third amino acid sequence encoding a second tag. A "chimera" according to the invention contains three or more amino acid sequences (for example a sequence encoding a protein of interest, a sequence encoding calmodulin-binding peptide and a sequence encoding streptavidin-binding peptide) from unrelated proteins, joined to form a new functional protein. A chimera of the invention may present a foreign polypeptide which is found (albeit in a different protein) in an organism which also expresses the first protein, or it may be an "interspecies", "intergenic", etc. fusion of protein structures expressed by different kinds of organisms. The invention encompasses chimeras wherein at least two tag amino acid sequences are joined N-terminally or C-terminally to the protein product of the gene of interest, or wherein a first tag sequence is joined N-terminally and a second tag sequence is joined C-terminally to a protein product of a gene of interest. A "chimera" of the invention includes a protein of interest fused to at least two tags, wherein the tags are located N- or C-terminally, or any combination thereof. The invention also encompasses a chimera wherein one or more of the tag amino acid sequences are fused internally to the amino acid sequence of a protein of interest.

A "chimera" according to the invention also refers to a fusion of a first amino acid sequence comprising a protein product of a gene of interest, joined to at least a second amino acid sequence encoding at least one tag of the invention.

As used herein, "chimeric or fusion protein or polypeptide" refers to a heterologous amino acid sequence of two or more "tag" amino acid sequences fused in frame to the amino acid sequence of interest. In one embodiment, the two or more tag amino acid sequences are fused to the N or C termini of the amino acid sequence of the protein of interest. In one embodiment, a first tag amino acid sequence is fused in frame to the N-terminus of the amino acid sequence of the protein of interest and the second tag amino acid sequence is fused in frame to the C-terminus of the protein of interest. The invention also provides for a first chimeric protein comprising a first tag amino acid sequence fused to a first protein of a complex and a second chimeric protein comprising a second tag amino acid sequence fused to a second protein, wherein the first and second protein are present in the same complex.

The invention also provides for a composition comprising the isolated chimeric proteins of the invention.

The invention also provides for a method of detecting or isolating one or more binding partners for a protein encoded by a gene of interest, comprising the following steps. A gene sequence of interest is cloned into a vector such that the gene of interest is fused in frame with at least two different tag sequences. One of the tag sequences encodes streptavidin binding peptide having the amino acid sequence presented in FIG. 1. The vector is introduced into a cell comprising at least one candidate binding partner. The protein product of the gene of interest and the candidate binding partner are allowed to form a complex in the cell. The complex is isolated by lysing the cells and performing at least one round of affinity purification. The protein complex is then detected.

The invention also provides for a method of detecting or isolating one or more binding partners for a protein encoded by a gene of interest, comprising the following steps. A gene sequence of interest is cloned into a vector such that the gene of interest is fused in frame with at least two different tag sequences. One of the tag sequences encodes streptavidin binding peptide and one of the tag sequences encodes calmodulin-binding peptide. The vector is introduced into a cell comprising at least one candidate binding partner. The protein product of the gene of interest and the candidate binding partner are allowed to form a complex in the cell. The complex is isolated by lysing the cells and performing at least one round of affinity purification. The protein complex is then detected.

In one embodiment, the vector comprises a plasmid vector, a bacteriophage vector, or a viral vector. In another embodiment, the viral vector comprises an adenoviral vector. In another embodiment, the viral vector comprises a retroviral vector. In another embodiment, the retroviral vector comprises MMLV retroviral sequence. In another embodiment, the viral vector comprises a sequence of one of SEQ ID Nos 33–36.

In one embodiment, the cell comprises a vector that expresses at least one candidate binding partner for the protein product of the gene of interest.

In one embodiment the candidate binding partner expresses a tag.

The invention also provides for a method of detecting or isolating a protein complex comprising the following steps. A gene sequence of interest is cloned into a vector such that the gene sequence of interest is fused in frame with at least two different tag sequences. One of the two tag sequences encodes streptavidin binding peptide having the amino acid sequence presented in FIG. 1. The vector is introduced into a cell that expresses at least one protein binding partner for the protein product of the gene sequence of interest. The protein product of the gene of interest and the protein binding partner are allowed to form a complex. The complex is isolated by lysing the cells and performing at least one round of affinity purification.

The invention also provides for a method of detecting or isolating a protein complex comprising the following steps. A gene sequence of interest is cloned into a vector such that the gene sequence of interest is fused in frame with at least two different tag sequences. One of the two tag sequences encodes streptavidin binding peptide and one of the tag sequences encodes calmodulin binding peptide. The vector is introduced into a cell that expresses at least one protein binding partner for the protein product of the gene sequence of interest. The protein product of the gene of interest and the protein binding partner are allowed to form a complex. The complex is isolated by lysing the cells and performing at least one round of affinity purification.

In one embodiment, the vector comprises a plasmid vector, a bacteriophage vector, or a viral vector. In another embodiment, the viral vector comprises an adenoviral vector. In another embodiment, the viral vector comprises a retroviral vector. In another embodiment, the retroviral vector comprises MMLV retroviral sequence. In another embodiment, the viral vector comprises a sequence of one of SEQ ID Nos 33–36.

In one embodiment, the cell comprises a vector that expresses at least one candidate binding partner for the protein product of the gene of interest.

In one embodiment, the candidate binding partner comprises a tag.

In another embodiment, the complex is isolating by performing at least two successive rounds of affinity purification.

As used herein, "protein complex" means two or more proteins or biomolecules that are associated. As used herein, "associated" as it refers to binding of two or more proteins or biomolecules, means specifically bound by hydrogen bonding, covalent bonding, or via an interaction between, for example a protein and a ligand, an antibody and an antigen, protein subunits, or nucleic acid and protein. Under conditions of stable association, binding results in the formation of a protein complex, under suitable conditions, with a dissociation constant, ($K_D$) of at least about $1 \times 10^3$ $M^{-1}$, usually at least $1 \times 10^4$ $M^{-1}$, typically at least $1 \times 10^5$ $M^{-1}$, preferably at least $1 \times 10^6$ $M^{-1}$ to $1 \times 10^7$ $M^{-1}$ or more, for example $1 \times 10^{14}$ $M^{-1}$, $1 \times 10^{16}$, $M^{-1}$, $1 \times 10^{18}$ $M^{-1}$, $1 \times 10^{20}$ $M^{-1m}$, $1 \times 10^{30}$ $M^{-1}$ or more, for each member of the complex. Methods of performing binding reactions between members of a protein complex, as defined herein, are well-known in the art and are described hereinbelow.

As used herein, "form a complex" means to incubate members of a protein complex under conditions, for example, in the presence of the appropriate buffer, salt conditions, and pH, that allow for association of the members of the protein complex. "Form a complex" also means to bind, under suitable conditions, with a dissociation constant ($K_D$) of at least about $1 \times 10^3$ $M^{-1}$, usually at least $1 \times 10^4$ $M^{-1}$, typically at least $1 \times 10^5$ $M^{-1}$, preferably at least $1 \times 10^6$ $M^{-1}$ to $1 \times 10^7$ $M^{-1}$, for example $1 \times 10^{14}$ $M^{-1}$, $1 \times 10^{16}$, $M^{-1}$, $1 \times 10^{18}$ $M^{-1}$, $1 \times 10^{20}$ $M^{-1}$, $1 \times 10^{30}$ $M^{-1}$ or more, or more, for each member of the complex.

As used herein, "affinity purification" means purification of a complex via binding of at least one of the affinity tags of a member of the complex to the ligand for the affinity tag. In one embodiment, the tag is associated with a support material. In a preferred embodiment, the method of the invention utilizes at least two affinity purification steps.

As used herein, "purification resin" or "affinity purification resin" refers to a support material to which a ligand of the invention is immobilized. A "purification resin" according to the invention includes but is not limited to beaded derivatives of agarose, cellulose, polystyrene gels, cross-linked dextrans, polyacrylamide gels, and porous silica.

Further features and advantages of the invention are as follows.

BRIEF DESCRIPTION OF THE DRAWINGS

FIG. 1 shows the sequence of two different CBP/SBP tandem affinity tags. A: SEQ ID Nos 5 (polynucleotide) and 6 (polypeptide); B: SEQ ID Nos 7 (polynucleotide) and 8 (polypeptide).

FIG. 2 is a Table presenting SBP sequences useful according to the invention (SEQ ID Nos 9–28).

FIGS. 3(a) and 3(b) show expression vectors (SEQ ID Nos 29 and 30, respectively) comprising nucleic acids encoding CBP and SBP affinity tags useful according to the invention.

FIGS. 4(a) and 4(b) show expression vectors (SEQ ID Nos 31 and 32, respectively) for expression of a "target" binding partner of the invention.

FIG. 8 shows the result of tandem affinity purification of tandem tagged menin. C2C 12 myoblasts ($2.5 \times 10^7$ cells) were transiently transfected with tandem affinity tagged menin and purified as described herein above. Shown is a Coomassie Blue-stained 4–20% gradient SDS-PAGE gel.

FIG. 9 shows a MALDI-TOF mass spectrometry spectrum for the tandem affinity tagged menin protein isolated from transfected C2C12 cells. Peptides matching those generated from trypsin-digested menin are denoted with an asterisk (*). Protein scores greater than 53 are significant (p<0.05).

DESCRIPTION

Figure 5:
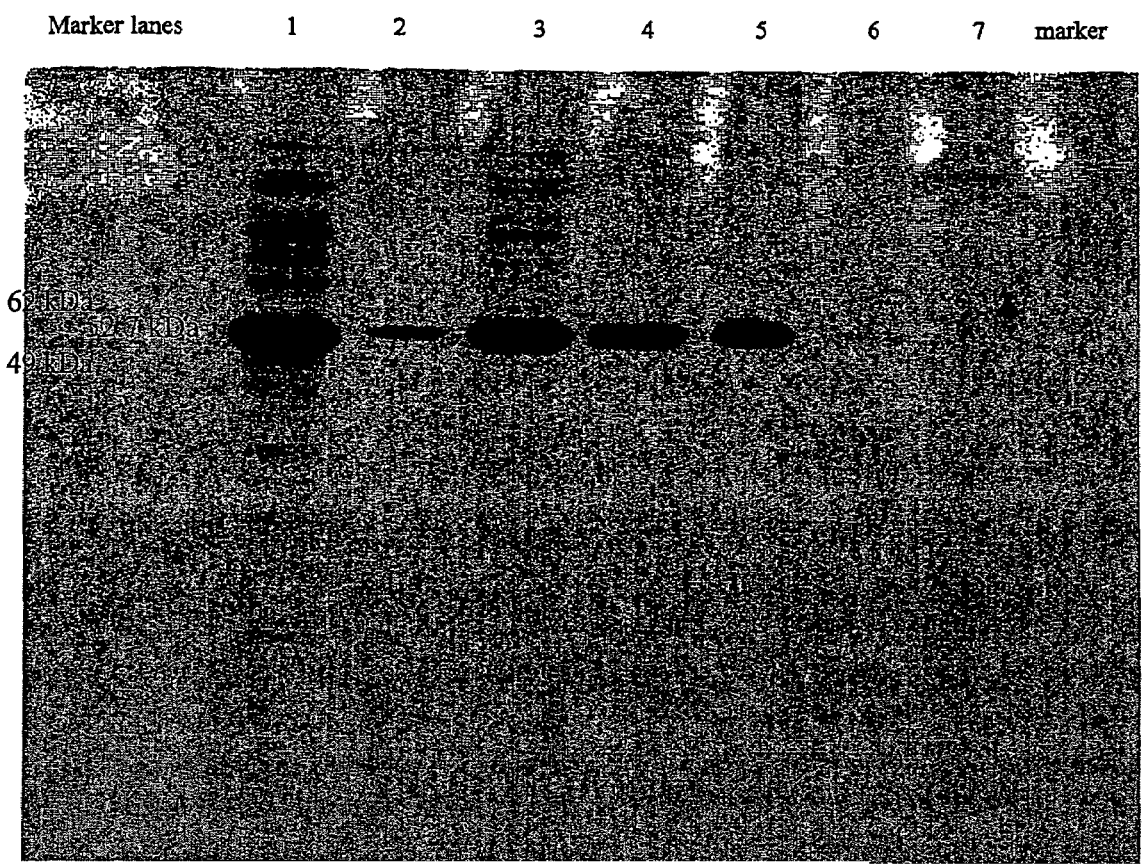
FIG. 5 is a Western blot of affinity purified Mef2c-FLAG.

The invention provides for a method of detecting and/or purifying a protein complex under mild conditions such that the complex is not dissociated. The purification methods described herein allow for isolation of a protein complex that maintains functional activity. The methods described herein also provide for detection of binding partners for a protein of interest. These methods facilitate detection of binding partners for a protein of interest in the absence of prior knowledge of the binding partner(s) or the function of the protein complex. The purification protocol for protein complexes described herein does not require digestion with a protease enzyme. These method provide a simple, generic purification protocol that can be used routinely, and, possibly, in an automated system, for the purification of protein complexes and, for example, for proteome analysis.

Tags

Figure 1:
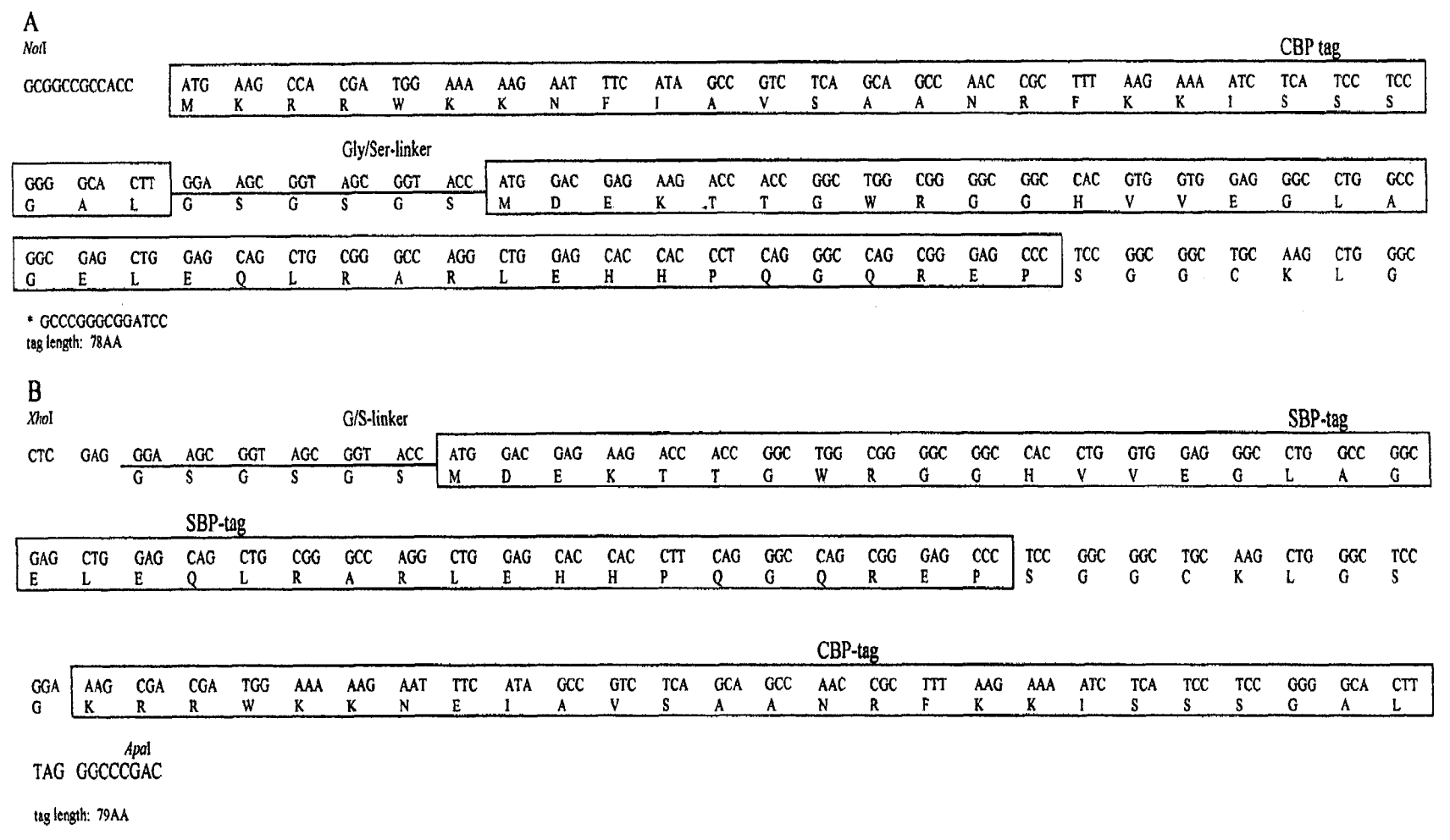

The invention provides an affinity purification tag system comprising an SBP-tag having an amino acid sequence presented in FIG. 1. A second affinity tag includes but is not limited to any of the tags described herein. The invention also provides an affinity purification tag system combining a CBP-tag with an SBP-tag. The invention also provides for an SBP having a sequence presented in any of Luo et al., 1998, J. Biotechnol., 65:225–228; Devlin et al., 1990, Science, 249:404–406; Ostergaard et al., 1995, FEBS Lett, 362:306–308; Gissel et al., 1995, J Pept Sci., 1:217–226; Schmidt et al., 1996, J Mo Biol., 255:753–766; Skerra et al., 1996, Biomol Eng., 16:79–86; Koo et al., 1998, Appl Environ Microbiol., 64: 2490–2496; Aubrey et al., 2001, Biol. Chem., 383: 1621–1628. Preferably, the invention provides for an affinity purification tag system comprising an SBP tag and at least a second affinity tag. Other SBP tags useful according to the invention are presented in FIG. 2, in particular SB1, SB2, SB5, SB9, SB11 and SB12.

Streptavidin has traditionally been used as an affinity tag because it binds biotin with high affinity ($K_d = 10^{-14}$ M) and specificity. Streptavidin will bind biotinylated compounds (such as proteins and nucleic acids) under physiological conditions and the bound compounds are subsequently eluted with biotin. Tagging the targeted protein for streptavidin purification can be achieved by several methods. Biotinylation can be directed to the tagged protein by using domains that are substrates for biotin ligases (de Boer et al., 2003, Proc Natl Acad Sci USA, 100:7480–7485)). However, this approach requires a biotin ligase, which has to be delivered either in vivo or in vitro (de Boer et al., supra). Alternatively, protein tags can be used that have affinity for streptavidin in the absence but not in the presence of biotin and are thus elutable. Two tags with such features have been described: streptag II (Schmidt et al., 1996, J Mol. Biol., 225:753–766) and the streptavidin binding peptide (SBP) (Wilson et al., 2001, Proc Natl Acad Sci USA, 98:3750–3755; Keefe et al., 2001, Protein Expr Purif., 23: 440–446; U.S. 2002/0155578 A1)). SBP has a much higher affinity for streptavidin than streptag II (Wilson et al., supra).

CBP has 26 residues (see FIG. 1) and is derived from the C-terminus of skeletal-muscle myosin light chain kinase, which binds calmodulin with nanomolar affinity in the presence of 0.2 mM $CaCl_2$ (Blumenthal et al., Proc. Natl. Acad Sci USA, 82:3187–3191). In one embodiment of the invention, CBP has the sequence presented in FIG. 1. Additional CBP sequences useful according to the invention include: bovine neuromodulin AA 37–53 KIQASFRGHITRKKLKG (SEQ ID NO: 1; Hinfichsen et al., 1993, Proc. Natl. Acad Sci USA, 90:1585); calmodulin-dependent protein kinase I (CMKI) AA 294–318 SEQIKKNFAKSKWKQAFNATAVVRHMRK (SEQ ID NO: 2); calmodulin-dependent protein kinase II (CMKII) AA 290–309 LKKFNARRKLKGAILTTMLA (SEQ ID NO: 3); and tuberous sclerosis 2 (TSC) WIARLRHIKRLRQRIL (SEQ ID NO: 4; Noonan et al., 2002, Arch, Biochem. Biophys. 389:32).

A purification tag, according to the invention, possesses the following characteristics: (i) the interaction between the tag and the purification matrix is high affinity for example, in the range of $10^3 M^{-1}$ to $10^{14} M^{-1}$; or more (ii) binding occurs under physiological conditions, and does not disrupt the protein-protein interactions of the targeted complex; (iii) elution of the targeted complex from the purification matrix occurs under physiological conditions that do not disrupt the protein-protein interactions; (iv) the binding and elution conditions of the two purification tags are compatible with each other; and (v) the purification tag and the purification matrix have low affinity, for example, less than $10^3 M^{-1}$, for other proteins within the cell lysate to reduce non-specific background.

The invention provides for fusion proteins that are tagged with at least two adjacent tag moieties. In a preferred embodiment, a protein of interest is tagged at the N- or C-terminus with adjacent SBP and CBP tags. Combinations of any of the following tags are also useful according to the invention: calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, Maltose-binding protein, TrxA, DsbA, hemagglutinin epitope, InaD, NorpA, and GFP.

The invention also provides for a first protein that is tagged with at least one of the following tags: calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, Maltose-binding protein, TrxA, DsbA, hemagglutinin epitope, InaD, NorpA, and GFP, in combination with a binding partner or candidate binding partner that is tagged with at least one of the following tags: calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, Maltose-binding protein, TrxA, DsbA, hemagglutinin epitope, InaD, NorpA, and GFP.

The affinity tags may be fused in-frame to a protein of interest such that the tags are directly adjacent to each other, and/or to the protein of interest, or they may be separated from each other and/or from the protein of interest, by a linker (for example of 2–20 amino acids). The order in which the tags are fused with the polypeptide is not critical but can be chosen according to the affinity protocol to be used. Preferably, the tags are located near to the same end of the polypeptide(s). The location of the tag(s) is selected to allow for expression of an appropriate concentration of a correctly folded and processed tagged protein of interest. The tagged protein must not interfere with protein function, cell growth or cell viability.

Small peptides such as CBP or SBP can even be fused to the polypeptide(s) of interest internally (as long as the reading frame of the nucleic acid encoding either the tag or the nucleic acid of interest is maintained).

In one embodiment, at least one affinity tag, for example SBP is fused to a first protein and at least one affinity tag, for example CBP is fused to a second protein of the same complex. This strategy allows the purification of protein complexes containing two given proteins even when only a small fraction of the target proteins are associated, e.g., when large fractions remain free or bound to other complexes.

The invention provides for a method of detecting a binding partner ("target") for a protein of interest ("bait"). According to the method of the invention, a "bait" protein that comprises at least two tags is expressed in a cell with one or more "target" binding partners that comprise at least one different tag. In one embodiment, the bait comprises tandem, adjacent SBP and CBP tags and the binding partner comprises a third tag, for example a FLAG tag. The invention also provides for a binding partner that expresses at least one of any of the following tags: biotin, calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, Maltose-binding protein, TrxA, DsbA, hemagglutinin epitope, InaD, NorpA, and GFP.

Vectors

The invention provides for polynucleotides that can be provided in vectors and used for production of a tagged protein of interest. The tagged protein of interest is used, according to the methods of the invention, to purify a protein complex of interest, and/or to identify binding partners for the protein of interest.

A vector of the invention is designed to maintain expression of the chimeric protein and or candidate binding partner, at, or close to, its natural level. Overexpression of the protein may induce association with nonnatural binding partners. Transcriptional control sequences are therefore selected so that the chimeric protein is not over-expressed but is expressed at basal levels in the cell. For example, a protein of interest is expressed under the control of the endogenous promoter for the protein of interest. This serves to ensure that the protein is expressed in a native form. As used herein, "native form" means that a correct or relatively close to natural three-dimensional structure of the protein is achieved, i.e., the protein is folded correctly. More preferably, the protein will also be processed correctly and correctly modified at both the post-transcriptional and post-translational level. The correct folding is of great importance especially when the expressed polypeptide is a subunit of a protein complex because it will only bind to the other subunits of the complex when it is present in its native conformation. It is also possible to express mutant proteins, according to the methods of the invention. These can also have a native conformation. Such mutant proteins can, for example, be used to purify mutant complexes, i.e., complexes that contain some other mutated protein.

A vector of the invention contains a nucleic acid of interest under the control of sequences which facilitate the expression of the chimeric protein in a particular host cell or cell-free system. The control sequences comprise sequences such as a promoter, and, if necessary enhancers, poly A sites, etc . . . The promoter and other control sequences are selected so that the chimeric protein is preferably expressed at a basal level so that it is produced in soluble form and not as insoluble material. Preferably, the chimeric protein is also expressed in such a way as to allow correct folding for the protein to be in a native conformation. Preferably, one or more selectable markers are also present on the vector for the maintenance in prokaryotic or eukaryotic cells. Basic cloning vectors are described in Sambrook et al., Molecular Cloning, Molecular Cloning, A Laboratory Manual, Cold Spring Harbor Laboratory Press, (1989). Examples of vectors useful according to the invention include plasmids, bacteriophages, other viral vectors and the like. Vectors useful according to the invention are also presented in FIGS. 3 and 4.

In a preferred embodiment, vectors are constructed containing pre-made cassettes of an affinity tag or affinity tag combinations (for example, two or more adjacent tags, wherein a first tag is an SBP tag, for example, having the nucleotide sequence presented in FIG. 1, or two or more adjacent tags, wherein a first tag is an SBP tag and a second tag is a CBP tag) into which the nucleic acid coding the protein of interest can be inserted by means of a multiple cloning site such as a polynucleotide linker. Thus, a vector according to the invention is also one which does not contain the coding sequences for the protein of interest but contains the above-recited vector components plus one or more polynucleotide linkers with preferably unique restriction sites in such a way that the insertion of nucleic acid sequences, according to conventional cloning methods, into one of the sites in the polynucleotide linker, leads to a vector encoding the chimeric protein of the invention. Unique restriction enzyme sites located upstream and downstream of the tag or tags of the invention, facilitate cloning of a target protein of interest such that the tag or tags are located N- or C-terminally, or internally in the protein of interest.

In a further preferred embodiment, the vector comprises heterologous nucleic acid sequences in the form of two or more cassettes each comprising at least one of two different affinity tags, one of which is an SBP tag, for example, having the nucleotide sequence presented in FIG. 1, and at least one polynucleotide linker for the insertion of further nucleic acids. Alternatively, a vector of the invention comprises heterologous nucleic acid sequences in the form of two or more cassettes each comprising at least one of two different affinity tags, one of which is an SBP tag and one of which is a CBP tag. Such vectors can be used to express two subunits of a protein complex, each tagged with a different tag.

The invention provides for expression vectors that express the protein product of a gene of interest fused in frame to tandem tags. The tandem tags are fused in frame to either the N or C-terminus of the protein of interest. In one embodiment, a first tag is fused in frame to the N-terminus, and a second tag is fused in frame to the C-terminus of the protein of interest. Alternatively, one or more tags of the invention are fused internally to a protein of interest.

In a preferred embodiment, the invention provides for a CMV vector. The invention provides for regulatable expression systems that provides for expression of the chimeric protein at a level that is, preferably, equivalent to the level of expression of the endogenous protein. In one embodiment the regulatable expression system is an ecdysone regulated expression system (Complete Control, Stratagene, No.: 217468). In another embodiment, the system is regulatable due to the inclusion of aptamer sequences in the 5' untranslated region of, for example, the gene of interest (as described in Werstuck et al., 1988, *Science*, 282:296; Harvey et al., 2002, *RNA*, 8: 452; Hwang et al., 1999, *Proc Natl Acad Sci USA*, 96:12997).

In another embodiment, a viral vector system can be employed to increase the transformation efficiency, especially, but not necessarily, the efficiency of transduction of mammalian cell lines. Viral vectors include, for example, adenoviral vectors, for which transduction efficiencies commonly equal or approach 100%. Adenoviral vectors can be particularly useful for the introduction of tagged fusion proteins into primary cells and cells that are difficult to transfect. Adenoviral vector systems suitable for delivering tandem affinity-tagged vector constructs to cells are well known and available commercially (e.g., the AdEasy™ Adenoviral Vector System (Stratagene), and the Adeno-X series (Clontech)). Adenoviruses have a broad tropism based on their binding to cellular receptors that are expressed in many different cell types. For example, the vectors based on Adenovirus type 5 (Ad5) bind to the coxsackievirus and adenovirus receptor (CAR) and the integrin alpha-gamma-β1 receptor. These receptors are expressed in many different cell types, but at different levels. The efficiency of adenoviral infection depends on the numbers of receptors found on the particular cells being infected (see Methods in Molecular Medicine, Vol 76: Viral Vectors for Gene Therapy: Methods and Protocols. (2003) Edited by C A Machida, Human Press Inc., Totowa, N.J.). Adenoviral vectors, unlike some vectors, do not require that their target cells be mitotically active, making them suitable for transduction into quiescent cell populations, where desired.

Additional viral vectors include, for example, those based on SV40, adeno-associated virus, herpes virus vectors and retroviral vectors. Retroviral vectors are most frequently based upon the Moloney murine leukaemia virus (Mo-MLV), which is an amphotrophic virus, capable of infecting both mouse cells, enabling vector development in mouse models, and human cells. Numerous retroviral vectors are known in the art and available commercially, from, for example, Stratagene, BD Biosciences Clontech, Invitrogen, etc. Additional viral vectors useful in, for example, mammalian cell systems, are described in Methods in Molecular Medicine, 76: Viral Vectors For Gene Therapy: Methods and Protocols, 2003, supra.

Vectors useful according to the invention include CMV vectors wherein a CBP and a SBP tag are fused to the N or C terminus of the bait protein in each of the three possible reading frames. Vectors useful for expressing a CBP-SBP tagged protein of the invention are presented in FIG. 3.

Vectors useful for expressing a FLAG tagged protein of the invention are presented in FIG. 4 and are available from Stratagene.

Construction of vectors according to the invention employs conventional ligation techniques. Isolated plasmids of DNA fragments are cleaved, tailored and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art.

Gene presence, amplification and/or expression may be measured in a sample directly, for example, by conventional Southern blotting, Northern blotting to quantitate the transcription of mRNA, dot blotting (DNA or RNA analysis), PCR, RT-PCR, Q-PCR, RNase Protection assays or in situ hybridization, using an appropriately labeled probe based on a sequence provided herein. Those skilled in the art will readily envisage how these methods may be modified, if desired. Standard DNA cloning procedures are, therefore, used to introduce the N or C terminal tandem tags in frame with the coding region of the protein of interest in an appropriate expression vector.

Cells

A vector of the invention can be introduced into an appropriate host cell. These cells can be prokaryotic or eukaryotic cells, e.g., bacterial cells, yeast cells, fungi or mammalian cells, and the vector or nucleic acid can be introduced (transformed) into these cells stably or transiently by conventional methods, protocols for which can be found in Sambrook et al. (supra).

DNA may be stably incorporated into cells or may be transiently expressed using methods known in the art (see Sambrook et al., supra). Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene of interest, to monitor transfection efficiency. In one embodiment, the bait vector is introduced via infection using a viral vector such as adenoviral vectors, AAV vectors, retroviral vectors or lentiviral vectors.

Vectors of the invention can be present extrachromosomally or integrated into the host genome, and used to produce recombinant cells or organisms such as transgenic animals.

Tagged Protein

The polynucleotides of the invention are useful for production of a tagged protein of interest. The tagged protein can be tagged at the N- or C-terminus, or a combination thereof, with one or more affinity tags as described herein. The tagged protein is used to purify a complex comprising the protein of interest and/or to identify binding partners for the protein of interest.

Complex of the Invention

The invention provides for methods of detecting and isolating a complex of the invention. A complex of the invention may comprise a complex of proteins or a complex of biomolecules, as defined herein. A complex of the invention comprises a protein of interest.

As used herein, "protein of interest" means any protein for which the nucleic acid sequence is known or available, or becomes available, such that it can be cloned into a nucleic acid vector which is suitable for expression in the appropriate host cells or cell-free expression systems. For purification of a protein complex, the nucleic acid sequence of at least one of the subunits of the protein complex must be known or available.

Proteins useful according to the invention include but are not limited to:

1) cell cycle regulatory proteins (for example cyclins, cdks, Rb, E2F, regulators of cyclins including p21);

2) protein complexes involved in regulating intracellular transport (for example nuclear transport channels, transport into Golgi, transport into mitochondria);

3) proteins involved in the regulation of gene expression (for example transcription factors (e.g., p53, myc), transcription complexes (e.g., TATA binding protein complexes); transcriptional modulators (for example histone acetylases and histone deacetylases); components of snRNPs (involved in splice junction recognition); polyadenylation complexes; regulators of nuclear export of nucleic acids; RISC complex (components of the RNAi pathway);

4) growth factor receptors (EGFR, IGFR, FGFR);

5) regulators of the cytoskeleton (for example components of the focal adhesion complexes (paxillin, focal adhesion kinase); regulators of actin organization (racB);

6) viral proteins interacting with host proteins (for example EBNA2, EBNA1 of EBV, E1A/E1B of adenovirus, E6 and E7 of HPV);

7) proteins of pathogenic bacteria that bind to mammalian host cells; and 8) proteins in complexes that mediate cell/cell interactions (for example gap junctions (connexin).

A protein of interest useful according to the invention also includes lipoproteins, glycoproteins, phosphoproteins. Proteins or polypeptides which can be analyzed using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens and bacterial antigens. Specific examples of these compounds include proinsulin (GenBank #E00011), growth hormone, dystrophin (GenBank # NM_007124), androgen receptors, insulin-like growth factor I (GenBank #NM_00875), insulin-like growth factor II (GenBank #X07868) insulin-like growth factor binding proteins, epidermal growth factor TGF-α (GenBank #E02925), TGF-β (GenBank #AW008981), PDGF (GenBank #NM_002607), angiogenesis factors (acidic fibroblast growth factor (GenBank #E03043), basic fibroblast growth factor (GenBank #NM_002006) and angiogenin (GenBank #M11567), matrix proteins (Type IV collagen (GenBank #NM_000495), Type VII collagen (GenBank #NM_000094), laminin (GenBank # J03202), phenylalanine hydroxylase (GenBank #K03020), tyrosine hydroxylase (GenBank #X05290), oncogenes (ras (GenBank #AF 22080), fos (GenBank #k00650), myc (GenBank #J00120), erb (GenBank #X03363), src (GenBank #AH002989), sis GenBank #M84453), jun (GenBank #J04111)), E6 or E7 transforming sequence, p53 protein (GenBank #AH007667), Rb gene product (GenBank #m19701), cytokine receptor, Il-1 (GenBank #m54933), IL-6 (GenBank #e04823), IL-8 (GenBank #119591), viral capsid protein, and proteins from viral, bacterial and parasitic organisms which can be used to induce an immunologic response, and other proteins of useful significance in the body.

The compounds which can be incorporated are only limited by the availability of the nucleic acid sequence for the protein or polypeptide to be incorporated. One skilled in the art will readily recognize that as more proteins and polypeptides become identified they can be integrated into the DNA constructs of the invention and used to transform or infect cells useful for producing an organized tissue according to the methods of the present invention. Therefore, a protein of interest includes the protein product of any open reading frame included in GenBank.

Protein Expression

Depending on the protein to be purified, the chimeric protein is expressed intracellularly or secreted into the culture medium. Alternatively, it might be targeted to other cell compartments such as the membrane. Depending on the protein, an appropriate method is used to extract the chimeric protein from the cells and/or medium. When a chimeric protein is expressed and targeted to a particular subcellular location, e.g., the membrane of cell organelles or the cell membrane, these organelles or the cells themselves can be purified via the binding of these membrane proteins. It is also possible to purify cells or cell organelles via proteins naturally expressed on their surface which bind to the chimeric protein of the invention.

According to the invention it is also possible to use cell-free systems for the expression of the protein of interest. These must provide all the components necessary to effect expression of proteins from the nucleic acid, such as transcription factors, enzymes, ribosomes etc . . . In vitro transcription and translation systems are commercially available as kits so that it is not necessary to describe these systems in detail (e.g. rabbit reticulocyte lysate systems for translation). A cell-free or in vitro system should also allow the formation of complexes.

Protein Isolation

Various extraction procedures known in the art, and known to be compatible with purification of a protein of interest are used to prepare extracts from cells or organisms expressing the tagged target protein. Cell fractionation and/or tissue dissection can facilitate purification by providing a preenrichment step or can be used to assay specifically protein complex compositions in various tissues or cell compartments.

An extraction procedure that is useful according to the invention does not interfere with the interaction of the bait and the target proteins. For example, extraction is preferably performed in the absence of strong detergents and reducing agents, or any agent that may induce protein denaturation.

A protein extract is prepared from an appropriate cell type by first exposing the cell to either mechanical and/or chemical disruption. Mechanical disruption may include electric homogenizers, blenders, "Dounce" homogenizers, and sonicators. Chemical disruption of cells usually occurs with the use of detergents that solubilize cell membranes resulting in cell lysis.

Protease inhibitors and phosphatase inhibitors are routinely added to cell lysates, at concentrations well known in the art, to prevent proteolysis. Centrifugation is performed to separate soluble from insoluble protein and membranes, and both fractions are processed separately. Nucleic acid contaminants are usually removed from the soluble protein extract by first shearing the nucleic acid polymers or treating with DNase or a combination of DNase and RNase. Protamine sulfate or polyethylene imine are added in various concentrations, known in the art, followed by centrifugation, resulting in a compact pellet of nucleic acid and protamine sulfate or polyethylene imine. This pellet is then discarded. The soluble protein extract is now ready for further processing.

The insoluble protein fraction described above can be solubilized with a variety of detergents, known in the art, and membrane proteins and analyzed.

Affinity Purification

The invention provides for a chimeric protein that comprises an affinity tag, and preferably at least two affinity tags. The presence of a second affinity tag is used to increase the purity following a second affinity chromatography step.

Methods of affinity purification useful according to the invention are well known in the art and are found on the world wide web at urich.edu/~jbell2/CHAPT3.html.

For purification according to the invention it is preferable to employ affinity chromatography using a matrix coated with the appropriate binding partner or "ligand" for the affinity tag used in that particular purification step.

A matrix material for use in affinity chromatography according to the invention has a variety of physical and chemical characteristics that give it optimal behavior. In terms of its physical properties it should have a high porosity, to allow maximum access of a wide range of macromolecules to the immobilized ligand. It should be of uniform size and rigidity to allow for good flow characteristics, and it must be mechanically and chemically stable to conditions used to immobilize the appropriate specific ligand. In terms of its chemical properties, it should have available a large number of groups that can be derivatized with the specific ligand, and it should not interact with proteins in general so that nonspecific adsorption effects are minimized.

A diverse variety of insoluble support materials are useful according to the invention, including but not limited to agarose derivatives, cellulose, polystyrene gels, cross-linked dextrans, polyacrylamide gels, and porous silicas, and beaded derivatives of agarose.

Methods of immobilizing a ligand of the invention onto a support matrix are provided on the world wide web at urich.edu/~jbell2/CHAPT3.html.

In accordance with the preferred embodiment of the invention, to purify a complex comprising a chimeric protein with two affinity tags, two affinity purification steps are carried out. Each affinity step consists of a binding step in which the extracted protein is bound via one of its affinity tags, to a support material which is covered with the appropriate binding partner for that affinity tag. Unbound substances are removed and the protein to be purified is recovered from the support material. This can be done in at least two ways. Conventional elution techniques such as varying the pH, the salt or buffer concentrations and the like depending on the tag used, can be performed Alternatively, the protein to be purified can be released from the support material by proteolytically cleaving off the affinity tag bound to the support. If the cleavage step is performed, the protein can be recovered in the form of a truncated chimeric protein or, if all affinity tags have been cleaved off, as the target polypeptide itself.

In one embodiment, biotin is added and competes for streptavidin binding sites occupied by SBP. EGTA is also added to complex with $Ca^{2+}$, thus disrupting the interaction between CBP and calmodulin. In other embodiments, other small molecules are added, and compete for binding sites on the affinity ligand, thereby dissociating bound protein complexes.

Elution conditions are preferably mild so that the interaction of the bait and the target is not disrupted. Preferably, non-physiological salt or pH conditions are avoided.

In one embodiment, non-specific binding proteins that naturally interact with calmodulin or streptavidin (for example naturally biotinylated proteins) are removed in a pre-purification step by incubation with avidin to bind biotinylated but not SBP tagged protein.

Protein Detection

Proteins associated with the tagged protein of interest are detected by a variety of methods known in the art.

Proteins are analyzed by SDS-polyacrylamide gel electrophoresis (SDS-PAGE) and stained (either by Coomassie or by silver staining). Bands of interest are excised from the gel, and analyzed by mass spectrometry (for example as described in Honey et al., supra), either directly or following in-gel digestion, for example, with trypsin.

Associated proteins can also be identified by Western blot analysis or co-immunoprecipitation.

In certain embodiments, the eluate fraction from the affinity purification step(s) is concentrated, for example by TCA precipitation (Puig et al. supra) prior to analysis by SDS-PAGE.

Kits

The invention herein also contemplates a kit format which comprises a package unit having one or more containers of the subject vectors of the invention. The kit may also contain one or more of the following items: primers, buffers, affinity purification resins, instructions, and controls. Kits may include containers of reagents mixed together in suitable proportions for performing the methods in accordance with the invention. Reagent containers preferably contain reagents in unit quantities that obviate measuring steps when performing the subject methods.

The vectors of the kit are provided in suitable packaging means, for example in a tube, either in solution in an appropriate buffer or in a lyophilized form.

Uses

The invention provides reagents and methods for identifying one or more protein binding partners or ligands that interact, either directly or indirectly, with a protein of interest.

The invention also provides for methods of detection and/or identification of a protein complex comprising two or more proteins or biomolecules.

The invention also provides a method of analyzing the structure and/or activity of a purified complex of one or more proteins or biomolecules. In particular, the method can be used to determine the approximate stoichiometry of proteins in a given complex.

The methods of the invention are also useful for purification of a protein complex, without disruption of the complex.

The methods of the invention can also be used to identify proteins or biomolecules present in a complex.

The methods of the invention are also useful for identification of one or more binding partners for a protein of interest.

The polynucleotides of the invention are useful for producing a tagged protein of interest.

Having now generally described the invention, the same will be more readily understood through reference to the following Examples which are provided by way of illustration, and are not intended to be limiting of the present invention, unless specified.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

EXAMPLES

Example 1

Construction of a Tandem Affinity Tag Vector

The invention provides for vectors that express a tandem affinity tagged protein wherein the affinity tags are positioned either at the C- or N-terminus of a protein of interest. CMV-driven mammalian expression vectors with tandem SBP and CBP tags, that express a protein of interest wherein the tags are positioned either at the N-terminus of the C-terminus of the protein are constructed. Nucleotide and amino acid sequences of SBP and CBP tags are provided in FIG. 1. Polynucleotides and vectors useful for construction of a tandem affinity tagged protein of interest are presented in FIG. 3.

All buffers described in the following examples are described in Example 3.

The open reading frames of the transcription factors MEF2a and MEF2c (Myosin Enhancing Factor) were cloned into the CMV-driven expression vectors described above, resulting in addition of CBP and SBP-tags either at the N-terminus or at the C-terminus of the tagged protein. These constructs act as the bait to co-purify interacting proteins. MEF2a and MEF2c were chosen because their interaction has previously been demonstrated to be detectable using a CBP/proteinA-based tandem affinity purification system (Cox et al., 2002, *Biotechniques*, 33:267–270; Cox et al., 2003, *J. Biol. Chem.*, 278:15297–15303). Since members of the MEF2 family can dimerize with each other (forming homo- and hetero-dimers), MEF2a as well as MEF2c were inserted in mammalian expression vectors containing the FLAG-tag (for example as in FIG. 4) as a fusion to either the N-terminus or the C-terminus of MEF2 and MEF2c, for immunodetection. These vectors provided the "target" protein in the purification procedure. The bait vectors containing either MEF2a or MEF2c were co-transfected with the target expression vectors (either Flag-tagged MEF2a or MEF2c) into COS-7 cells (as described below). MEF2a bait protein complexed with target MEF2c and MEF2c bait protein complexed with target MEF2a were purified using the tandem affinity purification reagents and purification procedure described below. Protein complexes were characterized by Western blotting and mass spectrometry.

Example 2

Expression of a Tandemly Tagged Protein

A tandemly tagged protein of interest was expressed as follows.

COS-7 cells were grown in DMEM media with 10% FBS and antibiotics (Pen/Strep) in T175 flasks overnight to 50–60% confluency. Media was aspirated and 25 ml of fresh media was added before transfection. 30 μg of MEF2a-CBP-SBP and 30 ug of MEF2c-FLAG plasmids were diluted in 1.5 ml of serum-free DMEM media. 120 μl of Lipofectamine 2000 was diluted in 1.5 ml of serum-free DMEM media and incubated for 5 min at room temperature. The DNA and LF2000 solutions were combined and incubated for 20 min at room temperature. 3 mls of DNA-lipid complex was added to the cells and incubated at 37° C. for 48 hr. Cells were washed three times with PBS. 5 ml of ice-cold PBS was then added to each flask, and the cells were scraped and transferred to a 15 ml conical tube. The cells were centrifuged at 1500×g for 10 minutes. The PBS was aspirated and 1 ml of lysis buffer (described below) was added. Lysed cells were stored at −80° C. Cells from four to eight T175 flasks were used for each experiment.

Example 3

Purification of a Protein Complex

A protein complex comprising a tandemly tagged protein of interest and its binding partner was purified according to the following method.

All steps were performed at 4° C. Approximately 1×10$^7$ cells (1×T175 flask) (prepared as described in example 2) were freeze thawed for 3 cycles in 1 ml lysis buffer. The cells were centrifuged to pellet cell debris for 10 min at 16,000 g. The cleared lysates from 4–8 flasks were pooled in a fresh tube. A 5 μl sample was reserved and frozen for Western Blot analysis. To the remainder of the pooled lysate was added EDTA to a concentration of 2 mM, and β-mercaptoethanol to a concentration of 10 mM (4 μl of 0.5 M EDTA, and 0.7 μl of 14.4 M βME, for each 1000 μl of lysate) resulting in the lysates being contained in Streptavidin Binding Buffer.

100 μl of Streptavidin beads (50% slurry) for each 1 ml of lysate were washed in SBB to remove the ethanol storage buffer as follows. Beads for multiple 1 ml lysate preps were pooled and washed together in 1 ml of SBB. Beads were collected by centrifugation at 1500 g for 5 minutes. The SBB wash supernatant was removed from the beads and the beads were resuspended a second time in 1 ml of the indicated binding buffer. The beads were collected by centrifugation at 1500 g for 5 minutes and resuspended in SBB (i.e., 100 µl SBB for each 100 µl aliquot of beads required).

100 µl of washed Streptavidin beads were added to 1 ml of lysate. The tubes were rotated for 2 hr at 4° C. to allow proteins to bind to the beads. The beads were washed twice with SBB as described above. The tubes were rotated for 5 min at 4° C. to resuspend beads between centrifugations. After the final centrifugation step, SBB was removed from the pelleted beads.

100 µl of Streptavidin Elution Buffer (SEB) was added to the pelleted beads. The tubes were rotated for 30 min at 4° C. to elute protein complex/es. The beads were pelleted by centrifugation at 1500 g for 5 minutes. The supernatant containing the eluted proteins was carefully collected and transferred to a fresh tube. A 10 µl sample from the supernatant was reserved for Western Blot analysis.

2 µl of supernatant supplement (50 mM Magnesium acetate, 50 mM Imadozole, 100 mM Calcium chloride) was added per 100 µl of supernatant such that the eluted proteins were now suspended in Calmodulin Binding Buffer (CBB). An additional 900 µl of CBB was added to the eluted proteins. For each 1 ml of eluted proteins in CBB, 100 µl of Calmodulin Affinity Resin (50% slurry) was added. (Resin for multiple 1 ml preps was pooled and washed together in 1 ml of CBB. The resin was pelleted by centrifugation at 1500 g for 5 minutes and resuspended to the original volume of 100 µl in CBB. 100 µl of washed Calmodulin Affinity Resin was added per 1 ml of eluted proteins). The tubes were rotated for 2 hr at 4° C. to allow proteins to bind to the resin. The resin was washed twice with CBB as above. The tubes were rotated for 5 min at 4° C. to resuspend the resin between centrifugations. After the last centrifugation step, the binding buffer was removed from the pelleted resin.

100 µl of Calmodulin Elution Buffer (CEB) was added to the pelleted Calmodulin Affinity Resin. The tubes were rotated for 30 min at 4° C. to elute proteins. The resin was pelleted by centrifugation at 1500 g for 5 minutes. The supernatant was carefully collected and transferred to a fresh tube. This supernatant contained the affinity purified protein complex/es.

The compositions of the buffers used in the examples presented herein are described below.

Lysis Buffer:
10 mM Tris, pH 8.0
150 mM NaCl
0.1% Nonidet P-40
Add 10 µl of the protease inhibitor cocktail (Sigma, Cat.# p8340) and 10 µl of 100 mM PMSF per 1 ml of lysis buffer before use.

| Streptavidin binding buffer (SBB) 250 ml | | |
|---|---|---|
| 10 mM Tris, pH 8.0 | 2.5 ml | 1 M Tris |
| 150 mM NaCl | 7.5 ml | 5 M NaCl |
| 0.1% Nonidet P-40 | 2.5 ml | 10% NP40 |
| 2 mM EDTA | 1 ml | 0.5 M EDTA |
| H$_2$O | to 250 ml | |
| 10 mM 2-mercaptoethanol (ME) | Add 7 µl ME per 10 ml before use | |
| Streptavidin elution buffer (SEB): SBB + 2 mM biotin. 25 ml | | |
| 10 mM Tris, pH 8.0 | 0.25 ml | 1 M Tris |
| 150 mM NaCl | 0.75 ml | 5 M NaCl |
| 0.1% Nonidet P-40 | 0.25 ml | 10% NP40 |
| 2 mM biotin | 500 µl | 0.1 M biotin |
| H$_2$O | to 25 ml | |
| 10 mM 2-mercaptoethanol | Add 7 µl ME per 10 ml before use | |
| Supernatant Supplement 1 ml | | |
| 50 mM Magnesium Acetate | 100 µl | 0.5 M Magnesium Acetate |
| 50 mM Imidazole | 50 µl | 1 M Imidazole |
| 100 mM Calcium chloride | 100 µl | 1 M Calcium chloride |
| H$_2$O | to 1 ml | |
| Calmodulin binding buffer (CBB) 250 ml | | |
| 10 mM Tris, pH 8.0 | 2.5 ml | 1 M Tris |
| 150 mM NaCl | 7.5 ml | 5 M NaCl |
| 0.1% Nonidet P-40 | 2.5 ml | 10% NP40 |
| 1 mM magnesium acetate | 0.5 ml | 0.5 M MgAce |
| 1 mM imidazole | 250 µl | 1 M Imidazole |
| 2 mM CaCl$_2$ | 0.5 ml | 1 M CaCl$_2$ |
| H$_2$O | to 250 ml | |
| 10 mM 2-mercaptoethanol | Add 7 µl ME per 10 ml before use | |
| Calmodulin elution buffer (CEB) 25 ml | | |
| 10 mM Tris, pH 8.0 | 0.25 ml | 1 M Tris |
| 150 mM NaCl | 0.75 ml | 5 M NaCl |
| 0.1% Nonidet P-40 | 0.25 ml | 10% NP40 |
| 1 mM magnesium acetate | 50 µl | 0.5 M MgAce |
| 1 mM imidazole | 25 µl | 1 M Imidazole |
| 5 mM EGTA | 250 µl | 0.5 M EGTA |
| H$_2$O | to 25 ml | |
| 10 mM 2-mercaptoethanol | Add 7 µl ME per 10 ml before use | |

Example 4

Detection of a Protein Complex

A protein complex comprising a tandemly tagged protein of interest was detected.

Immunodetection

FIG. 5 represents a Western blot of MEF2c-FLAG protein isolated according to the method of the invention, using the protocol described above. The data demonstrates that SBP/CBP-tagged MEF2a forms a complex with MEF2c-FLAG and that these proteins co-purify using the streptavidin and calmodulin affinity purification resins (lanes 4 and 7, respectively), as detected by the anti-FLAG antibody.

Affinity purified, isolated MEF2c was detected with an anti-Flag antibody hybridized to samples taken from each step of the affinity purification procedure. Cos-7 cells were co-transfected with two vector constructs. The first vector was MEF 2A with N-terminal tags Streptavidin Binding Peptide (SBP) and Calmodulin Binding Peptide (CBP). The second vector was MEF 2C with a FLAG peptide as an N-terminal tag. Cell lysates were prepared as described above. Lane 1 is 10 µl of lysate from 1×10$^7$ Cos-7 cells lysed in 1 ml of buffer. This lane shows the expression of the FLAG tag in the lysate. Lane 2 is 10 µl out of 100 µl of Streptavidin Beads after incubation and elution. This lane shows the material that remains on the beads after processing. Lane 3 is 10 µl of the 1000 µl of lysate after it has been incubated with the Streptavidin beads. This lane shows the material that is not bound by the beads. Lane 4 is 10 µl out of 100 µl of elution buffer used to elute proteins from the Streptavidin beads. This lane shows the MEF2a-MEF2c protein complex that is eluted from the streptavidin beads. Lane 5 is 10 µl out of 100 µl of Calmodulin beads after incubation and elution. This lane shows the proteins that remain on the beads after processing. Lane 6 is 10 µl of 1000 µl of material after incubation with Calmodulin Beads. This lane shows the proteins that are not bound by the Calmodulin beads. Lane 7 is 17 µl out of 100 µl of elution buffer used to elute the MEF2a-MEF2c protein complex from the Calmodulin beads. This is the final affinity purified protein complex.

Detection of MEF2 and -MEF2c by Staining

Figure 6:
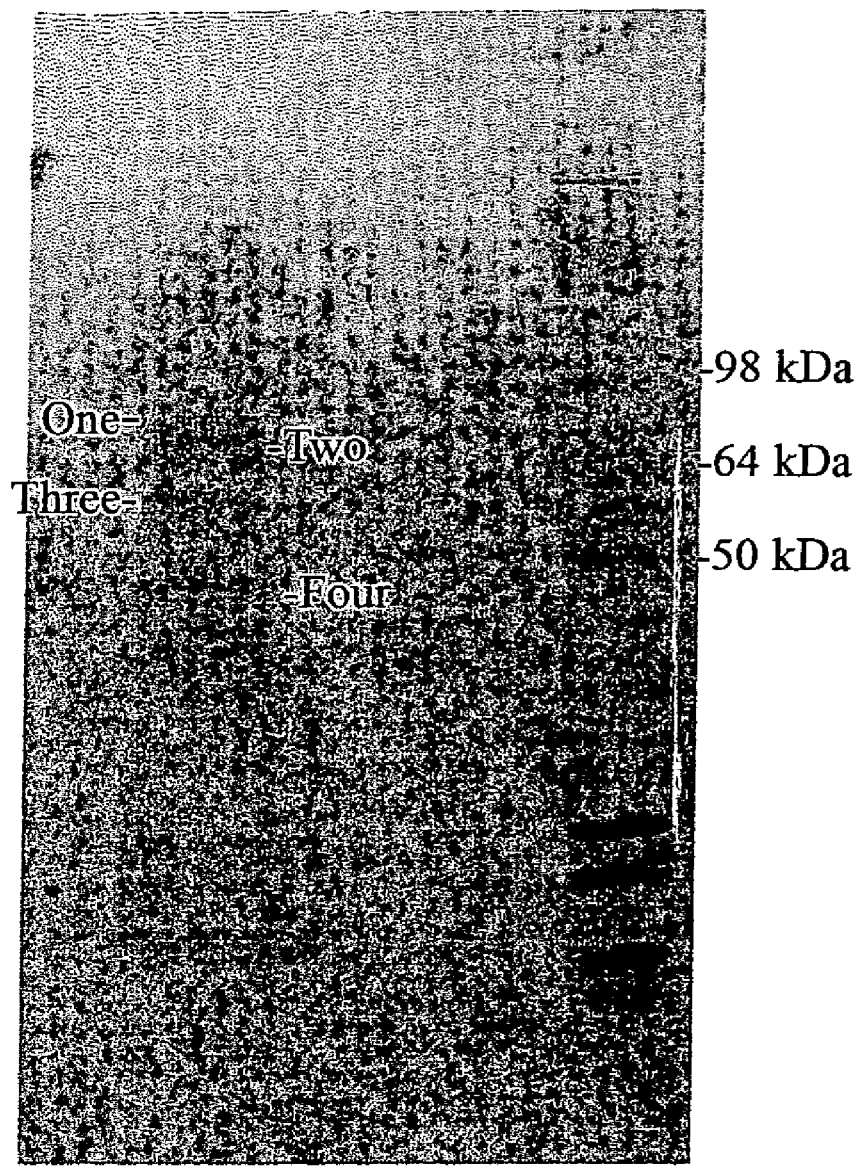
FIG. 6 is a Tris-glycine acrylamide gel of affinity purified Mef2A/Mef2c.

FIG. 6 shows a 4–20% Tris-glycine acrylamide gel of affinity purified MEF2a/MEF2c, stained with Commassie Brilliant Blue. The right lane shows molecular weight markers. The lane on the left is affinity purified MEF2a-SBP/CBP and MEF2c-FLAG from $5 \times 10^7$ Cos-7 cells, co-transfected with vectors expressing these tagged proteins. Protein bands labeled "One" through "Four" were excised for mass spectroscopy analysis. Mass spectrometer data analysis identifies protein in bands "One" and "Two" as MEF 2A (MOWSE scores 56 and 85, respectively). Protein band "Three" is identified as MEF 2C (MOWSE score of 78). Protein band "Four" is identified as Actin (MOWSE score 175). MOWSE scores greater than 68 represent positive identification of the protein of interest.

Example 5

Tandem Affinity-Tagged Fusions to Examine Protein-Protein Interactions with Menin The tumor suppressor protein menin is a primarily nuclear protein of 610 amino acids that is involved in the regulation of gene transcription, cell proliferation, and genome stability. menin inactivates the Jun D component of the AP-1 transcription complex. Identification of menin-interacting proteins could provide new insights into the function of menin in the tumor-suppression mechanism. To study menin interacting protein partners, a tandem affinity tagged fusion protein as described herein was generated for menin.

A. Intracellular Localization of Tandem Affinity Tagged-Menin.

Figure 7:
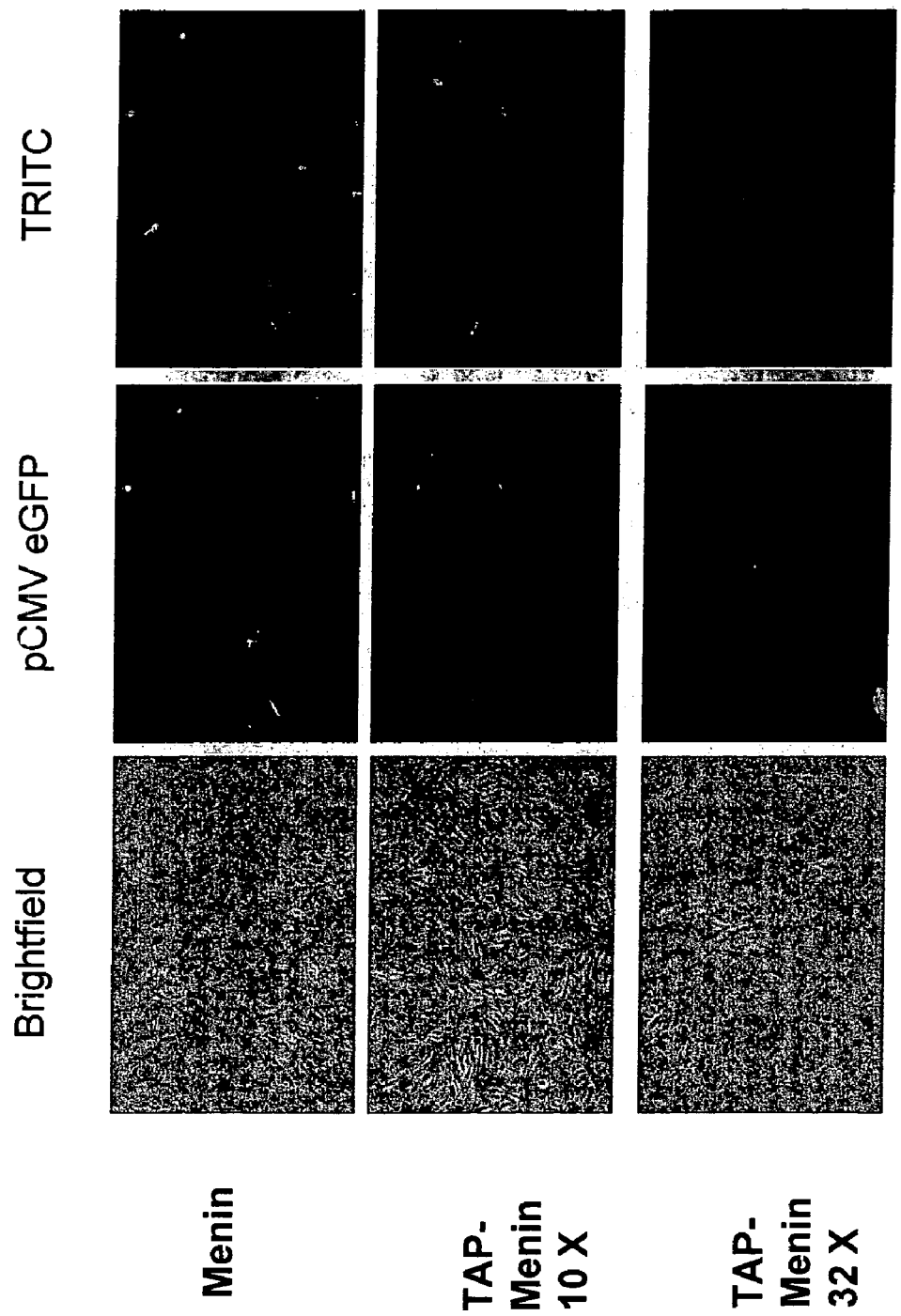
FIG. 7 shows the expression and intracellular localization of tandem affinity tagged menin in C2C12 myoblasts. Cells were transfected with 1 μg of pEGFP-N1 and 10 μg of either pCDNA3 (not shown), pCMV menin or pNTAP menin (encoding amino-terminally tagged menin). Cells were fixed 40 hours post-transfection and immunofluoresence staining was performed to detect expression of menin. The staining patterns for wild-type and tandem affinity tagged menin were the same.

C2C12 myoblasts were transfected with a construct encoding the expression of tandem affinity-tagged menin bearing CBP and SBP tags, and intracellular localization of the tagged menin and endogenous menin were compared. Cells were transfected with 1 μg of pEGFP-N1 and 10 μg of either pCDNA3 (not shown), pCMV menin or pNTAPmenin (encoding amino-terminally tagged menin). Cells were fixed 40 hours post-transfection and immunofluoresence staining was performed to detect expression of menin. As shown in FIG. 7, perinuclear and nuclear staining were observed for wild type and tandem tagged menin. The result showed that menin is expressed in skeletal muscle during differentiation and that the tandem tagged menin has an identical cellular localization as endogenous menin protein.

B. Purification of Tandem Affinity Tagged Menin.

Tandem affinity-tagged menin was successfully purified from C2C12 cells ($2.5 \times 10^7$ cells) transiently transfected with pNTAP-Menin by sequential binding to streptavidin and calmodulin resins as described above in Example 4. Results of one experiment are shown in the Coomassie Blue-stained 4–20% SDS-PAGE gel shown in FIG. 8. Additional co-purifying bands have been observed in other experiments.

C. Identification of Menin by MALDI-TOF Mass Spectrometry.

Purified protein was positively identified by MALDI-TOF mass spectrometry as Menin (FIG. 9). In the figure, protein scores greater than 53 are significant (p<0.05), and * denotes peptides matching those seen in trypsin-digested menin. Endogenous interacting partners that co-purify with the tandem affinity-tagged menin are also being characterized.

Example 6

Viral Vectors Encoding Tandem Affinity-Tagged Fusions

Viral vectors facilitate efficient delivery of tandem-tagged fusion constructs to cells. In this Example, tandem affinity tagged cassettes (SBP tag and CBP tag) have been integrated in the same arrangement as found, e.g., in plasmid vectors described herein, into the AdEasy™ shuttle vector and the MMLV-based retroviral vector pFB (both Stratagene products) both for N- and C-terminal fusion to the bait protein of choice. Sequences and maps for the vectors are provided in the appendices that follow. Tandem affinity purification of the viral vector-encoded proteins demonstrates co-purification of an endogenous binding partner.

The open reading frames of cdk2, magoh and Y15 were inserted as baits into the AdEasy™ shuttle vector as well as the retroviral pFB-TAP vector, in each case N-terminally tandem affinity tagged. Adenoviral constructs were generated from the respective AdEasy™ Shuttle vectors by recombination. Adenoviral particles were generated by transfection of the AD293 packaging line and amplified through successive viral amplification cycles in AD293. Isolated adenovirus expressing the tandem affinity tagged baits were used to infect AD293, HOS and Hela cells. Affinity tagged proteins were purified from infected cells as described herein.

Figure 10:
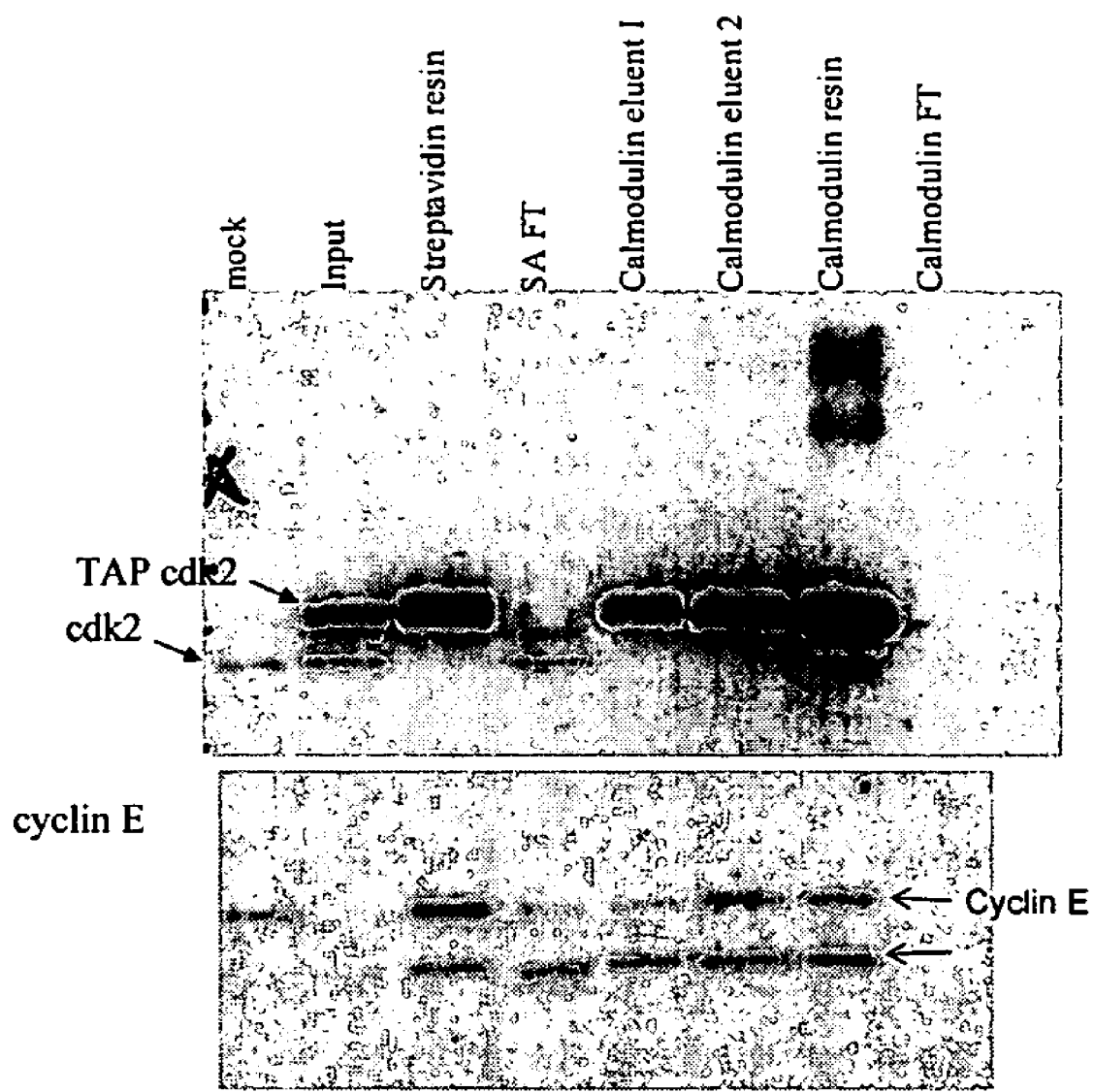
FIG. 10 shows tandem affinity purification of tandem affinity-tagged cdk2 and associated endogenous cyclin E. 293 cells were infected with an adenoviral construct expressing N-terminally tandem affinity tagged cdk2. A lysate of $10^8$ infected cells was purified first by binding and elution to a streptavidin column and then to calmodulin columns. Purification of cdk2 and cyclin E was followed by immunoblotting with the indicated antibody. Tandem affinity tagged cdk2, the endogeneous cdk2 and cyclinE (including a degradation product) are indicated by arrows. Note that the Streptavidin resin sample represents a 10 fold greater fraction of the total than the remainder samples. "Mock" refers to non-infected 293 cells; "SA FT" refers to the flow through of the streptavidin column; "Calmodulin eluent 1" was eluted in 150 mM NaCl; Calmodulin eluent 2 was eluted in 1 M NaCl. Note that the resin samples represent a 10 fold larger fraction of the total than the input or the eluates.

FIG. 10 shows the tandem affinity purification of tandem affinity-tagged cdk2 (but not endogenous cdk2) expressed from an Adenovirus detected by immunoblotting. Co-purification endogenous cyclin E, a known interaction partner of cdk2, is demonstrated by immunoblotting in the same figure.

Retroviral stocks have also been generated that comprise tandem affinity-tagged cdk2 and Y15 constructs. These retrovirus stocks have each been successfully used to infect HeLa cells (data not shown).

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

Appendix:
I. Maps of Viral Vector Examples
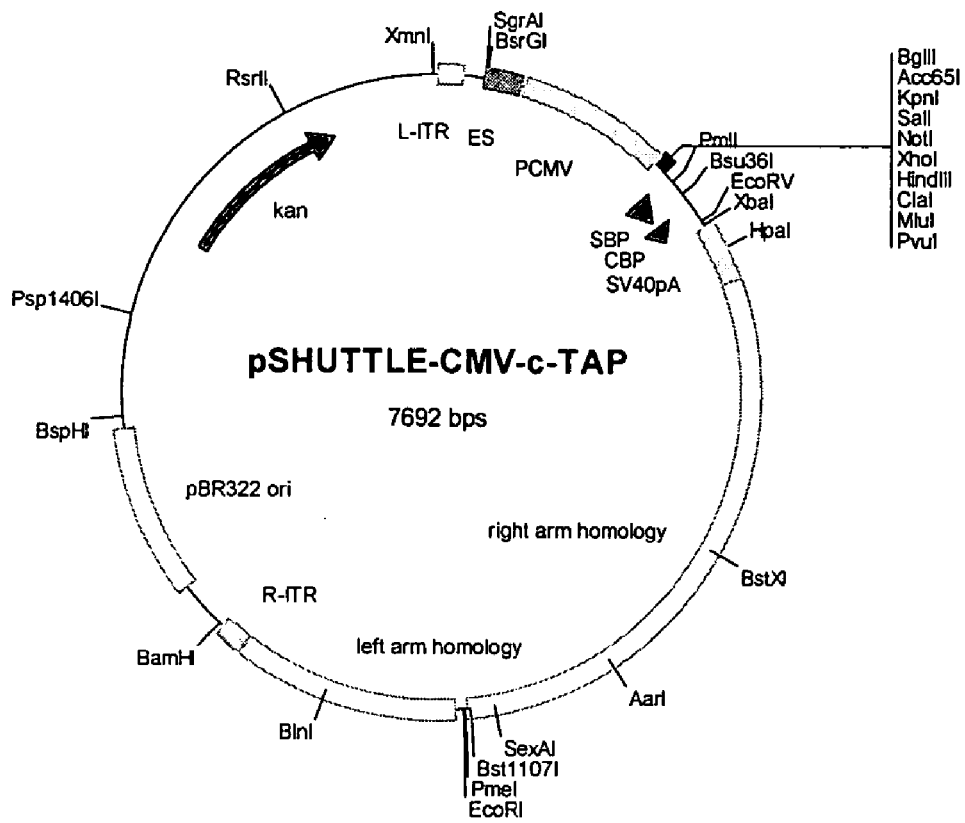

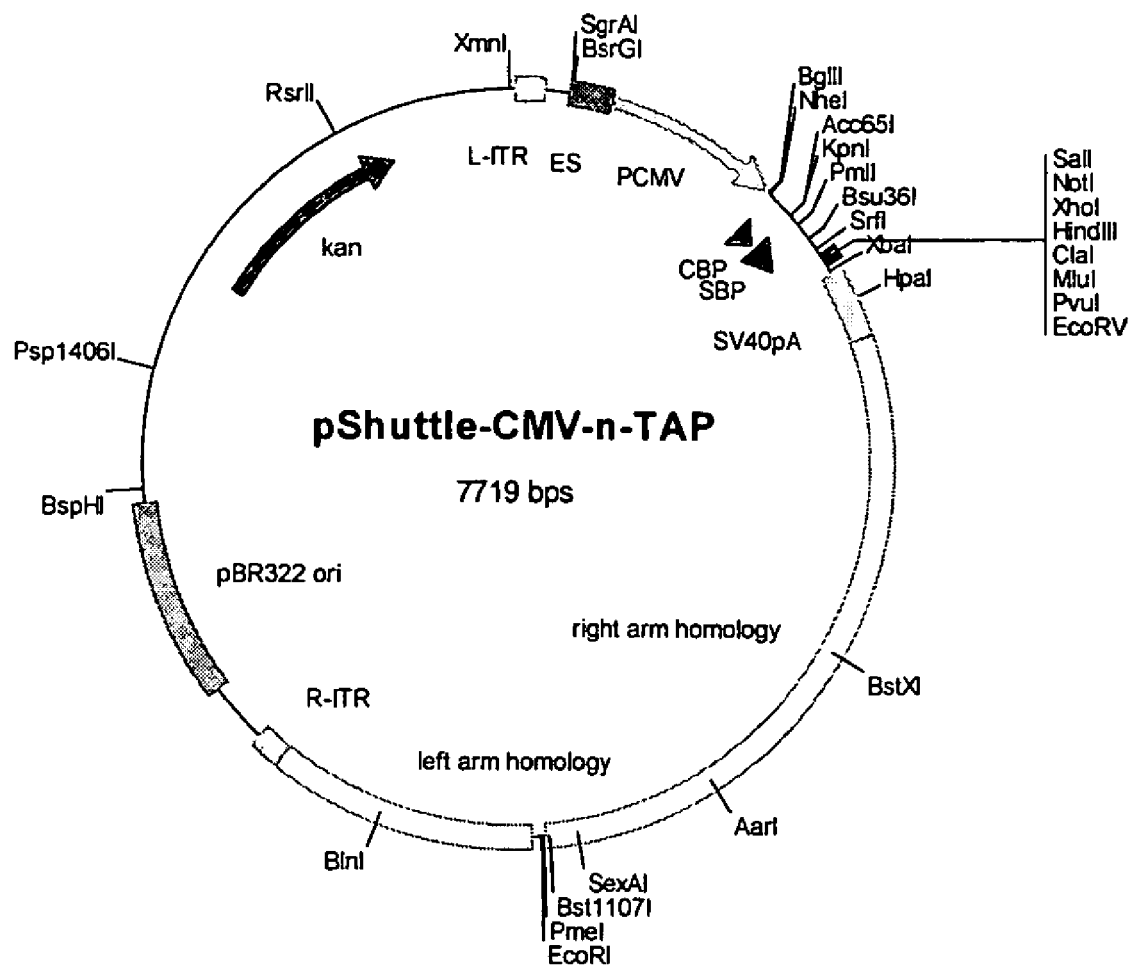

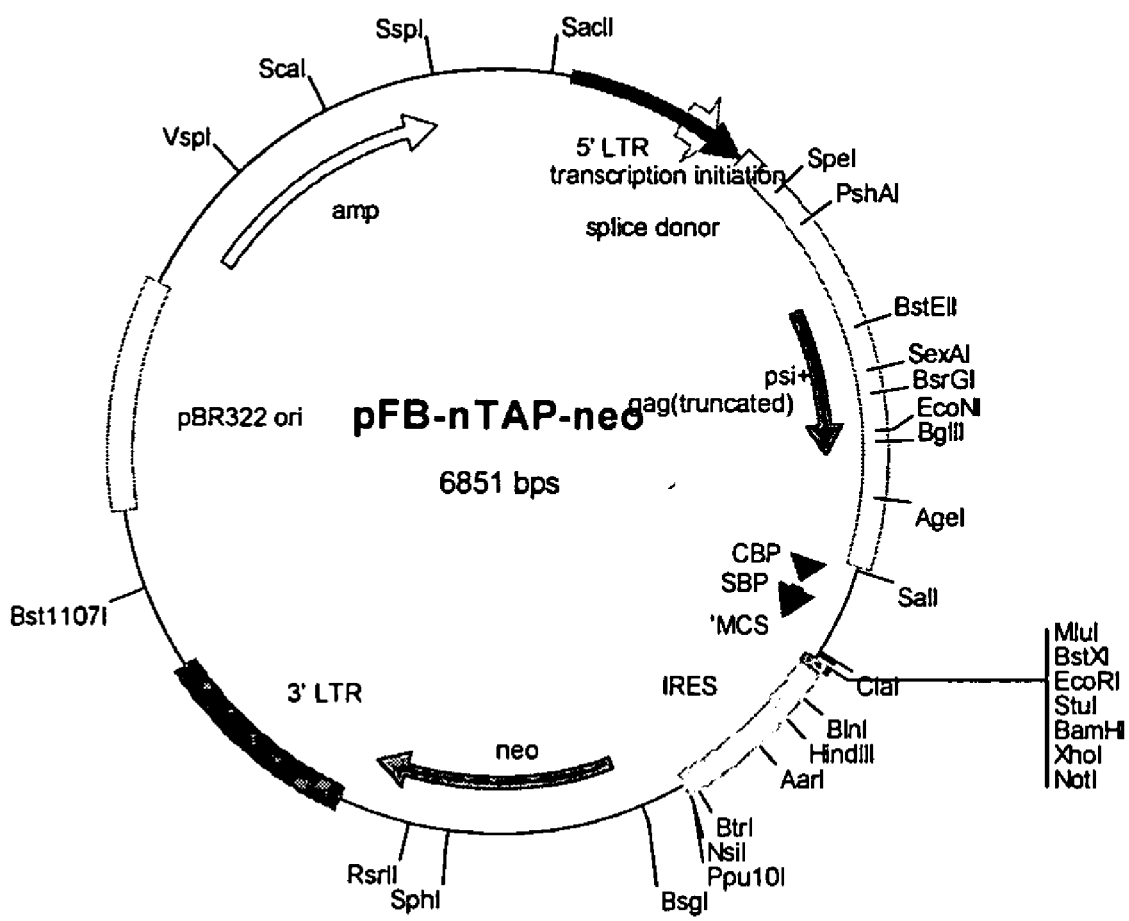

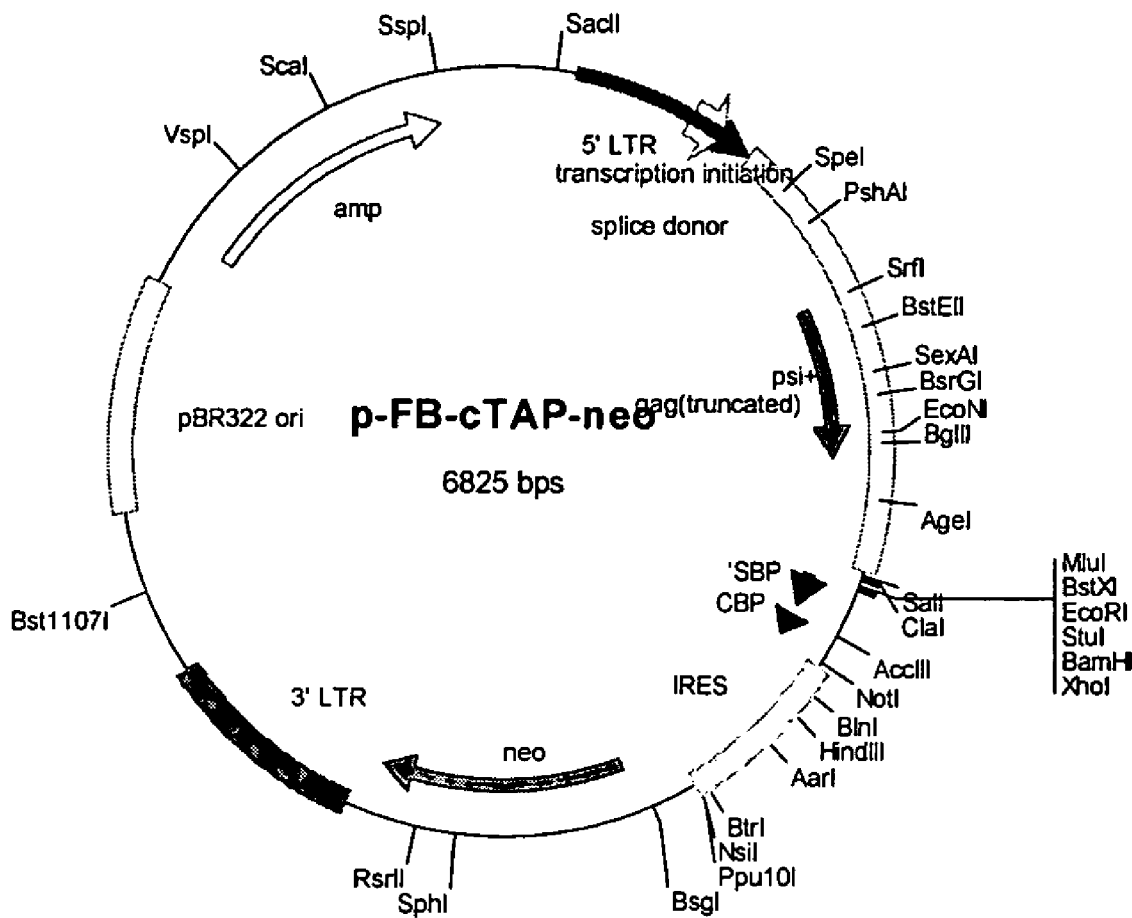

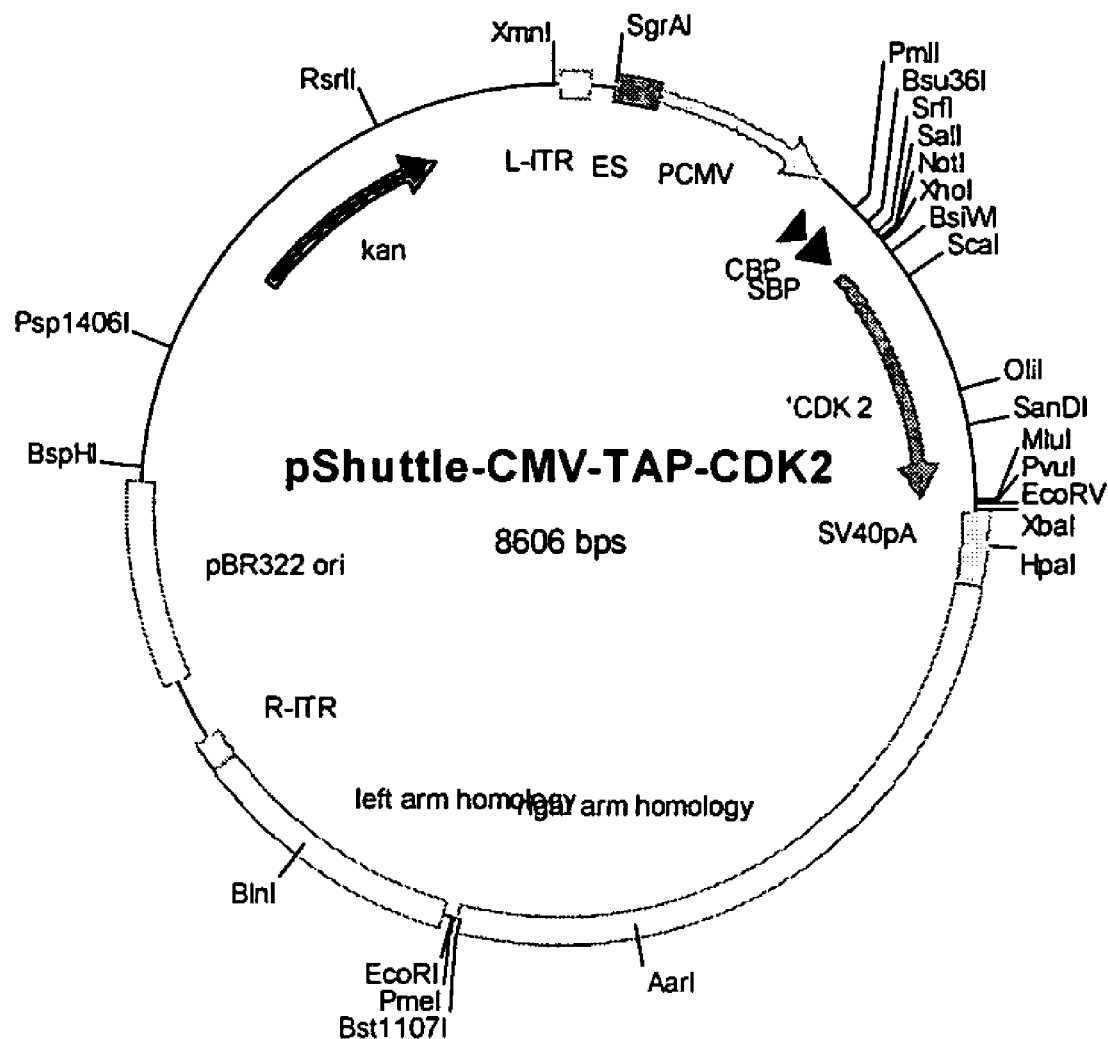

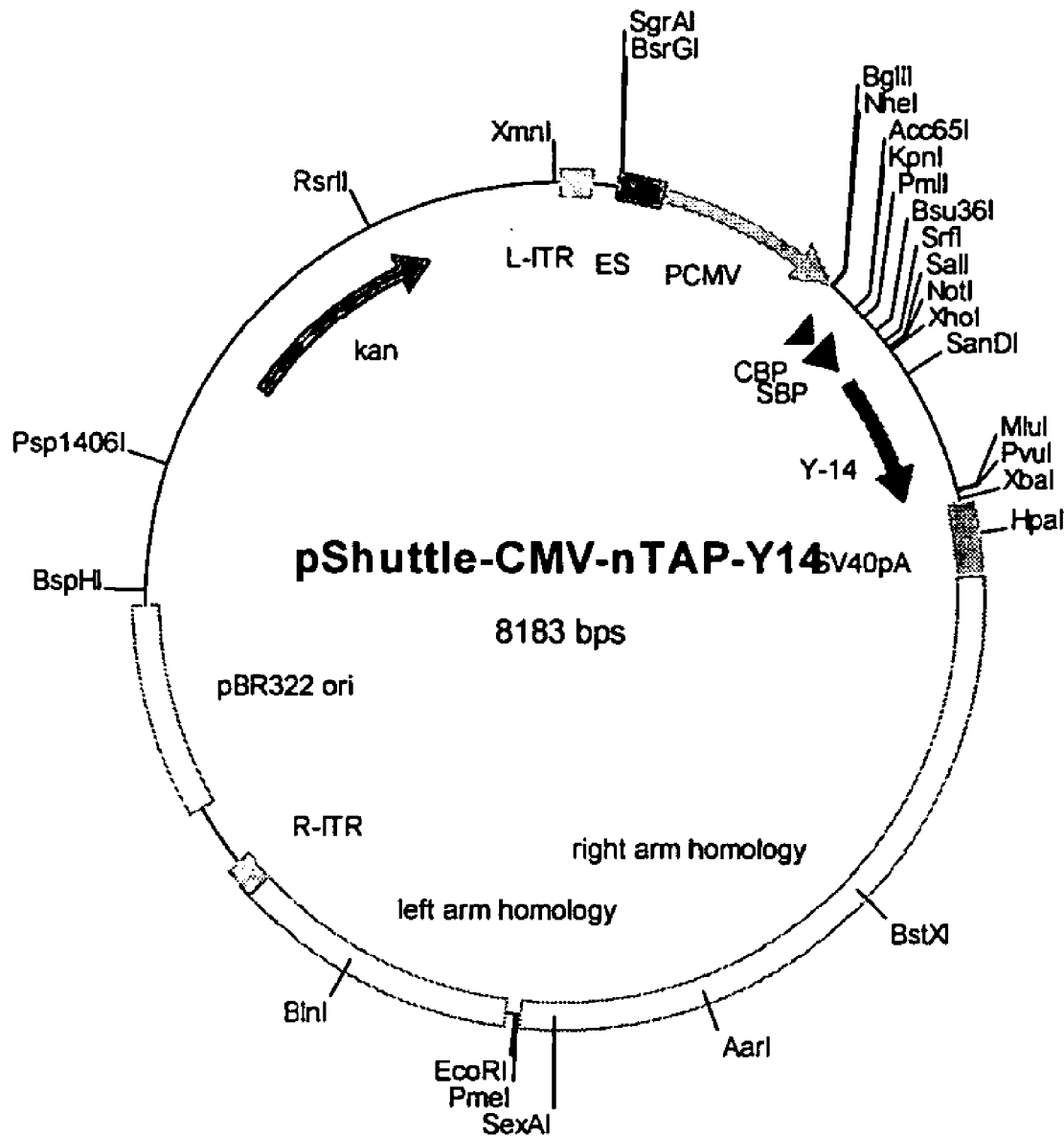

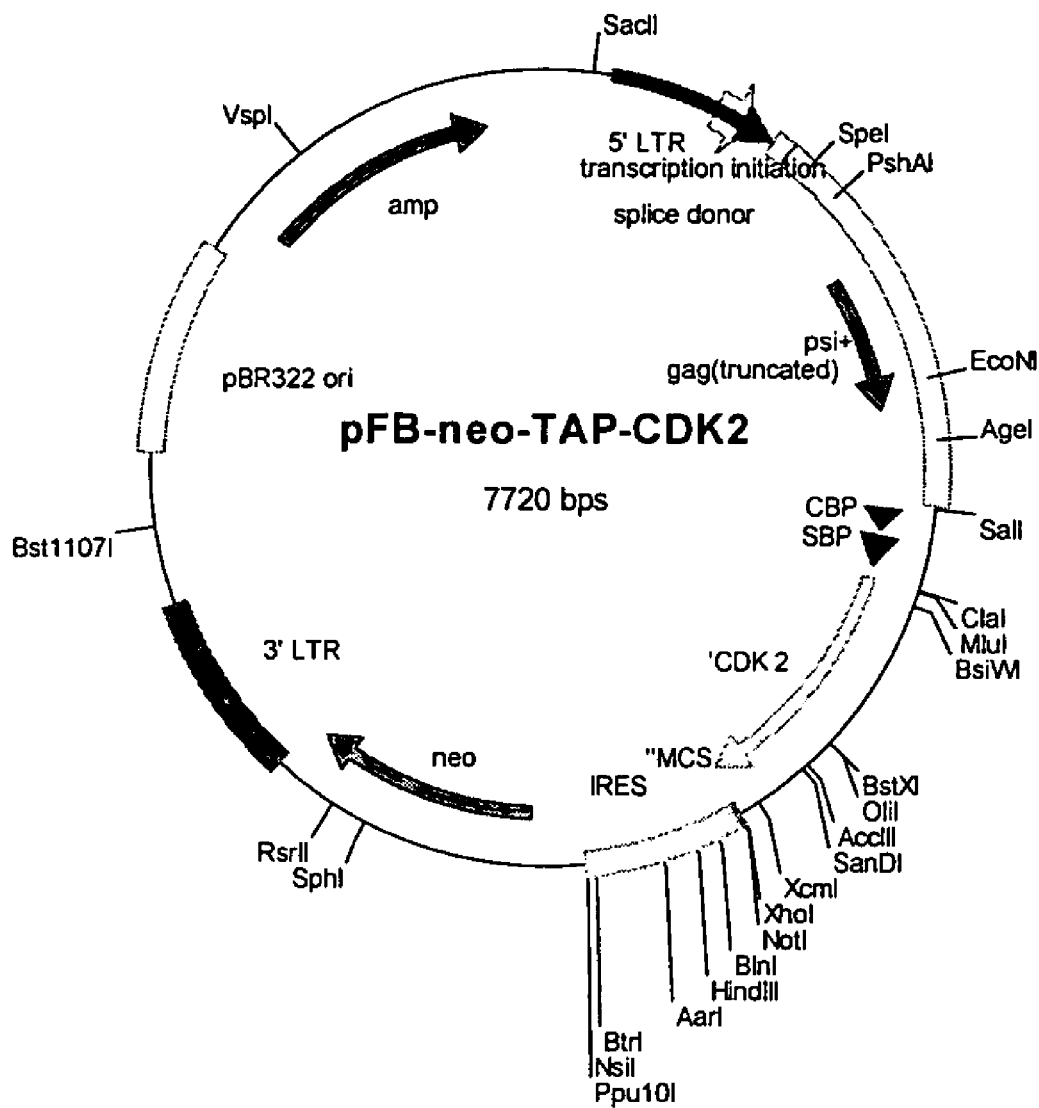

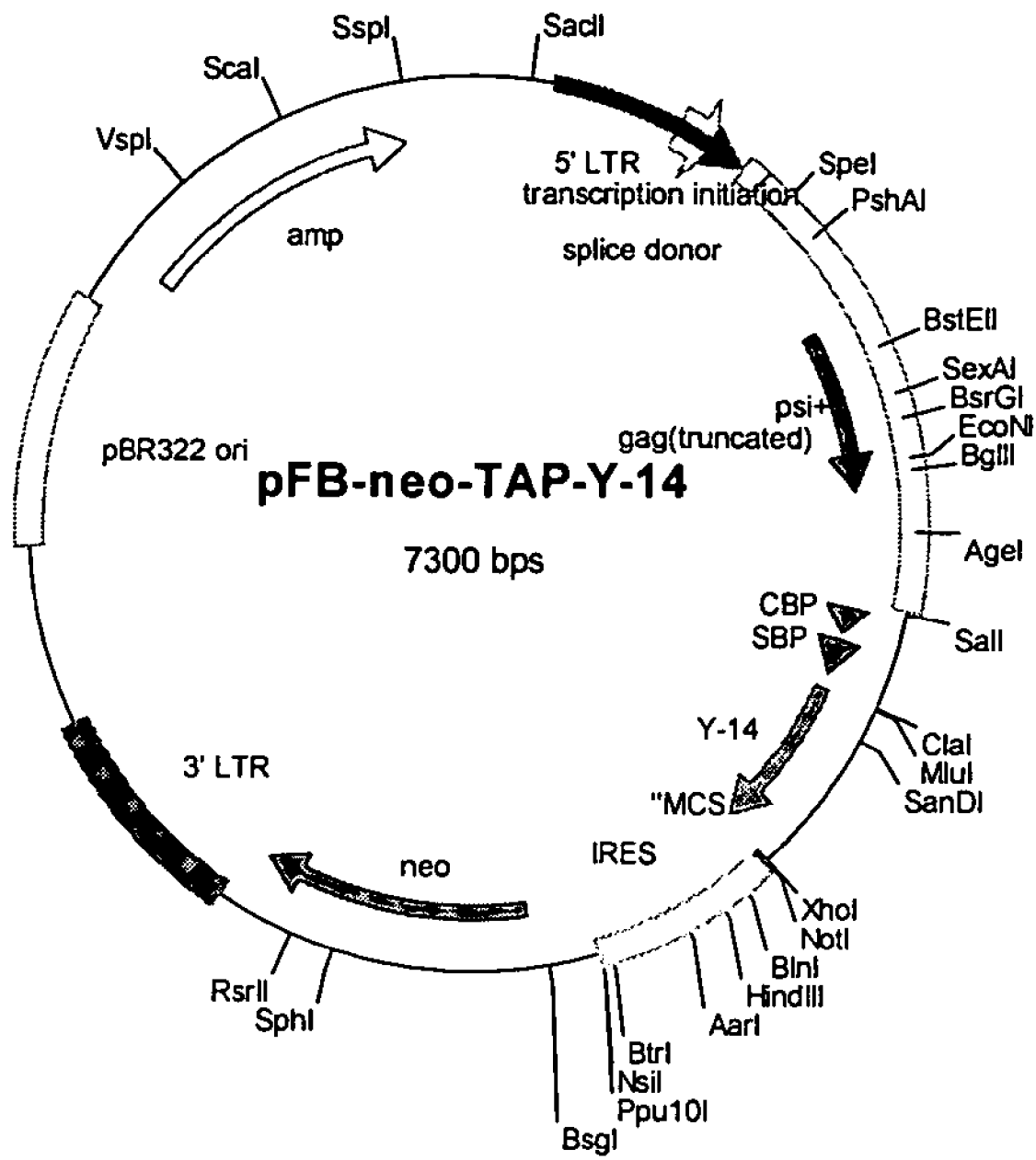

| II. Nucleotide Sequences of Viral Vector Examples |

CMV-Shuttle-cTAP

```
   1 catcatcaat aatatacctt attttggatt gaagccaata tgataatgag
  51 ggggtggagt tgtgacgtg gcgcggggcg tgggaacggg gcgggtgacg
 101 tagtagtgtg gcggaagtgt gatgttgcaa gtgtggcgga acacatgtaa
 151 gcgacggatg tggcaaaagt gacgttttg gtgtgcgccg gtgtacacag
 201 gaagtgacaa ttttcgcgcg gttttaggcg gatgttgtag taaatttggg
 251 cgtaaccgag taagatttgg ccattttcgc gggaaaactg aataagagga
 301 agtgaaatct gaataatttt gtgttactca tagcgcgtaa nnnntaatag
 351 taatcaatta cggggtcatt agttcatagc ccatatatgg agttccgcgt
 401 tacataactt acggtaaatg gcccgcctgg ctgaccgccc aacgacccc
 451 gcccattgac gtcaataatg acgtatgttc ccatagtaac gccaataggg
 501 actttccatt gacgtcaatg ggtggagtat ttacggtaaa ctgcccactt
 551 ggcagtacat caagtgtatc atatgccaag tacgccccct attgacgtca
 601 atgacggtaa atggcccgcc tggcattatg cccagtacat gaccttatgg
 651 gactttccta cttggcagta catctacgta ttagtcatcg ctattaccat
 701 ggtgatgcgg ttttggcagt acatcaatgg gcgtggatag cggtttgact
 751 cacggggatt tccaagtctc cacccccattg acgtcaatgg gagtttgttt
 801 tggcaccaaa atcaacggga ctttccaaaa tgtcgtaaca actccgcccc
 851 attgacgcaa atgggcggta ggcgtgtacg gtgggaggtc tatataagca
 901 gagctggttt agtgaaccgt cagatccgct agagatctgg taccgtcgac
 951 gcggccgctc gagcctaagc ttatcgatac gcgtccgatc ggcagcaatg
1001 gacgagaaga ccaccggctg gcggggcggc cacgtggtgg agggcctggc
1051 cggcgagctg gagcagctgc gggccaggct ggagcaccac cctcaggcc
1101 agcgggagcc ctccggcggc tgcaagctgg gctccggaaa gcgacgatgg
1151 aaaaagaatt tcatagccgt ctcagcagcc aaccgcttta agaaaatctc
1201 atcctccggg gcactttagg atatccgatc caccggatct agataactga
1251 tcataatcag ccataccaca tttgtagagg ttttacttgc tttaaaaaac
1301 ctcccacacc tccccctgaa cctgaaacat aaaatgaatg caattgttgt
1351 tgttaacttg tttattgcag cttataatgg ttacaaataa agcaatagca
1401 tcacaaattt cacaaataaa gcatttttt cactgcattc tagttgtggt
1451 ttgtccaaac tcatcaatgt atcttaacgc nnnntaaggg tgggaagaa
1501 tatataaggt gggggtctta tgtagttttg tatctgtttt gcagcagccg
1551 ccgccgccat gagcaccaac tcgtttgatg gaagcattgt gagctcatat
1601 ttgacaacgc gcatgccccc atgggccggg gtgcgtcaga atgtgatggg
1651 ctccagcatt gatggtcgcc ccgtcctgcc cgcaaactct actaccttga
1701 cctacgagac cgtgtctgga acgcgttgg agactgcagc ctccgccgcc
1751 gcttcagccg ctgcagccac cgcccgcggg attgtgactg actttgcttt
1801 cctgagcccg cttgcaagca gtgcagcttc ccgttcatcc gcccgcgatg
1851 acaagttgac ggctcttttg gcacaattgg attctttgac ccgggaactt
```

II. Nucleotide Sequences of Viral Vector Examples

-continued

```
1901 aatgtcgttt ctcagcagct gttggatctg cgccagcagg tttctgccct
1951 gaaggcttcc tcccctccca atgcggttta aaacataaat aaaaaaccag
2001 actctgtttg gatttggatc aagcaagtgt cttgctgtct ttatttaggg
2051 gttttgcgcg cgcggtaggc ccgggaccag cggtctcggt cgttgagggt
2101 cctgtgtatt ttttccagga cgtggtaaag gtgactctgg atgttcagat
2151 acatgggcat aagcccgtct ctgggtgga ggtagcacca ctgcagagct
2201 tcatgctgcg gggtggtgtt gtagatgatc cagtcgtagc aggagcgctg
2251 ggcgtggtgc ctaaaaatgt ctttcagtag caagctgatt gccagggggca
2301 ggcccttggt gtaagtgttt acaaagcggt taagctggga tgggtgcata
2351 cgtggggata tgagatgcat cttggactgt attttaggt tggctatgtt
2401 cccagccata tccctccggg gattcatgtt gtgcagaacc accagcacag
2451 tgtatccggt gcacttggga aatttgtcat gtagcttaga aggaaatgcg
2501 tggaagaact tggagacgcc cttgtgacct ccaagatttt ccatgcattc
2551 gtccataatg atggcaatgg gcccacgggc ggcggcctgg gcgaagatat
2601 ttctgggatc actaacgtca tagttgtgtt ccaggatgag atcgtcatag
2651 gccatttta caaagcgcgg gcggagggtg ccagactgcg gtataatggt
2701 tccatccggc ccaggggcgt agttaccctc acagatttgc atttcccacg
2751 ctttgagttc agatgggggg atcatgtcta cctgcggggc gatgaagaaa
2801 acggtttccg gggtagggga gatcagctgg gaagaaagca ggttcctgag
2851 cagctgcgac ttaccgcagc cggtgggccc gtaaatcaca cctattaccg
2901 ggtgcaactg gtagttaaga gagctgcagc tgccgtcatc cctgagcagg
2951 ggggccactt cgttaagcat gtccctgact cgcatgtttt ccctgaccaa
3001 atccgccaga aggcgctcgc cgcccagcga tagcagttct tgcaaggaag
3051 caaagttttt caacggtttg agaccgtccg ccgtaggcat gcttttgagc
3101 gtttgaccaa gcagttccag gcggtcccac agctcggtca cctgctctac
3151 ggcatctcga tccagcatat ctcctcgttt cgcgggttgg ggcggctttc
3201 gctgtacggc agtagtcggt gctcgtccag acgggccagg gtcatgtctt
3251 tccacgggcg cagggtcctc gtcagcgtag tctgggtcac ggtgaagggg
3301 tgcgctccgg gctgcgcgct ggccagggtg cgcttgaggc tggtcctgct
3351 ggtgctgaag cgctgccggt cttcgccctg cgcgtcggcc aggtagcatt
3401 tgaccatggt gtcatagtcc agcccctccg cggcgtggcc cttggcgcgc
3451 agcttgccct tggaggaggc gccgcacgag gggcagtgca gacttttgag
3501 ggcgtagagc ttgggcgcga gaaataccga ttccggggag taggcatccg
3551 cgccgcaggc cccgcagacg gtctcgcatt ccacgagcca ggtgagctct
3601 ggccgttcgg ggtcaaaaac caggtttccc ccatgctttt tgatgcgttt
3651 cttacctctg gtttccatga gccggtgtcc acgctcggtg acgaaaaggc
3701 tgtccgtgtc cccgtataca gacttgagag ggagtttaaa cgaattcaat
3751 agcttgttgc atgggcggcg atataaaatg caaggtgctg ctcaaaaaat
```

-continued

II. Nucleotide Sequences of Viral Vector Examples

```
3801 caggcaaagc ctcgcgcaaa aagaaagca catcgtagtc atgctcatgc
3851 agataaaggc aggtaagctc cggaaccacc acagaaaaag acaccatttt
3901 tctctcaaac atgtctgcgg gtttctgcat aaacacaaaa taaaataaca
3951 aaaaaacatt taaacattag aagcctgtct tacaacagga aaaacaaccc
4001 ttataagcat aagacggact acggccatgc cggcgtgacc gtaaaaaaac
4051 tggtcaccgt gattaaaaag caccaccgac agctcctcgg tcatgtccgg
4101 agtcataatg taagactcgg taaacacatc aggttgattc atcggtcagt
4151 gctaaaaagc gaccgaaata gcccggggga atacataccc gcaggcgtag
4201 agacaacatt acagccccca taggaggtat aacaaaatta ataggagaga
4251 aaaacacata aacacctgaa aaaccctcct gcctaggcaa aatagcaccc
4301 tcccgctcca gaacaacata cagcgcttca cagcggcagc ctaacagtca
4351 gccttaccag taaaaagaa aacctattaa aaaacacca ctcgacacgg
4401 caccagctca atcagtcaca gtgtaaaaaa gggccaagtg cagagcgagt
4451 atatatagga ctaaaaatg acgtaacggt taaagtccac aaaaaacacc
4501 cagaaaaccg cacgcgaacc tacgcccaga aacgaaagcc aaaaaaccca
4551 caacttcctc aaatcgtcac ttccgttttc ccacgttacg taacttccca
4601 ttttaagaaa actacaattc ccaacacata caagttactc cgccctaaaa
4651 cctacgtcac ccgccccgtt cccacgcccc gcgccacgtc acaaactcca
4701 cccctcatt atcatattgg cttcaatcca aaataaggta tattattgat
4751 gatgttaatt aacatgcatg gatccatatg cggtgtgaaa taccgcacag
4801 atgcgtaagg agaaaatacc gcatcaggcg ctcttccgct tcctcgctca
4851 ctgactcgct gcgctcggtc gttcggctgc ggcgagcggt atcagctcac
4901 tcaaaggcgg taatacggtt atccacagaa tcaggggata acgcaggaaa
4951 gaacatgtga gcaaaaggcc agcaaaaggc caggaaccgt aaaaaggccg
5001 cgttgctggc gtttttccat aggctccgcc ccctgacga gcatcacaaa
5051 aatcgacgct caagtcagag gtggcgaaac ccgacaggac tataaagata
5101 ccaggcgttt ccccctggaa gctccctcgt gcgctctcct gttccgaccc
5151 tgccgcttac cggatacctg tccgcctttc tcccttcggg aagcgtggcg
5201 ctttctcata gctcacgctg taggtatctc agttcggtgt aggtcgttcg
5251 ctccaagctg ggctgtgtgc acgaacccc cgttcagccc gaccgctgcg
5301 ccttatccgg taactatcgt cttgagtcca acccggtaag acacgactta
5351 tcgccactgg cagcagccac tggtaacagg attagcagag cgaggtatgt
5401 aggcggtgct acagagttct tgaagtggtg gcctaactac ggctacacta
5451 gaaggacagt atttggtatc tgcgctctgc tgaagccagt taccttcgga
5501 aaaagagttg gtagctcttg atccggcaaa caaaccaccg ctggtagcgg
5551 tggtttttt gtttgcaagc agcagattac gcgcagaaaa aaaggatctc
5601 aagaagatcc tttgatcttt tctacggggt ctgacgctca gtggaacgaa
5651 aactcacgtt aagggatttt ggtcatgaga ttatcaaaaa ggatcttcac
5701 ctagatcctt ttaaattaaa aatgaagttt taaatcaatc taaagtatat
```

-continued

II. Nucleotide Sequences of Viral Vector Examples

```
5751 atgagtaaac ttggtctgac agttaccaat gcttaatcag tgaggcacct
5801 atctcagcga tctgtctatt tcgttcatcc atagttgcct gactccccgt
5851 cgtgtagata actacgatac gggagggctt accatctggc cccagtgctg
5901 caatgatacc gcgagaccca cgctcaccgg ctccagattt atcagcaata
5951 aaccagccag ccggaagggc cgagcgcaga agtggtcctg caactttatc
6001 cgcctccatc cagtctatta attgttgccg ggaagctaga gtaagtagtt
6051 cgccagttaa tagtttgcgc aacgttgttg ccattgctgc agccatgaga
6101 ttatcaaaaa ggatcttcac ctagatcctt ttcacgtaga aagccagtcc
6151 gcagaaacgg tgctgacccc ggatgaatgt cagctactgg gctatctgga
6201 caagggaaaa cgcaagcgca aagagaaagc aggtagcttg cagtgggctt
6251 acatggcgat agctagactg ggcggtttta tggacagcaa gcgaaccgga
6301 attgccagct ggggcgccct ctggtaaggt tgggaagccc tgcaaagtaa
6351 actggatggc tttcttgccg ccaaggatct gatggcgcag gggatcaagc
6401 tctgatcaag agacaggatg aggatcgttt cgcatgattg aacaagatgg
6451 attgcacgca ggttctccgg ccgcttgggt ggagaggcta ttcggctatg
6501 actgggcaca acagacaatc ggctgctctg atgccgccgt gttccggctg
6551 tcagcgcagg ggcgcccggt tctttttgtc aagaccgacc tgtccggtgc
6601 cctgaatgaa ctgcaagacg aggcagcgcg gctatcgtgg ctggccacga
6651 cgggcgttcc ttgcgcagct gtgctcgacg ttgtcactga agcgggaagg
6701 gactggctgc tattgggcga agtgccgggg caggatctcc tgtcatctca
6751 ccttgctcct gccgagaaag tatccatcat ggctgatgca atgcggcggc
6801 tgcatacgct tgatccggct acctgcccat tcgaccacca agcgaaacat
6851 cgcatcgagc gagcacgtac tcggatggaa gccggtcttg tcgatcagga
6901 tgatctggac gaagagcatc agggctcgc gccagccgaa ctgttcgcca
6951 ggctcaaggc gagcatgccc gacggcgagg atctcgtcgt gacccatggc
7001 gatgcctgct tgccgaatat catggtggaa aatggccgct tttctggatt
7051 catcgactgt ggccggctgg gtgtggcgga ccgctatcag gacatagcgt
7101 tggctacccg tgatattgct gaagagcttg gcggcgaatg ggctgaccgc
7151 ttcctcgtgc tttacggtat cgccgctccc gattcgcagc gcatcgcctt
7201 ctatcgcctt cttgacgagt tcttctgaat tttgttaaaa ttttttgttaa
7251 atcagctcat tttttaacca ataggccgaa atcggcaaca tcccttataa
7301 atcaaaagaa tagaccgcga tagggttgag tgttgttcca gtttggaaca
7351 agagtccact attaaagaac gtggactcca acgtcaaagg gcgaaaaacc
7401 gtctatcagg gcgatggccc actacgtgaa ccatcaccca aatcaagttt
7451 tttgcggtcg aggtgccgta aagctctaaa tcggaaccct aaaggagcc
7501 cccgatttag agcttgacgg ggaaagccgg cgaacgtggc gagaaaggaa
7551 gggaagaaag cgaaaggagc gggcgctagg gcgctggcaa gtgtagcggt
7601 cacgctgcgc gtaaccacca cacccgcgcg cttaatgcgc cgctacaggg
```

II. Nucleotide Sequences of Viral Vector Examples 7651 cgcgtccatt cgccattcag gatcgaatta attcttaatt aa CMV-Shuttle-nTAP

```
   1 catcatcaat aatataccttt attttggatt gaagccaata tgataatgag
  51 ggggtggagt ttgtgacgtg gcgcggggcg tgggaacggg gcgggtgacg
 101 tagtagtgtg gcggaagtgt gatgttgcaa gtgtggcgga acacatgtaa
 151 gcgacggatg tggcaaaagt gacgttttg tgtgcgccg gtgtacacag
 201 gaagtgacaa ttttcgcgcg gttttaggcg gatgttgtag taaatttggg
 251 cgtaaccgag taagatttgg ccattttcgc gggaaaactg aataagagga
 301 agtgaaatct gaataatttt gtgttactca tagcgcgtaa nnnntaatag
 351 taatcaatta cggggtcatt agttcatagc ccatatatgg agttccgcgt
 401 tacataactt acggtaaatg gcccgcctgg ctgaccgccc aacgacccc
 451 gcccattgac gtcaataatg acgtatgttc ccatagtaac gccaataggg
 501 actttccatt gacgtcaatg ggtggagtat ttacggtaaa ctgcccactt
 551 ggcagtacat caagtgtatc atatgccaag tacgccccct attgacgtca
 601 atgacggtaa atggcccgcc tggcattatg cccagtacat gaccttatgg
 651 gactttccta cttggcagta catctacgta ttagtcatcg ctattaccat
 701 ggtgatgcgg ttttggcagt acatcaatgg gcgtggatag cggtttgact
 751 cacggggatt tccaagtctc cacccattg acgtcaatgg gagtttgttt
 801 tggcaccaaa atcaacggga ctttccaaaa tgtcgtaaca actccgcccc
 851 attgacgcaa atgggcggta ggcgtgtacg gtgggaggtc tatataagca
 901 gagctggttt agtgaaccgt cagatccgct agagatctgc tagcatgaag
 951 cgacgatgga aaagaatttt catagccgtc tcagcagcca accgctttaa
1001 gaaaatctca tcctccgggg cacttggaag cggtagcggt accatggacg
1051 agaagaccac cggctggcgg ggcggccacg tggtggaggg cctggccggc
1101 gagctggagc agctgcgggc caggctggag caccaccctc agggccagcg
1151 ggagccctcc ggcggctgca agctgggcgc ccgggcggat ccccgggcg
1201 tcgacgcggc cgctcgagcc gaagcttatc gatacgcgtc cgatcggata
1251 tccgatccac cggatctaga taactgatca taatcagcca taccacattt
1301 gtagaggttt tacttgcttt aaaaaacctc ccacacctcc ccctgaacct
1351 gaaacataaa atgaatgcaa ttgttgttgt taacttgttt attgcagctt
1401 ataatggtta caaataaagc aatagcatca caaatttcac aaataaagca
1451 ttttttcac tgcattctag ttgtggtttg tccaaactca tcaatgtatc
1501 ttaacgcnnn ntaagggtgg gaaagaatat ataaggtggg ggtcttatgt
1551 agttttgtat ctgttttgca gcagccgccg ccgccatgag caccaactcg
1601 tttgatggaa gcattgtgag ctcatatttg acaacgcgca tgcccccatg
1651 ggccggggtg cgtcagaatg tgatgggctc cagcattgat ggtcgccccg
1701 tcctgcccgc aaactctact accttgacct acgagaccgt gtctggaacg
1751 ccgttggaga ctgcagcctc cgccgccgct tcagccgctg cagccaccgc
1801 ccgcgggatt gtgactgact ttgcttttcct gagcccgctt gcaagcagtg
```

-continued

II. Nucleotide Sequences of Viral Vector Examples

```
1851 cagcttcccg ttcatccgcc cgcgatgaca agttgacggc tcttttggca
1901 caattggatt ctttgacccg ggaacttaat gtcgtttctc agcagctgtt
1951 ggatctgcgc cagcaggttt ctgccctgaa ggcttcctcc cctcccaatg
2001 cggtttaaaa cataaataaa aaaccagact ctgtttggat ttggatcaag
2051 caagtgtctt gctgtcttta tttaggggtt ttgcgcgcgc ggtaggcccg
2101 ggaccagcgg tctcggtcgt tgagggtcct gtgtatttt tccaggacgt
2151 ggtaaaggtg actctggatg ttcagataca tgggcataag cccgtctctg
2201 gggtggaggt agcaccactg cagagcttca tgctgcgggg tggtgttgta
2251 gatgatccag tcgtagcagg agcgctgggc gtggtgccta aaaatgtctt
2301 tcagtagcaa gctgattgcc aggggcaggc ccttggtgta agtgtttaca
2351 aagcggttaa gctgggatgg gtgcatacgt ggggatatga gatgcatctt
2401 ggactgtatt tttaggttgg ctatgttccc agccatatcc ctccggggat
2451 tcatgttgtg cagaaccacc agcacagtgt atccggtgca cttgggaaat
2501 ttgtcatgta gcttagaagg aaatgcgtgg aagaacttgg agacgccctt
2551 gtgacctcca agattttcca tgcattcgtc cataatgatg gcaatgggcc
2601 cacgggcggc ggcctgggcg aagatatttc tgggatcact aacgtcatag
2651 ttgtgttcca ggatgagatc gtcataggcc attttacaa agcgcgggcg
2701 gagggtgcca gactgcggta taatggttcc atccggccca ggggcgtagt
2751 taccctcaca gatttgcatt tcccacgctt tgagttcaga tgggggatc
2801 atgtctacct gcgggcgat gaagaaaacg gtttccgggg taggggagat
2851 cagctgggaa gaaagcaggt tcctgagcag ctgcgactta ccgcagccgg
2901 tgggcccgta aatcacacct attaccgggt gcaactggta gttaagagag
2951 ctgcagctgc cgtcatccct gagcagggg gccacttcgt taagcatgtc
3001 cctgactcgc atgttttccc tgaccaaatc cgccagaagg cgctcgccgc
3051 ccagcgatag cagttcttgc aaggaagcaa agtttttcaa cggtttgaga
3101 ccgtccgccg taggcatgct tttgagcgtt tgaccaagca gttccaggcg
3151 gtcccacagc tcggtcacct gctctacggc atctcgatcc agcatatctc
3201 ctcgtttcgc gggttggggc ggctttcgct gtacggcagt agtcggtgct
3251 cgtccagacg ggccagggtc atgtctttcc acgggcgcag ggtcctcgtc
3301 agcgtagtct gggtcacggt gaagggtgc gctccgggct gcgcgctggc
3351 cagggtgcgc ttgaggctgg tcctgctggt gctgaagcgc tgccggtctt
3401 cgccctgcgc gtcggccagg tagcatttga ccatggtgtc atagtccagc
3451 ccctccgcgg cgtggccctt ggcgcgcagc ttgcccttgg aggaggcgcc
3501 gcacgagggg cagtgcagac ttttgagggc gtagagcttg ggcgcgagaa
3551 ataccgattc cggggagtag catccgcgc cgcaggcccc gcagacggtc
3601 tcgcattcca cgagccaggt gagctctggc cgttcggggt caaaaaccag
3651 gtttccccca tgcttttttga tgcgtttctt acctctggtt tccatgagcc
3701 ggtgtccacg ctcggtgacg aaaaggctgt ccgtgtcccc gtatacagac
```

II. Nucleotide Sequences of Viral Vector Examples

```
3751 ttgagaggga gtttaaacga attcaatagc ttgttgcatg ggcggcgata
3801 taaaatgcaa ggtgctgctc aaaaaatcag gcaaagcctc gcgcaaaaaa
3851 gaaagcacat cgtagtcatg ctcatgcaga taaaggcagg taagctccgg
3901 aaccaccaca gaaaaagaca ccattttct ctcaaacatg tctgcgggtt
3951 tctgcataaa cacaaaataa aataacaaaa aaacatttaa acattagaag
4001 cctgtcttac aacaggaaaa acaaccctta taagcataag acggactacg
4051 gccatgccgg cgtgaccgta aaaaaactgg tcaccgtgat taaaaagcac
4101 caccgacagc tcctcggtca tgtccggagt cataatgtaa gactcggtaa
4151 acacatcagg ttgattcatc ggtcagtgct aaaaagcgac cgaaatagcc
4201 cgggggaata catacccgca ggcgtagaga caacattaca gccccccatag
4251 gaggtataac aaaattaata ggagagaaaa acacataaac acctgaaaaa
4301 ccctcctgcc taggcaaaat agcaccctcc cgctccagaa caacatacag
4351 cgcttcacag cggcagccta acagtcagcc ttaccagtaa aaaagaaaac
4401 ctattaaaaa aacaccactc gacacggcac cagctcaatc agtcacagtg
4451 taaaaaaggg ccaagtgcag agcgagtata tataggacta aaaaatgacg
4501 taacggttaa agtccacaaa aaacacccag aaaaccgcac gcgaacctac
4551 gcccagaaac gaaagccaaa aaacccacaa cttcctcaaa tcgtcacttc
4601 cgttttccca cgttacgtaa cttcccattt taagaaaact acaattccca
4651 acacatacaa gttactccgc cctaaaacct acgtcacccg ccccgttccc
4701 acgccccgcg ccacgtcaca aactccaccc cctcattatc atattggctt
4751 caatccaaaa taaggtatat tattgatgat gttaattaac atgcatggat
4801 ccatatgcgg tgtgaaatac cgcacagatg cgtaaggaga aaataccgca
4851 tcaggcgctc ttccgcttcc tcgctcactg actcgctgcg ctcggtcgtt
4901 cggctgcggc gagcggtatc agctcactca aaggcggtaa tacggttatc
4951 cacagaatca ggggataacg caggaaagaa catgtgagca aaaggccagc
5001 aaaaggccag gaaccgtaaa aaggccgcgt tgctggcgtt tttccatagg
5051 ctccgccccc ctgacgagca tcacaaaaat cgacgctcaa gtcagaggtg
5101 gcgaaacccg acaggactat aaagatacca ggcgtttccc cctggaagct
5151 ccctcgtgcg ctctcctgtt ccgaccctgc cgcttaccgg atacctgtcc
5201 gcctttctcc cttcgggaag cgtggcgctt tctcatagct cacgctgtag
5251 gtatctcagt tcggtgtagg tcgttcgctc caagctgggc tgtgtgcacg
5301 aaccccccgt tcagcccgac cgctgcgcct tatccggtaa ctatcgtctt
5351 gagtccaacc cggtaagaca cgacttatcg ccactggcag cagccactgg
5401 taacaggatt agcagagcga ggtatgtagg cggtgctaca gagttcttga
5451 agtggtggcc taactacggc tacactagaa ggacagtatt tggtatctgc
5501 gctctgctga agccagttac cttcggaaaa agagttggta gctcttgatc
5551 cggcaaacaa accaccgctg gtagcggtgg ttttttgtt tgcaagcagc
5601 agattacgcg cagaaaaaaa ggatctcaag aagatccttt gatcttttct
5651 acgggtctg acgctcagtg gaacgaaaac tcacgttaag gattttggt
```

-continued

| II. Nucleotide Sequences of Viral Vector Examples |
| --- |

```
5701 catgagatta tcaaaaagga tcttcaccta gatcctttta aattaaaaat
5751 gaagttttaa atcaatctaa agtatatatg agtaaacttg gtctgacagt
5801 taccaatgct taatcagtga ggcacctatc tcagcgatct gtctatttcg
5851 ttcatccata gttgcctgac tccccgtcgt gtagataact acgatacggg
5901 agggcttacc atctggcccc agtgctgcaa tgataccgcg agacccacgc
5951 tcaccggctc cagatttatc agcaataaac cagccagccg gaagggccga
6001 gcgcagaagt ggtcctgcaa ctttatccgc ctccatccag tctattaatt
6051 gttgccggga agctagagta agtagttcgc cagttaatag tttgcgcaac
6101 gttgttgcca ttgctgcagc catgagatta tcaaaaagga tcttcaccta
6151 gatccttttc acgtagaaag ccagtccgca gaaacggtgc tgaccccgga
6201 tgaatgtcag ctactgggct atctggacaa gggaaaacgc aagcgcaaag
6251 agaaagcagg tagcttgcag tgggcttaca tggcgatagc tagactgggc
6301 ggttttatgg acagcaagcg aaccggaatt gccagctggg gcgccctctg
6351 gtaaggttgg gaagccctgc aaagtaaact ggatggcttt cttgccgcca
6401 aggatctgat ggcgcagggg atcaagctct gatcaagaga caggatgagg
6451 atcgtttcgc atgattgaac aagatggatt gcacgcaggt tctccggccg
6501 cttgggtgga gaggctattc ggctatgact gggcacaaca gacaatcggc
6551 tgctctgatg ccgccgtgtt ccggctgtca gcgcaggggc gcccggttct
6601 ttttgtcaag accgacctgt ccggtgccct gaatgaactg caagacgagg
6651 cagcgcggct atcgtggctg gccacgacgg gcgttccttg cgcagctgtg
6701 ctcgacgttg tcactgaagc gggaagggac tggctgctat tgggcgaagt
6751 gccggggcag gatctcctgt catctcacct tgctcctgcc gagaaagtat
6801 ccatcatggc tgatgcaatg cggcggctgc atacgcttga tccggctacc
6851 tgcccattcg accaccaagc gaaacatcgc atcgagcgag cacgtactcg
6901 gatggaagcc ggtcttgtcg atcaggatga tctggacgaa gagcatcagg
6951 ggctcgcgcc agccgaactg ttcgccaggc tcaaggcgag catgcccgac
7001 ggcgaggatc tcgtcgtgac ccatggcgat gcctgcttgc cgaatatcat
7051 ggtggaaaat ggccgctttt ctggattcat cgactgtggc cggctgggtg
7101 tggcggaccg ctatcaggac atagcgttgg ctacccgtga tattgctgaa
7151 gagcttggcg gcgaatgggc tgaccgcttc ctcgtgcttt acggtatcgc
7201 cgctcccgat tcgcagcgca tcgccttcta tcgccttctt gacgagttct
7251 tctgaatttt gttaaaattt ttgttaaatc agctcatttt ttaaccaata
7301 ggccgaaatc ggcaacatcc cttataaatc aaaagaatag accgcgatag
7351 ggttgagtgt tgttccagtt tggaacaaga gtccactatt aaagaacgtg
7401 gactccaacg tcaaagggcg aaaaaccgtc tatcagggcg atggcccact
7451 acgtgaacca tcacccaaat caagttttt gcggtcgagg tgccgtaaag
7501 ctctaaatcg gaaccctaaa gggagccccc gatttagagc ttgacgggga
7551 aagccggcga acgtggcgag aaaggaaggg aagaaagcga aaggagcggg
```

-continued

| II. Nucleotide Sequences of Viral Vector Examples |
| --- |

```
7601 cgctagggcg ctggcaagtg tagcggtcac gctgcgcgta accaccacac
7651 ccgcgcgctt aatgcgccgc tacagggcgc gtccattcgc cattcaggat
7701 cgaattaatt cttaattaa
``` pFB-nTAP-neo

```
   1 gaattgctag caattgctag caattgctag caattcatac cagatcaccg
  51 aaaactgtcc tccaaatgtg tccccctcac actcccaaat tcgcgggctt
 101 ctgcctctta gaccactcta ccctattccc cacactcacc ggagccaaag
 151 ccgcgggaca tatacatgtg aaagacccca cctgtaggtt tggcaagcta
 201 gcttaagtaa cgccattttg caaggcatgg aaaaatacat aactgagaat
 251 agaaaagttc agatcaaggt caggaacaga tggaacagct gaatatgggc
 301 caaagcggat atctgtggta agcagttcct gccccggctc agggccaaga
 351 acagatggaa cagctgaata tgggccaaac aggatatctg tggtaagcag
 401 ttcctgcccc ggctcagggc caagaacaga tggtccccag atgcggtcca
 451 gccctcagca gtttctagag aaccatcaga tgtttccagg gtgccccaag
 501 gacctgaaat gaccctgtgc cttatttgaa ctaaccaatc agttcgcttc
 551 tcgcttctgt tcgcgcgctt ctgctccccg agctcaataa aagagcccac
 601 aaccccctcac tcggggcgcc agtcctccga ttgactgagt cgcccgggta
 651 cccgtgtatc caataaaccc tcttgcagtt gcatccgact tgtggtctcg
 701 ctgttccttg ggagggtctc ctctgagtga ttgactaccc gtcagcgggg
 751 gtctttcatt tgggggctcg tccgggatcg ggagacccct gcccagggac
 801 caccgaccca ccaccgggag gtaagctggc cagcaactta tctgtgtctg
 851 tccgattgtc tagtgtctat gactgatttt atgcgcctgc gtcggtacta
 901 gttagctaac tagctctgta tctggcggac ccgtggtgga actgacgagt
 951 tcggaacacc cggccgcaac cctgggagac gtcccaggga cttcggggc
1001 cgttttttgtg gcccgacctg agtccaaaaa tcccgatcgt tttggactct
1051 ttggtgcacc cccttagag gagggatatg tggttctggt aggagacgag
1101 aacctaaaac agttcccgcc tccgtctgaa ttttttgcttt cggtttggga
1151 ccgaagccgc gccgcgcgtc ttgtctgctg cagcatcgtt ctgtgttgtc
1201 tctgtctgac tgtgtttctg tatttgtctg aaaatatggg cccgggccag
1251 actgttacca ctcccttaag tttgaccttag ggtcactgga aagatgtcga
1301 gcggatcgct cacaaccagt cggtagatgt caagaagaga cgttgggtta
1351 ccttctgctc tgcagaatgg ccaaccttta acgtcggatg gccgcgagac
1401 ggcacctttta accgagacct catcacccag gttaagatca aggtcttttc
1451 acctggcccg catggacacc cagaccaggt cccctacatc gtgacctggg
1501 aagccttggc ttttgacccc cctccctggg tcaagccctt tgtacaccct
1551 aagcctccgc ctcctcttcc tccatccgcc ccgtctctcc cccttgaacc
1601 tcctcgttcg accccgcctc gatcctccct ttatccagcc ctcactcctt
1651 ctctaggcgc cccatatgg ccatatgaga tcttatatgg ggcacccccg
1701 ccccttgtaa acttccctga ccctgacatg acaagagtta ctaacagccc
```

-continued

| II. Nucleotide Sequences of Viral Vector Examples |

```
1751 ctctctccaa gctcacttac aggctctcta cttagtccag cacgaagtct
1801 ggagacctct ggcggcacgt accaagaaca actggaccga ccggtggtac
1851 ctcaccctta ccgagtcggc gacacagtgt gggtccgccg acaccagact
1901 aagaacctag aacctcgctg gaaaggacct tacacagtcc tgctgaccac
1951 ccccaccgcc ctcaaagtag acggcatcgc agcttggata cacgccgccc
2001 acgtgaaggc tgccgacccc ggggtggac catcctctag actgccggat
2051 cgaattgtcg actgctagca tgaagcgacg atggaaaaag aatttcatag
2101 ccgtctcagc agccaaccgc tttaagaaaa tctcatcctc cggggcactt
2151 ggaagcggta gcggtaccat ggacgagaag accaccggct ggcggggcgg
2201 ccacgtggtg gagggcctgg ccggcgagct ggagcagctg cgggccaggc
2251 tggagcacca ccctcagggc cagcgggagc cctccggcgg ctgcaagctg
2301 ggcgcccggg catcgatacg cgtccagcac agtgggaatt caggcctgga
2351 tcctcgagcg gccgcgatcc ggttattttc caccatattg ccgtcttttg
2401 gcaatgtgag ggcccggaaa cctggccctg tcttcttgac gagcattcct
2451 aggggtcttt cccctctcgc caaaggaatg caaggtctgt tgaatgtcgt
2501 gaaggaagca gttcctctgg aagcttcttg aagacaaaca acgtctgtag
2551 cgaccctttg caggcagcgg aacccccac ctggcgacag gtgcctctgc
2601 ggccaaaagc cacgtgtata agatacacct gcaaaggcgg cacaacccca
2651 gtgccacgtt gtgagttgga tagttgtgga aagagtcaaa tggctctcct
2701 caagcgtatt caacaagggg ctgaaggatg cccagaaggt accccattgt
2751 atgggatctg atctggggcc tcggtgcaca tgctttacat gtgtttagtc
2801 gaggttaaaa aacgtctagg ccccccgaac cacggggacg tggtttatcc
2851 tttgaaaaac acgatgcata atatggaaca aaaacttatt tctgaagaag
2901 acttggacac caaactttcc tgccgctcga tttctccacc cccaggtgaa
2951 ctcctccctc acctccccga cggggcgagg ctccatggct gccccctcgc
3001 tgcacccgtc tggtgccacg cggttccatg ggatcgtttc gcatgattga
3051 acaagatgga ttgcacgcag gttctccggc cgcttgggtg gagaggctat
3101 tcggctatga ctgggcacaa cagacaatcg gctgctctga tgccgccgtg
3151 ttccggctgt cagcgcaggg gcgcccggtt ctttttgtca agaccgacct
3201 gtccggtgcc ctgaatgaac tgcaggacga ggcagcgcgg ctatcgtggc
3251 tggccacgac gggcgttcct tgcgcagctg tgctcgacgt tgtcactgaa
3301 gcgggaaggg actggctgct attgggcgaa gtgccggggc aggatctcct
3351 gtcatctcac cttgctcctg ccgagaaagt atccatcatg gctgatgcaa
3401 tgcggcggct gcatacgctt gatccggcta cctgcccatt cgaccaccaa
3451 gcgaaacatc gcatcgagcg agcacgtact cggatggaag ccggtcttgt
3501 cgatcaggat gatctggacg aagagcatca ggggctcgcg ccagccgaac
3551 tgttcgccag gctcaaggcg cgcatgcccg acggcgagga tctcgtcgtg
3601 acccatggcg atgcctgctt gccgaatatc atggtggaaa atggccgctt
```

-continued

II. Nucleotide Sequences of Viral Vector Examples

```
3651 ttctggattc atcgactgtg gccggctggg tgtggcggac cgctatcagg
3701 acatagcgtt ggctacccgt gatattgctg aagagcttgg cggcgaatgg
3751 gctgaccgct tcctcgtgct ttacggtatc gccgctcccg attcgcagcg
3801 catcgccttc tatcgccttc ttgacgagtt cttctgagcg ggactctggg
3851 gttcgataaa ataaaagatt ttatttagtc tccagaaaaa gggggggaatg
3901 aaagacccca cctgtaggtt tggcaagcta gcttaagtaa cgccattttg
3951 caaggcatgg aaaaatacat aactgagaat agagaagttc agatcaaggt
4001 caggaacaga tggaacagct gaatatgggc caaacaggat atctgtggta
4051 agcagttcct gccccggctc agggccaaga acagatggaa cagctgaata
4101 tgggccaaac aggatatctg tggtaagcag ttcctgcccc ggctcagggc
4151 caagaacaga tggtcccag atgcggtcca gccctcagca gtttctagag
4201 aaccatcaga tgtttccagg gtgccccaag gacctgaaat gaccctgtgc
4251 cttatttgaa ctaaccaatc agttcgcttc tcgcttctgt tcgcgcgctt
4301 ctgctccccg agctcaataa aagagcccac aaccctcac tcggggcgcc
4351 agtcctccga ttgactgagt cgcccgggta cccgtgtatc caataaaccc
4401 tcttgcagtt gcatccgact tgtggtctcg ctgttccttg ggagggtctc
4451 ctctgagtga ttgactaccc gtcagcgggg gtctttcatt tggggctcg
4501 tccgggatcg ggagacccct gcccagggac caccgaccca ccaccgggag
4551 gtaagctggc tgcctcgcgc gtttcggtga tgacggtgaa aacctctgac
4601 acatgcagct cccggagacg gtcacagctt gtctgtaagc ggatgccggg
4651 agcagacaag cccgtcaggg cgcgtcagcg ggtgttggcg ggtgtcgggg
4701 cgcagccatg acccagtcac gtagcgatag cggagtgtat actggcttaa
4751 ctatgcggca tcagagcaga ttgtactgag agtgcaccat atgcggtgtg
4801 aaataccgca cagatgcgta aggagaaaat accgcatcag gcgctcttcc
4851 gcttcctcgc tcactgactc gctgcgctcg tcgttcggc tgcggcgagc
4901 ggtatcagct cactcaaagg cggtaatacg gttatccaca gaatcagggg
4951 ataacgcagg aaagaacatg tgagcaaaag gccagcaaaa ggccaggaac
5001 cgtaaaaagg ccgcgttgct ggcgtttttc cataggctcc gcccccctga
5051 cgagcatcac aaaaatcgac gctcaagtca gaggtggcga aacccgacag
5101 gactataaag ataccaggcg tttcccctg gaagctccct cgtgcgctct
5151 cctgttccga ccctgccgct taccggatac ctgtccgcct ttctcccttc
5201 gggaagcgtg gcgctttctc atagctcacg ctgtaggtat ctcagttcgg
5251 tgtaggtcgt tcgctccaag ctgggctgtg tgcacgaacc ccccgttcag
5301 cccgaccgct gcgccttatc cggtaactat cgtcttgagt ccaacccggt
5351 aagacacgac ttatcgccac tggcagcagc cactggtaac aggattagca
5401 gagcgaggta tgtaggcggt gctacagagt tcttgaagtg gtggcctaac
5451 tacggctaca ctagaaggac agtatttggt atctgcgctc tgctgaagcc
5501 agttaccttc ggaaaaagag ttggtagctc ttgatccggc aaacaaacca
5551 ccgctggtag cggtggtttt tttgtttgca agcagcagat tacgcgcaga
```

II. Nucleotide Sequences of Viral Vector Examples

*-continued*

```
5601 aaaaaaggat ctcaagaaga tcctttgatc ttttctacgg ggtctgacgc
5651 tcagtggaac gaaaactcac gttaagggat tttggtcatg agattatcaa
5701 aaaggatctt cacctagatc cttttaaatt aaaaatgaag ttttaaatca
5751 atctaaagta tatatgagta aacttggtct gacagttacc aatgcttaat
5801 cagtgaggca cctatctcag cgatctgtct atttcgttca tccatagttg
5851 cctgactccc cgtcgtgtag ataactacga tacgggaggg cttaccatct
5901 ggccccagtg ctgcaatgat accgcgagac ccacgctcac cggctccaga
5951 tttatcagca ataaaccagc cagccggaag ggccgagcgc agaagtggtc
6001 ctgcaacttt atccgcctcc atccagtcta ttaattgttg ccgggaagct
6051 agagtaagta gttcgccagt taatagtttg cgcaacgttg ttgccattgc
6101 tgcaggcatc gtggtgtcac gctcgtcgtt tggtatggct tcattcagct
6151 ccggttccca acgatcaagg cgagttacat gatccccat gttgtgcaaa
6201 aaagcggtta gctccttcgg tcctccgatc gttgtcagaa gtaagttggc
6251 cgcagtgtta tcactcatgg ttatggcagc actgcataat tctcttactg
6301 tcatgccatc cgtaagatgc ttttctgtga ctggtgagta ctcaaccaag
6351 tcattctgag aatagtgtat gcggcgaccg agttgctctt gcccggcgtc
6401 aacacgggat aataccgcgc cacatagcag aactttaaaa gtgctcatca
6451 ttggaaaacg ttcttcgggg cgaaaactct caaggatctt accgctgttg
6501 agatccagtt cgatgtaacc cactcgtgca cccaactgat cttcagcatc
6551 ttttactttc accagcgttt ctgggtgagc aaaaacagga aggcaaaatg
6601 ccgcaaaaaa gggaataagg gcgacacgga aatgttgaat actcatactc
6651 ttcctttttc aatattattg aagcatttat cagggttatt gtctcatgag
6701 cggatacata tttgaatgta tttagaaaaa taaacaaata ggggttccgc
6751 gcacatttcc ccgaaaagtg ccacctgacg tctaagaaac cattattatc
6801 atgacattaa cctataaaaa taggcgtatc acgaggccct ttcgtcttca
6851 a
``` pFB-cTAP-neo

```
   1 gaattgctag caattgctag caattgctag caattcatac cagatcaccg
  51 aaaactgtcc tccaaatgtg tcccctcac actcccaaat tcgcgggctt
 101 ctgcctctta gaccactcta ccctattccc cacactcacc ggagccaaag
 151 ccgcgggaca tatacatgtg aaagacccca cctgtaggtt tggcaagcta
 201 gcttaagtaa cgccattttg caaggcatgg aaaaatacat aactgagaat
 251 agaaaagttc agatcaaggt caggaacaga tggaacagct gaatatgggc
 301 caaagcggat atctgtggta agcagttcct gccccggctc agggccaaga
 351 acagatggaa cagctgaata tgggccaaac aggatatctg tggtaagcag
 401 ttcctgcccc ggctcagggc caagaacaga tggtcccag atgcggtcca
 451 gccctcagca gtttctagag aaccatcaga tgtttccagg gtgccccaag
 501 gacctgaaat gaccctgtgc cttatttgaa ctaaccaatc agttcgcttc
```

-continued

| | II. Nucleotide Sequences of Viral Vector Examples | | | |
|---|---|---|---|---|
| 551 | tcgcttctgt | tcgcgcgctt | ctgctccccg | agctcaataa | aagagcccac |
| 601 | aaccccctcac | tcggggcgcc | agtcctccga | ttgactgagt | cgcccgggta |
| 651 | cccgtgtatc | caataaaccc | tcttgcagtt | gcatccgact | tgtggtctcg |
| 701 | ctgttccttg | ggagggtctc | ctctgagtga | ttgactaccc | gtcagcgggg |
| 751 | gtctttcatt | tggggggctcg | tccgggatcg | ggagacccct | gcccagggac |
| 801 | caccgaccca | ccaccgggag | gtaagctggc | cagcaactta | tctgtgtctg |
| 851 | tccgattgtc | tagtgtctat | gactgatttt | atgcgcctgc | gtcggtacta |
| 901 | gttagctaac | tagctctgta | tctggcggac | ccgtggtgga | actgacgagt |
| 951 | tcggaacacc | cggccgcaac | cctgggagac | gtcccaggga | cttcggggc |
| 1001 | cgttttgtg | gcccgacctg | agtccaaaaa | tcccgatcgt | tttggactct |
| 1051 | ttggtgcacc | cccttagag | gagggatatg | tggttctggt | aggagacgag |
| 1101 | aacctaaaac | agttcccgcc | tccgtctgaa | tttttgcttt | cggtttggga |
| 1151 | ccgaagccgc | gccgcgcgtc | ttgtctgctg | cagcatcgtt | ctgtgttgtc |
| 1201 | tctgtctgac | tgtgtttctg | tatttgtctg | aaaatatggg | cccgggccag |
| 1251 | actgttacca | ctcccttaag | tttgaccttg | ggtcactgga | aagatgtcga |
| 1301 | gcggatcgct | cacaaccagt | cggtagatgt | caagaagaga | cgttgggtta |
| 1351 | ccttctgctc | tgcagaatgg | ccaaccttta | acgtcggatg | gccgcgagac |
| 1401 | ggcaccttta | accgagacct | catcacccag | gttaagatca | aggtcttttc |
| 1451 | acctggcccg | catggacacc | cagaccaggt | ccctacatc | gtgacctggg |
| 1501 | aagccttggc | ttttgacccc | cctccctggg | tcaagccctt | tgtacaccct |
| 1551 | aagcctccgc | ctcctcttcc | tccatccgcc | ccgtctctcc | ccttgaacc |
| 1601 | tcctcgttcg | accccgcctc | gatcctccct | ttatccagcc | ctcactcctt |
| 1651 | ctctaggcgc | ccccatatgg | ccatatgaga | tcttatatgg | ggcaccccg |
| 1701 | ccccttgtaa | acttccctga | ccctgacatg | acaagagtta | ctaacagccc |
| 1751 | ctctctccaa | gctcacttac | aggctctcta | cttagtccag | cacgaagtct |
| 1801 | ggagacctct | ggcggcacgt | accaagaaca | actggaccga | ccggtggtac |
| 1851 | ctcacccta | ccgagtcggc | gacacagtgt | gggtccgccg | acaccagact |
| 1901 | aagaacctag | aacctcgctg | gaaaggacct | tacacagtcc | tgctgaccac |
| 1951 | ccccaccgcc | ctcaaagtag | acggcatcgc | agcttggata | cacgccgccc |
| 2001 | acgtgaaggc | tgccgacccc | ggggtggac | catcctctag | actgccggat |
| 2051 | cgaattgtcg | acatcgatac | gcgtccagca | cagtgggaat | tcaggcctgg |
| 2101 | atcctcgaga | tggacgagaa | gaccaccggc | tggcggggcg | ccacgtggt |
| 2151 | ggagggcctg | gccggcgagc | tggagcagct | gcgggccagg | ctggagcacc |
| 2201 | accctcaggg | ccagcgggag | ccctccggcg | gctgcaagct | gggctccgga |
| 2251 | aagcgacgat | ggaaaagaa | tttcatagcc | gtctcagcag | ccaaccgctt |
| 2301 | taagaaaatc | tcatcctccg | gggcactta | gcggccgcg | atccggttat |
| 2351 | tttccaccat | attgccgtct | tttggcaatg | tgagggcccg | gaaacctggc |
| 2401 | cctgtcttct | tgacgagcat | tcctagggt | ctttcccctc | tcgccaaagg |
| 2451 | aatgcaaggt | ctgttgaatg | tcgtgaagga | agcagttcct | ctggaagctt |

II. Nucleotide Sequences of Viral Vector Examples

```
2501 cttgaagaca aacaacgtct gtagcgaccc tttgcaggca gcggaacccc
2551 ccacctggcg acaggtgcct ctgcggccaa aagccacgtg tataagatac
2601 acctgcaaag gcggcacaac cccagtgcca cgttgtgagt tggatagttg
2651 tggaaagagt caaatggctc tcctcaagcg tattcaacaa ggggctgaag
2701 gatgcccaga aggtacccca ttgtatggga tctgatctgg ggcctcggtg
2751 cacatgcttt acatgtgttt agtcgaggtt aaaaaacgtc taggcccccc
2801 gaaccacggg gacgtggttt atcctttgaa aaacacgatg cataatatgg
2851 aacaaaaact tatttctgaa gaagacttgg acaccaaact ttcctgccgc
2901 tcgatttctc cacccccagg tgaactcctc cctcacctcc ccgacggggc
2951 gaggctccat ggctgccccc tcgctgcacc cgtctggtgc cacgcggttc
3001 catgggatcg tttcgcatga ttgaacaaga tggattgcac gcaggttctc
3051 cggccgcttg ggtggagagg ctattcggct atgactgggc acaacagaca
3101 atcggctgct ctgatgccgc cgtgttccgg ctgtcagcgc aggggcgccc
3151 ggttcttttt gtcaagaccg acctgtccgg tgccctgaat gaactgcagg
3201 acgaggcagc gcggctatcg tggctggcca cgacgggcgt tccttgcgca
3251 gctgtgctcg acgttgtcac tgaagcggga agggactggc tgctattggg
3301 cgaagtgccg gggcaggatc tcctgtcatc tcaccttgct cctgccgaga
3351 aagtatccat catggctgat gcaatgcggc ggctgcatac gcttgatccg
3401 gctacctgcc cattcgacca ccaagcgaaa catcgcatcg agcgagcacg
3451 tactcggatg aagccggtc ttgtcgatca ggatgatctg gacgaagagc
3501 atcagggct cgcgccagcc gaactgttcg ccaggctcaa ggcgcgcatg
3551 cccgacggcg aggatctcgt cgtgacccat ggcgatgcct gcttgccgaa
3601 tatcatggtg gaaaatggcc gcttttctgg attcatcgac tgtggccggc
3651 tgggtgtggc ggaccgctat caggacatag cgttggctac ccgtgatatt
3701 gctgaagagc ttggcggcga atgggctgac cgcttcctcg tgctttacgg
3751 tatcgccgct cccgattcgc agcgcatcgc cttctatcgc cttcttgacg
3801 agttcttctg agcgggactc tggggttcga taaaataaaa gattttattt
3851 agtctccaga aaagggggg aatgaaagac cccacctgta ggtttggcaa
3901 gctagcttaa gtaacgccat tttgcaaggc atggaaaaat acataactga
3951 gaatagagaa gttcagatca aggtcaggaa cagatggaac agctgaatat
4001 gggccaaaca ggatatctgt ggtaagcagt tcctgccccg gctcagggcc
4051 aagaacagat ggaacagctg aatatgggcc aaacaggata tctgtggtaa
4101 gcagttcctg ccccggctca gggccaagaa cagatggtcc ccagatgcgg
4151 tccagccctc agcagtttct agagaaccat cagatgtttc cagggtgccc
4201 caaggacctg aaatgaccct gtgccttatt tgaactaacc aatcagttcg
4251 cttctcgctt ctgttcgcgc gcttctgctc cccgagctca ataaaagagc
4301 ccacaacccc tcactcgggg cgccagtcct ccgattgact gagtcgcccg
4351 ggtacccgtg tatccaataa accctcttgc agttgcatcc gacttgtggt
```

II. Nucleotide Sequences of Viral Vector Examples

```
4401 ctcgctgttc cttgggaggg tctcctctga gtgattgact acccgtcagc
4451 ggggtctttt catttggggg ctcgtccggg atcgggagac ccctgcccag
4501 ggaccaccga cccaccaccg ggaggtaagc tggctgcctc gcgcgtttcg
4551 gtgatgacgg tgaaaacctc tgacacatgc agctcccgga gacggtcaca
4601 gcttgtctgt aagcggatgc cgggagcaga caagcccgtc agggcgcgtc
4651 agcgggtgtt ggcgggtgtc ggggcgcagc catgacccag tcacgtagcg
4701 atagcggagt gtatactggc ttaactatgc ggcatcagag cagattgtac
4751 tgagagtgca ccatatgcgg tgtgaaatac cgcacagatg cgtaaggaga
4801 aaataccgca tcaggcgctc ttccgcttcc tcgctcactg actcgctgcg
4851 ctcggtcgtt cggctgcggc gagcggtatc agctcactca aaggcggtaa
4901 tacggttatc cacagaatca ggggataacg caggaaagaa catgtgagca
4951 aaaggccagc aaaaggccag gaaccgtaaa aaggccgcgt tgctggcgtt
5001 tttccatagg ctccgccccc ctgacgagca tcacaaaaat cgacgctcaa
5051 gtcagaggtg gcgaaacccg acaggactat aaagatacca ggcgtttccc
5101 cctggaagct ccctcgtgcg ctctcctgtt ccgaccctgc cgcttaccgg
5151 atacctgtcc gcctttctcc cttcgggaag cgtggcgctt tctcatagct
5201 cacgctgtag gtatctcagt tcggtgtagg tcgttcgctc caagctgggc
5251 tgtgtgcacg aaccccccgt tcagcccgac cgctgcgcct tatccggtaa
5301 ctatcgtctt gagtccaacc cggtaagaca cgacttatcg ccactggcag
5351 cagccactgg taacaggatt agcagagcga ggtatgtagg cggtgctaca
5401 gagttcttga agtggtggcc taactacggc tacactagaa ggacagtatt
5451 tggtatctgc gctctgctga agccagttac cttcggaaaa agagttggta
5501 gctcttgatc cggcaaacaa accaccgctg gtagcggtgg tttttttgtt
5551 tgcaagcagc agattacgcg cagaaaaaaa ggatctcaag aagatccttt
5601 gatcttttct acggggtctg acgctcagtg gaacgaaaac tcacgttaag
5651 ggattttggt catgagatta tcaaaaagga tcttcaccta gatccttta
5701 aattaaaaat gaagttttaa atcaatctaa agtatatatg agtaaacttg
5751 gtctgacagt taccaatgct taatcagtga ggcacctatc tcagcgatct
5801 gtctatttcg ttcatccata gttgcctgac tccccgtcgt gtagataact
5851 acgatacggg agggcttacc atctggcccc agtgctgcaa tgataccgcg
5901 agacccacgc tcaccggctc cagatttatc agcaataaac cagccagccg
5951 gaagggccga gcgcagaagt ggtcctgcaa ctttatccgc ctccatccag
6001 tctattaatt gttgccggga agctagagta agtagttcgc cagttaatag
6051 tttgcgcaac gttgttgcca ttgctgcagg catcgtggtg tcacgctcgt
6101 cgtttggtat ggcttcattc agctccggtt cccaacgatc aaggcgagtt
6151 acatgatccc ccatgttgtg caaaaaagcg gttagctcct tcggtcctcc
6201 gatcgttgtc agaagtaagt tggccgcagt gttatcactc atggttatgg
6251 cagcactgca taattctctt actgtcatgc catccgtaag atgcttttct
6301 gtgactggtg agtactcaac caagtcattc tgagaatagt gtatgcggcg
```

| II. Nucleotide Sequences of Viral Vector Examples |
|---|
| 6351 accgagttgc tcttgcccgg cgtcaacacg ggataatacc gcgccacata |
| 6401 gcagaacttt aaaagtgctc atcattggaa aacgttcttc ggggcgaaaa |
| 6451 ctctcaagga tcttaccgct gttgagatcc agttcgatgt aacccactcg |
| 6501 tgcacccaac tgatcttcag catcttttac tttcaccagc gtttctgggt |
| 6551 gagcaaaaac aggaaggcaa aatgccgcaa aaagggaat aagggcgaca |
| 6601 cggaaatgtt gaatactcat actcttcctt tttcaatatt attgaagcat |
| 6651 ttatcagggt tattgtctca tgagcggata catatttgaa tgtatttaga |
| 6701 aaaataaaca aatagggtt ccgcgcacat ttccccgaaa agtgccacct |
| 6751 gacgtctaag aaaccattat tatcatgaca ttaacctata aaaataggcg |
| 6801 tatcacgagg ccctttcgtc ttcaa |

The invention claimed is:

1. A viral vector comprising a polynucleotide sequence comprising at least two different affinity tag sequences, wherein one of said two affinity tag sequences encodes streptavidin-binding peptide having a nucleotide sequence selected from the group consisting of SEQ ID No.: 5 and SEQ ID No.: 7.

2. A viral vector comprising a polynucleotide sequence comprising a gene sequence of interest and at least two affinity tag sequences, wherein said gene sequence of interest is fused in frame with each of said affinity tag sequences, and wherein one of said at least two affinity tag sequences encodes streptavidin-binding peptide having a nucleotide sequence selected from the group consisting of SEQ ID No.: 5 and SEQ ID No.: 7.

3. A viral vector comprising a polynucleotide comprising at least two different affinity tag sequences, wherein one of said at least two affinity tag sequences encodes streptavidin binding peptide, and wherein one of said at least two affinity tag sequences encodes calmodulin binding peptide.

4. A viral vector comprising a polynucleotide comprising a gene sequence of interest and at least two affinity tag sequences, wherein said gene sequence of interest is fused in frame with each of said affinity tag sequences, and wherein one of said at least two affinity tag sequences encodes streptavidin binding peptide, and wherein one of said at least two affinity tag sequences encodes calmodulin binding peptide.

5. The viral vector of claim 2 or 4, wherein both of said affinity tags are adjacent to the 5' end of the target gene or wherein both of said affinity tags are adjacent to the 3' end of the gene.

6. The viral vector of any one of claims 1–4 wherein said viral vector comprises an adenoviral vector or a retroviral vector.

7. An isolated host cell infected with the viral vector of claim 1.

8. A viral particle comprising a polynucleotide sequence comprising at least two affinity tag sequences, wherein one of said at least two affinity tag sequences encodes streptavidin-binding peptide having a nucleotide sequence selected from the group consisting of SEQ ID No.: 5 and SEQ ID No.: 7.

9. A viral particle comprising a polynucleotide sequence comprising a gene sequence of interest and at least two affinity tag sequences, wherein said gene sequence of interest is fused in frame with each of said affinity tag sequences, and wherein one of said at least two affinity tag sequences encodes streptavidin-binding peptide having a nucleotide sequence selected from the group consisting of SEQ ID No.: 6 and SEQ ID No.: 8.

10. A viral particle comprising a polynucleotide sequence comprising at least two different affinity tag sequences, wherein one of said at least two affinity tag sequences encodes streptavidin binding peptide, and wherein one of said at least two affinity tag sequences encodes calmodulin binding peptide.

11. A viral particle comprising a polynucleotide comprising a gene sequence of interest and at least two affinity tag sequences, wherein said gene sequence of interest is fused in frame with each of said affinity tag sequences, and wherein one of said at least two affinity tag sequences encodes streptavidin binding peptide, and wherein one of said at least two affinity tag sequences encodes calmodulin binding peptide.

12. The viral particle of claim 9 or 11 wherein both of said affinity tags are adjacent to the N-terminus of the protein of interest or wherein both of said affinity tags are adjacent to the C-terminus of the protein of interest.

13. A composition comprising a viral particle of claim 8 or 9.

14. A method of detecting or isolating one or more binding partners for a protein encoded by a gene of interest, comprising the steps:
cloning a gene sequence of interest into a viral vector, wherein said gene sequence of interest is fused in frame with at least two different affinity tag sequences, and wherein one of said at least two affinity tag sequences encodes streptavidin binding peptide having the amino acid sequence selected from the group consisting of SEQ ID No.: 5 and SEQ ID No.: 7,
introducing said viral vector into an isolated host cell that comprises at least one candidate binding partner for said protein product of said gene of interest;

allowing said protein product of said gene sequence of interest and said candidate binding partner to form a complex in the cell;
isolating said complex by
a) lysing the cells; and
b) performing at least one round of affinity purification and;
detecting said protein complex.

15. A method of detecting or isolating one or more binding partners for a protein encoded by a gene sequence of interest, comprising the steps:
cloning a gene sequence of interest into a viral vector, wherein said gene sequence of interest is fused in frame with at least two different affinity tag sequences, and wherein one of said at least two affinity tag sequences encodes streptavidin binding peptide, and wherein one of said at least two affinity tag sequences encodes calmodulin binding peptide;
introducing said vector into an isolated host cell that comprises at least one candidate binding partner for said protein product of said gene sequence of interest;
allowing said protein product of said gene of interest and said candidate binding partner to form a complex in the cell;
isolating said complex by
a) lysing the cells; and
b) performing at least one round of affinity purification and;
detecting said protein complex.

16. The method of claim 14 or 15 wherein said viral vector comprises an adenoviral vector or a retroviral vector.

17. A method of detecting or isolating a protein complex comprising the steps of:
cloning a gene sequence of interest into a viral vector, wherein said gene sequence of interest is fused in frame with at least two different affinity tag sequences, and wherein one of said at least two affinity tag sequences encodes streptavidin binding peptide having the amino acid sequence selected from the group consisting of SEQ ID No.: 6 and SEQ ID No.: 8;
introducing said viral vector into an isolated host cell that expresses at least one protein binding partner for said protein product of said gene sequence of interest;
allowing said protein product of said gene sequence of interest and said protein binding partner to form a complex in the cell;
isolating said complex by
a) lysing the cells; and
b) performing at least one round of affinity purification and;
detecting said protein complex.

18. A method of detecting or isolating a protein complex comprising the steps of:
cloning a gene sequence of interest into a viral vector, wherein said gene sequence of interest is fused in frame with at least two different affinity tag sequences, and wherein one of said at least two affinity tag sequences encodes streptavidin binding peptide, and wherein one of said at least two affinity tag sequences encodes calmodulin binding peptide;
introducing said viral vector into an isolated host cell that expresses at least one protein binding partner for said protein product of said gene sequence of interest;
allowing said protein product of said gene sequence of interest and said protein binding partner to form a complex in the cell;
isolating said complex by
a) lysing the cells; and
b) performing at least one round of affinity purification and;
detecting said protein complex.

19. The method of claim 17 or claim 18 wherein said viral vector comprises an adenoviral vector or a retroviral vector.

20. The method of claim 14 or 17, wherein said complex is isolated by performing at least two successive rounds of affinity purification.

21. A kit for isolating a protein complex or identifying one or more binding partners for a protein, comprising the viral vector of claim 1, and packaging materials.

* * * * *